(12) United States Patent
Sirdeshmukh et al.

(10) Patent No.: US 11,826,314 B2
(45) Date of Patent: *Nov. 28, 2023

(54) MEDICATION ADHERENCE APPARATUS AND METHODS OF USE

(71) Applicant: Sensal Health, LLC, Chapel Hill, NC (US)

(72) Inventors: Deepak Sirdeshmukh, Chapel Hill, NC (US); Nestorius Wiegandt, Perth (CA); Ashok Kumar Krishnamurthy, Chapel Hill, NC (US); James Vincent Kokal, Plano, TX (US); Robert Benkowski, Fort Worth, TX (US); Javier Oliver, Dallas, TX (US); Laurent Gregoire Benkowski, Houston, TX (US)

(73) Assignee: SENSAL HEALTH, LLC

( * ) Notice: Subject to any disclaimer, the term of this patent is extended or adjusted under 35 U.S.C. 154(b) by 946 days.

This patent is subject to a terminal disclaimer.

(21) Appl. No.: 16/598,528

(22) Filed: Oct. 10, 2019

(65) Prior Publication Data

US 2020/0113787 A1    Apr. 16, 2020

Related U.S. Application Data

(60) Provisional application No. 62/743,964, filed on Oct. 10, 2018.

(51) Int. Cl.
*A61J 7/04* (2006.01)
*G16H 20/13* (2018.01)
(Continued)

(52) U.S. Cl.
CPC .............. *A61J 7/0481* (2013.01); *A61J 1/03* (2013.01); *A61J 1/1412* (2013.01); *A61J 1/1418* (2015.05); *A61J 1/18* (2013.01); *A61J 7/04* (2013.01); *A61J 7/0418* (2015.05); *A61J 7/0436* (2015.05); *G06F 21/6218* (2013.01);
(Continued)

(58) Field of Classification Search
CPC .... A61J 2200/74; A61J 2200/30; G16H 20/13
See application file for complete search history.

(56) References Cited

U.S. PATENT DOCUMENTS 10,515,720 B2 * 12/2019 Fateh ................... A61J 7/0015
10,888,502 B2 *  1/2021 Sirdeshmukh ....... G06Q 10/087
(Continued)

FOREIGN PATENT DOCUMENTS

WO    2013/127564 A2    9/2013
WO    2016/179537 A2    11/2016
WO    2018/065122 A2    4/2018

OTHER PUBLICATIONS

Supplementary European Search Report 19871719.1, dated Dec. 8, 2021.

*Primary Examiner* — Timothy R Waggoner
(74) *Attorney, Agent, or Firm* — The Belles Group, P.C.

(57) ABSTRACT

Provided herein are systems, methods and apparatuses for a medication adherence apparatus and methods of use. A method of adhering to medical prescription requirements combines sensors and hardware to record a cap state including an orientation, temperature, time stamp, and location of a cap device to enhance a patient's adherence to medical prescription when operably coupled with a computing device.

18 Claims, 45 Drawing Sheets

(51) Int. Cl.
*A61J 1/14* (2023.01)
*A61J 1/18* (2023.01)
*A61J 1/03* (2023.01)
*G16H 15/00* (2018.01)
*G16H 10/20* (2018.01)
*G06F 21/62* (2013.01)
*G06Q 10/087* (2023.01)

(52) U.S. Cl.
CPC ........... *G06Q 10/087* (2013.01); *G16H 10/20* (2018.01); *G16H 15/00* (2018.01); *G16H 20/13* (2018.01); *A61J 2200/30* (2013.01); *A61J 2200/72* (2013.01); *A61J 2200/74* (2013.01)

(56) References Cited

U.S. PATENT DOCUMENTS

| | | | |
|---|---|---|---|
| D937,674 S | 12/2021 | Griffin et al. | |
| 2010/0164716 A1* | 7/2010 | Estevez | G07F 13/025 700/244 |
| 2014/0262918 A1* | 9/2014 | Chu | G16H 20/13 206/534 |
| 2015/0108026 A1* | 4/2015 | Azimi | G16H 40/67 206/459.1 |
| 2016/0327427 A1* | 11/2016 | Briones | G16H 20/13 |
| 2018/0042817 A1* | 2/2018 | Wachman | B65D 51/248 |
| 2018/0349561 A1* | 12/2018 | Lecamus | G16H 20/13 |
| 2020/0135321 A1* | 4/2020 | Lebrun | G06F 21/33 |

\* cited by examiner

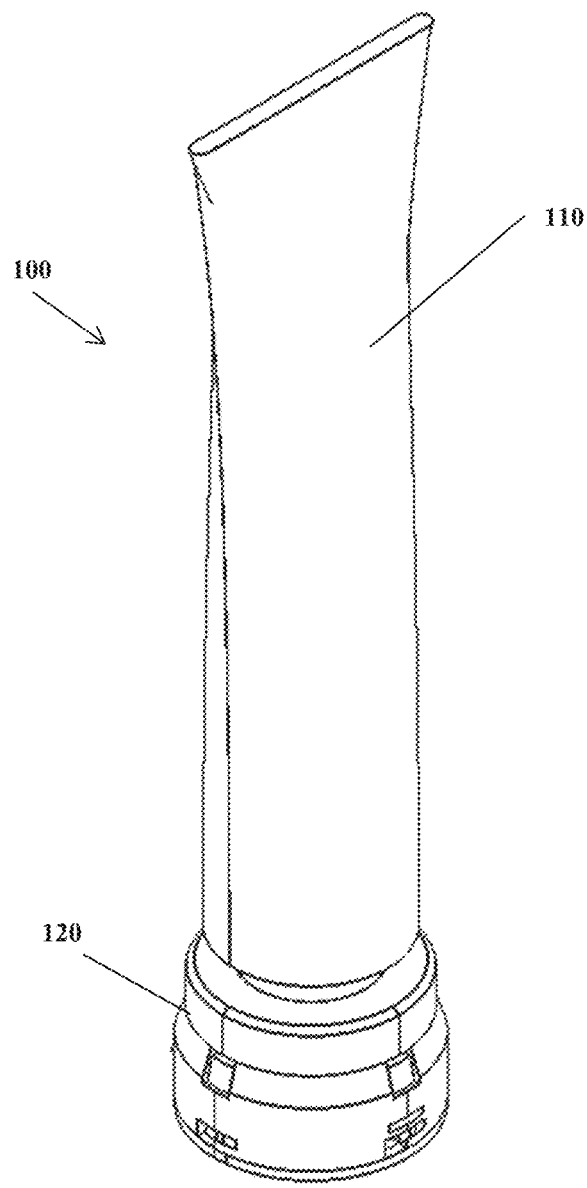
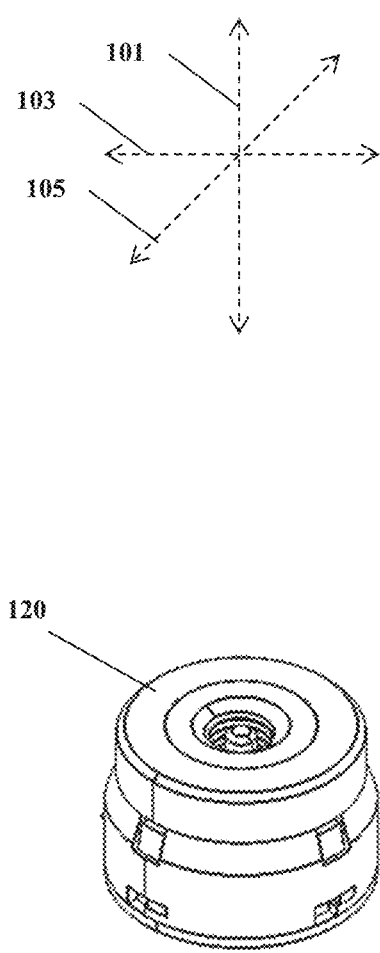
FIG. 1
FIG. 2A ns of the appended claims. It is to be understood that both the foregoing general description and the following detailed description are exemplary and explanatory only and are not restrictive of the methods, apparatuses, and systems, as claimed.

MEDICATION ADHERENCE APPARATUS AND METHODS OF USE

CROSS-REFERENCE TO RELATED APPLICATIONS

The present application claims priority to U.S. provisional application Ser. No. 62/743,964, filed Oct. 10, 2018, herein incorporated by reference in its entirety.

BACKGROUND

The invention generally relates to medication adherence.

Outpatient prescription medication treatments are relied upon for increased quality of life and lower lifetime healthcare costs. Taking at least 80% of a prescribed drug is required to achieve desired therapeutic outcomes and lower lifetime healthcare costs. Outpatients strongly desire to avoid such events and hospital stays, yet only 20% of all outpatients take their prescription medicines according to doctor's instructions.

Increased medication adherence, also known as patient adherence, medication adherence, or patient compliance, benefits the healthcare system by vastly reducing patients' lifetime medical costs while increasing their therapeutic outcomes. Further, patients have a desire to adhere, but will not take on the burden of any additional actions or otherwise change their behavior. The present invention solves these problems as well as others.

SUMMARY OF THE INVENTION

Provided herein are systems, methods and apparatuses for a medication adherence apparatus and methods of use.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1 is a perspective view of the medication adherence apparatus.

FIG. 2A is a perspective view of the cap device, according to one embodiment.

DETAILED DESCRIPTION OF THE INVENTION

Figure 2B:
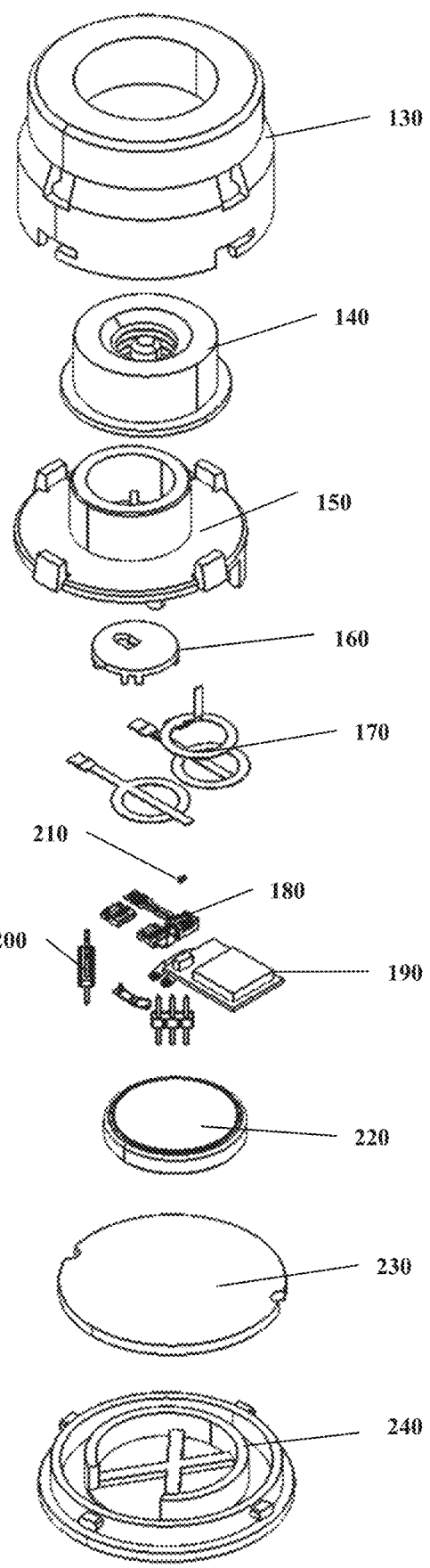
FIG. 2B is an exploded view of the cap device, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Generally speaking, the medication adherence apparatus 100 and methods of use comprise a container element 110 and a cap device 120 including a hardware system, as shown in FIG. 1. The cap device 120 without the container element 110 is shown in FIG. 2A. The container element 110 may be any container element to house a medication, such as a collapsible tube made of metal or metal lined, made of low-density polyethylene or made from laminated material, wide-mouthed plastic jar, rigid bottle or jar constructed of glass or polypropylene or a platform developed for storage, display, and utilization of medicament containers such as a tube, pill bottle, balm jar or tray. The medication may be any type of medication, either in pill, powder, liquid, or gas form. The cap state comprises the force or weight of the container element, the orientation of the cap device 120, the temperature of the cap device 120, and the time stamp including the day, time, and date. The force or weight of the container element 110 is obtained when the container element 110 is inserted into the cap device 120. The temperature inside the mouth of the container element 110 is obtained by the cap device 120. The presence or absence of the container element 110 in the cap device 120 is detected by the cap device 120. The orientation of the cap device 120 is detected to determine if the cap device 120 and/or the container element 110 is upright, which is generally along the vertical axis 101. And any movements of the cap device 120 may be detected, such as along the vertical axis 101, the longitudinal axis 103, or the lateral axis 105. The cap device 120 detects the weight of the container element 110 and stores or sends an information signal of the weight of the container element. The cap device detects the cap state and whether the container element is attached or connected to the cap device and stores or sends the cap state information signal. The cap device 120 receives a medication schedule and notification parameters to notify a patient by an alarm if medication is missed. The alarm may be an audio sound, a visual notification, an electronic notification, indicators, or a cell phone notification. The cap device records then time of when the patient starts the adherence (cap device is off the container element) and ends the adherence (cap device is on the container element), which is used for further diagnostics, such as when the patient starts taking it but then closes up again after about 3 s.

The medication adherence apparatus helps patients adhere to medical prescription requirements. The medication adherence apparatus comprises a hardware combining sensors to record cap state including the position, orientation, temperature, time stamp, and location of the cap device and thus enhance patient's adherence to medical prescription when operably coupled with a mobile device or other computing device. The medication adherence apparatus can send the compliance information to a mobile application or the cloud, and can accessible by the patient and/or doctor so there is a real-time feedback of his progress of prescription compliance and adjust any prescription behavior accordingly. In one embodiment, the compliance information is sent to a web server accessible by the treating doctor who can objectively monitor patients' compliance. The container element may be any element that holds and dispenses medication. In one embodiment, the container element is a tube that dispenses topical medication. Medication may be in a lotion form, a pill form, a powder form, or liquid form. A medication (also referred to as medicine, pharmaceutical drug, or simply drug) is a drug used to diagnose, cure, treat, or prevent disease.

In general, a mobile device may include any mobile telecommunications device such as, but not limited to, a mobile (e.g., cellular) phone or equivalent, including an iPhone™, Droid™, or the like. A mobile telecommunications device typically may include a processor or other computing module/device which may include software module, hardware, or the like, including machine readable code configured to operate the device to receive and/or send information from the apparatus described herein. Such code may be provided with, or separately from, the apparatus described. A mobile telecommunications device may be referred to (and includes) a cell or cellular phone or telephone, a mobile phone or telephone, a smartphone, smart eye glasses or virtual reality glasses; an handheld computer, tablet, a wearable computer, a wearable sensor, an electronic book reader, electronically-functional jewelry, or the like. Code may be referred to a software, or application software ("app" or "application") and may be downloaded from a remote location onto the mobile telecommunications device.

Figure 2C:
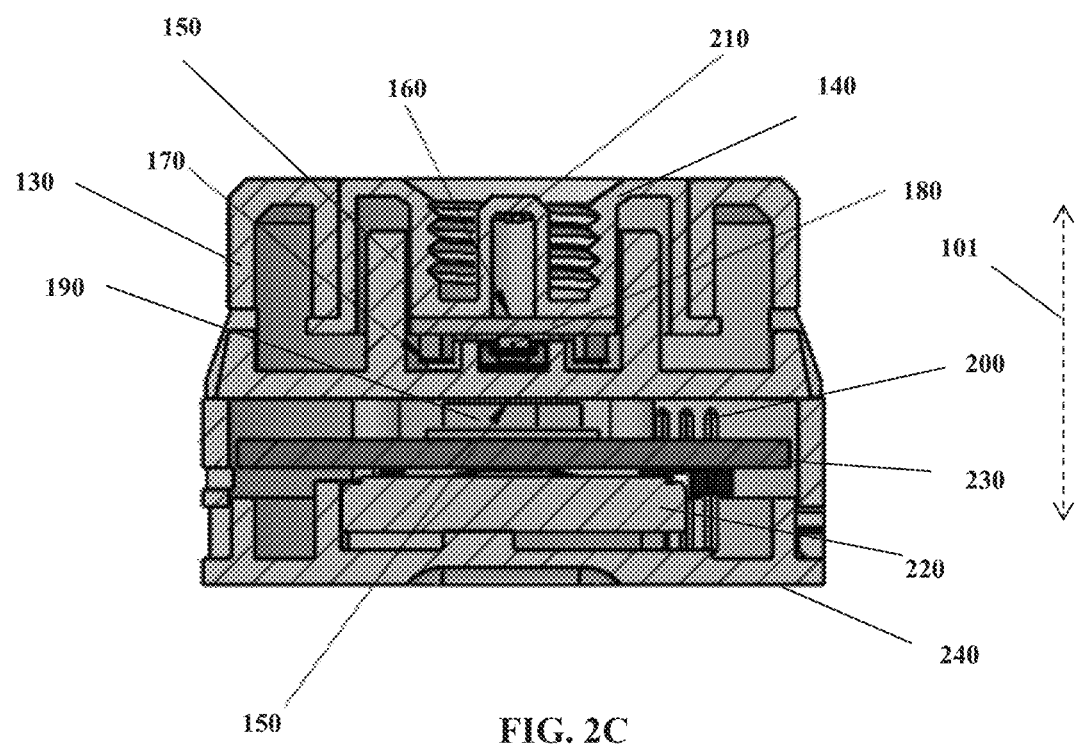
FIG. 2C is a cross-sectional view of the cap device, according one embodiment.

As shown in FIG. 2B, the cap device 120 comprises a main housing 130, a tube connector 140, a sensor socket 150, a sensor cover 160, a connector thermistor proximity 170, a force sensor unit 180, a memory circuit 190, an accelerometer 200, a temperature sensor 210, a battery 220, a PCB (printed circuit board) or board 230, and a battery cover 240. The tube connector 140 may be altered such that different types of container elements 110 may be coupled with the cap device 120. As shown in FIG. 2C, the main housing 130 is operably disposed over the sensor socket 150 and the battery cover 240 as to enclose the cap device 120. The tube connector 140 is operably coupled with the main housing 130 as to secure the cap device 120 to the container 110 and move axially down the vertical axis 101 in the while sitting on the sensor cover 160. The temperature sensor 210 is operably disposed within the tube connector and the force sensor unit 180 is operably disposed between the sensor cover 160 and the sensor socket 150. The connector thermistor proximity 170 is operably coupled through the sensor cover 160 and the sensor socket 150 to the PCB cap 230. The sensor cover 160 is disposed on the force sensor unit 180, while the force sensor unit 180 is disposed in the sensor socket 150. The force sensor unit 180 detects the force or weight of the container element 110 inserted into the cap device 120.

The sensor socket 150 includes a rigid snap connection to the main housing 130. The PCB cap 230 is operably coupled with the force sensor unit 180, the connector thermistor proximity 170 and the memory circuit 190. The battery 220 is operably disposed in the battery cover 240 and the accelerometer 200 is operably disposed in the battery cover 240 through the PCB cap 230. The temperature sensor 210 detects the temperature inside the mouth of the container element 110. The connector thermistor proximity 170 is operably disposed on top of the sensor socket 150. The connector thermistor proximity sensor senses when the container element 110 is present or absent from the cap device 120. The accelerometer 200 detects the orientation of the cap device 120 and registers when the cap device 120 is upright along vertical axis direction 101 so the weight can be measured. The accelerometer 200 also detects movements of the container element 110 such as twisting cap device open or close, shaking the container element 110, or tilting of the container element 110. Data is stored in the memory circuit 190, which includes a wireless module to communicate the cap state information to a mobile telecommunications device.

In one embodiment, the technology platform for supporting medication adherence management consists of a smart peripheral sensor device (cap device) that tracks parameters such as amount of medication dispensed, temperature at medication dispensation, time at medication dispensation; a smartphone application (Mobile Application) for tracking medication adherence that communicates with the cap device using the BLE data protocol; and cloud web servers with a database thereon for storing adherence data (Web System) or server database and which communicates with Mobile Application for data upload/download.

The Mobile Application can communicate with the cap device using low power Bluetooth (BLE) and with the Web System using a WiFi or cellular network. The Mobile Application determines if the patient is taking the medicine based on data from the cap device and produce local alerts based on protocols established. The Mobile Application executes the established protocols and provides additional adherence reporting capabilities and facilitates surveys of the patient. Mobile Application check last data sync timestamp with the sensor device for each BLE connection established and pull in available data from the cap device and gathering data. The Mobile Application transits this data back to Web System, as well as, receives data and parameters from the Web System.

The Web System includes web based server code for enabling the personalization of system communications through messages and surveys based on adherence criteria of: whether medication is applied or not applied; time when medication is applied; quantity of medication applied during each dose.

The Mobile Application determines if patient is taking the medicine based on the cap device/sensor peripherals and produce local alerts based on protocols established. App provides additional adherence reporting capabilities and facilitates surveys. Mobile app checks last data sync timestamp with the sensor device for each BLE connection established and pull in available data from sensor. The mobile app transits this data back to servers when cellular or other internet connection is available.

The Web System includes database systems that store the medication adherence data from a collection of patients, and software code for predictive algorithms that can predict patient adherence trends from the collected data, stratify patient behavior based on adherence data and survey results, and determine suitable messages to be provided to the Mobile Application to improve patient adherence. Data gathered from all patients is used to model patient behavior with respect to skipping medications and other non-adherence trends.

The Web System includes an Administrative Web Portal that is used to provision accounts for Clinical Research Organizations (CROs). The CROs use this Administrative Web Portal to manage patients participating in the trial, their medication schedules specific to a trial, setting up surveys and data reports, and provide medication adherence reporting.

The technology platform includes data security layers across the Web System, the Mobile Application and the cap device. Password protection and encryption of data occurs at every level and provide secure compliances for HIPAA. The web services programs (Application Programmable Interface) which provide transmission layer for data flow between server and mobile have secure HTTPS protocol implemented.

Sensors

The accelerometer may be an orientation sensor, including a gyroscope, a magnetometer or any combination, can be used for sensing the orientation of the cap device 110. For example, fusing the data from accelerometer, gyroscope and magnetometer makes good use of the quick response time and sensitivity of the gyroscope, while the accelerometer and the magnetometer can correct the gyroscope drift over a long period. An accelerometer is an electromechanical device used to measure acceleration forces. Such forces may be static, like the continuous force of gravity or, as is the case with many mobile devices, dynamic to sense movement or vibrations. A motion sensor, such as Bosch BNO055, can be used for sensing. The sensor consists of accelerometer, gyroscope and magnetometer, from which the data is fused into stable three-axis orientation output. The orientation references the direction of gravity and Earth's magnetic field. The sensor chip is small enough to be attached to battery cover. When used alone, the accelerometer can detect acceleration and the gyroscope can detect angular velocity. In one embodiment, the accelerometer includes a high cross axis sensitivity, where the accelerometer detects disturbances of delta X~0.002, delta Y~0.001, and delta Z~0.000.

The connector thermistor proximity 170 is a sensor able to detect the presence of the container element without any physical contact. In one embodiment, the proximity sensor emits an electromagnetic field or a beam of electromagnetic radiation (infrared, for instance), and looks for changes in the field or return signal. The container element being sensed is the proximity sensor's target. Different proximity sensor targets demand different sensors. For example, a capacitive proximity sensor or photoelectric sensor might be suitable for a plastic target; an inductive proximity sensor always requires a metal target. Proximity sensors can have a high reliability and long functional life because of the absence of mechanical parts and lack of physical contact between the sensor and the sensed object. Proximity sensors may also be used to measure the variation in distance between the cap device and the container element. A sensor alarm may issue if the proximity sensor detects the container element being separated from the cap device for a period of time. The period of time may be between about 1 minute and about 100 minutes. This sensor alarm ensures the container element is not separated from the cap device for too long as to lose medication or expose medication to air or degradation elements. The proximity sensor is a capacitive sensor. In other embodiments, touchless sensors may be used as the proximity sensor such as an inductive sensor (electromagnetic field) or an optical sensor, infrared, and the like. In one embodiment, the proximity sensor is a conventional switch.

The force sensor unit 180 may be a piezoelectric sensor, a force-sensing resistor, a shear-beam load cell, or a force-sensing capacitor. A piezoelectric sensor is a device that uses the piezoelectric effect, to measure changes in pressure, acceleration, temperature, strain, or force by converting them to an electrical charge. The piezoelectric using effect of piezo resistive bridge circuit formed on silicon diaphragm, where the piezo resistance is changed according to strain by applying force to the diaphragm. A force-sensing resistor includes a material whose resistance changes when a force, pressure or mechanical stress is applied. Force-sensing resistors consist of a conductive polymer, which changes resistance in a predictable manner following application of force to its surface. They are normally supplied as a polymer sheet or ink that can be applied by screen printing. The sensing film consists of both electrically conducting and non-conducting particles suspended in matrix. The particles are sub-micrometer sizes, and are formulated to reduce the temperature dependence, improve mechanical properties and increase surface durability. Applying a force to the surface of the sensing film causes particles to touch the conducting electrodes, changing the resistance of the film. As with resistive based sensors, force-sensing resistors require a relatively simple interface and can operate satisfactorily in moderately hostile environments. Compared to other force sensors, the advantages of FSRs are their size (thickness typically less than 0.5 mm), low cost and good shock resistance. Force-sensing capacitors include a material whose capacitance changes when a force, pressure or mechanical stress is applied. Force sensitive capacitors are examples of parallel plate capacitors. For small deflections, there is a linear relationship between applied force and change in capacitance. A shear beam load cell uses regular strain gages, which are resistors that change the resistance with deformation.

In one embodiment, the temperature sensor includes an error reading greater than or equal to about 0.023 degrees Celsius, and an accuracy less than or equal to about 97.6%. Generally speaking, the temperature sensor may be selected from the group consisting of: Negative Temperature Coefficient (NTC) thermistor, Resistance Temperature Detector (RTD), Thermocouples, and Semiconductor-based sensors. The temperature sensor may also include a temperature alarm, that sounds off when a specified temperature is reached. The specified temperature may be set by the medication and its requirements for storage. In one embodiment, the specified temperature is set between about 20° C. and about 30° C. to ensure the medication is properly stored.

A Negative Temperature Coefficient (NTC) thermistor is a thermally sensitive resistor that exhibits a large, predictable, and precise change in resistance correlated to variations in temperature. An NTC thermistor provides a very high resistance at low temperatures. As temperature increases, the resistance drops quickly. Because an NTC thermistor experiences such a large change in resistance per ° C., small changes in temperature are reflected very fast and with high accuracy (0.05 to 1.5° C.). Because of its exponential nature, the output of an NTC thermistor requires linearization. The effective operating range is about −50 to about 250° C. for gas encapsulated thermistors or about 150° C. for measurements.

A Resistance Temperature Detector (RTD) is also known as a resistance thermometer, measures temperature by correlating the resistance of the RTD element with temperature. An RTD consists of a film or, for greater accuracy, a wire wrapped around a ceramic or glass core. The most accurate RTDs are made using platinum but lower cost RTDs can be made from nickel or copper. However, nickel and copper are not as stable or repeatable. Platinum RTDs offer a fairly linear output that is highly accurate (0.1 to 1° C.) across −200 to 600° C. While providing the greatest accuracy, RTDs also tend to be the most expensive of temperature sensors.

Thermocouple is a temperature sensor type that consists of two wires of different metals connected at two points. The varying voltage between these two points reflects proportional changes in temperature. Thermocouples are non-linear, requiring conversion when used for temperature control and compensation, typically accomplished using a lookup table. Accuracy is low, from about 0.5 to about 5° C. However, they operate across the widest temperature range, from about −200 to about 1750° C.

Semiconductor-based sensors are placed on integrated circuits (ICs). These sensors are effectively two identical diodes with temperature-sensitive voltage vs current characteristics that can be used to monitor changes in temperature. They offer a linear response but have the lowest accuracy of the basic sensor types at about 1 to about 5° C. They also have the slowest responsiveness (about 5 to about 60 s) across the narrowest temperature range (−70 to 150° C.).

The wireless module is for wireless communication capabilities for communicating with a computer or mobile device. For example, the wireless module may be Bluetooth®-enabled, Wi-Fi-enabled, Infrared, and/or any other wireless communication interface-enabled for communicating wirelessly with other local devices. Examples of wireless communication interfaces may include, but are not limited to, an Intranet connection, Internet, ISM, Bluetooth R) technology, Wi-Fi, Wi-Max, IEEE 402.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

Figure 3A:
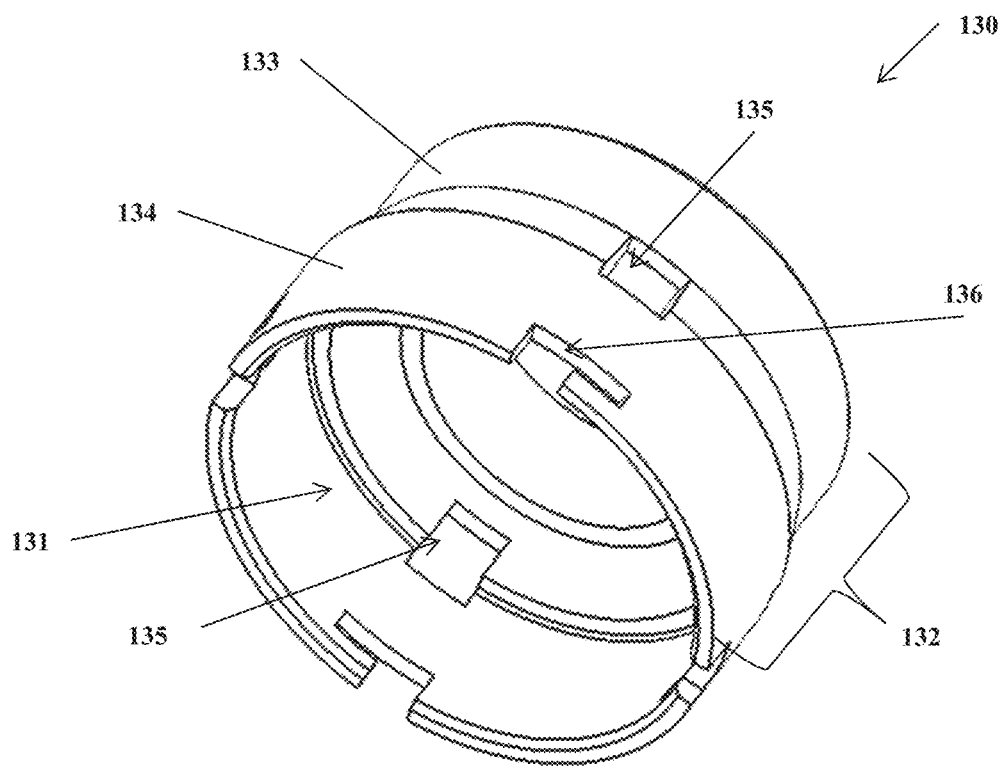
FIG. 3A is a perspective bottom view of the main housing.
Figure 3B:
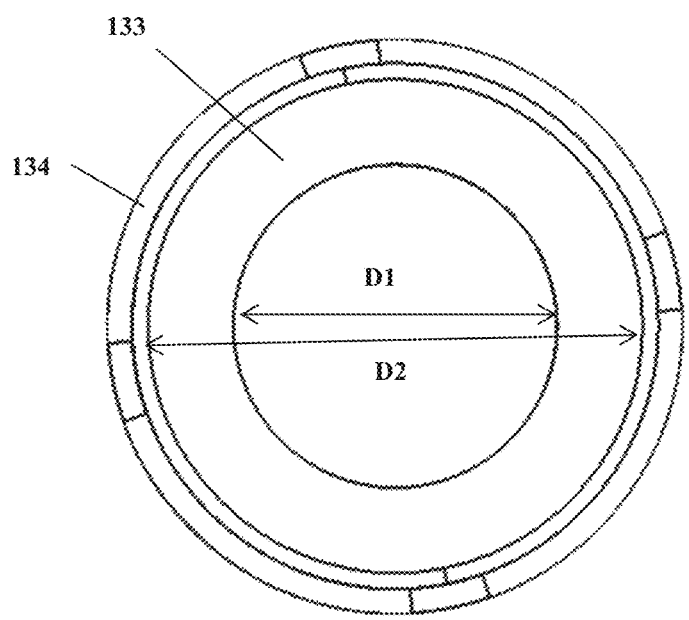
FIG. 3B is a top view of the main housing.
Figure 3C:
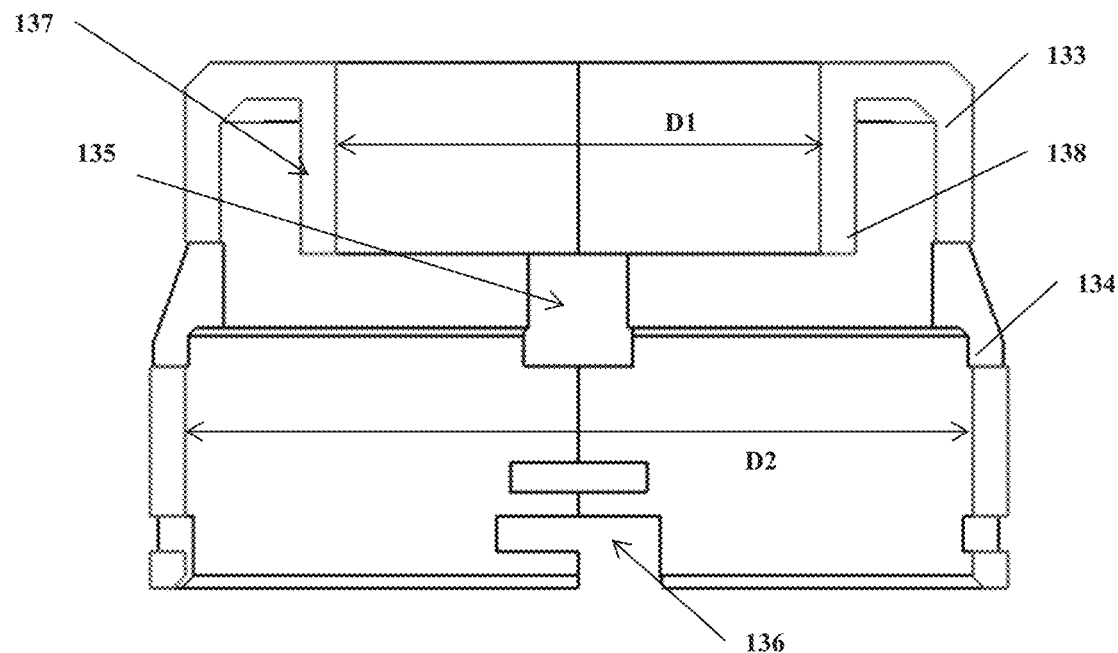
FIG. 3C is a cross-sectional view of the main housing.
Figure 3D:
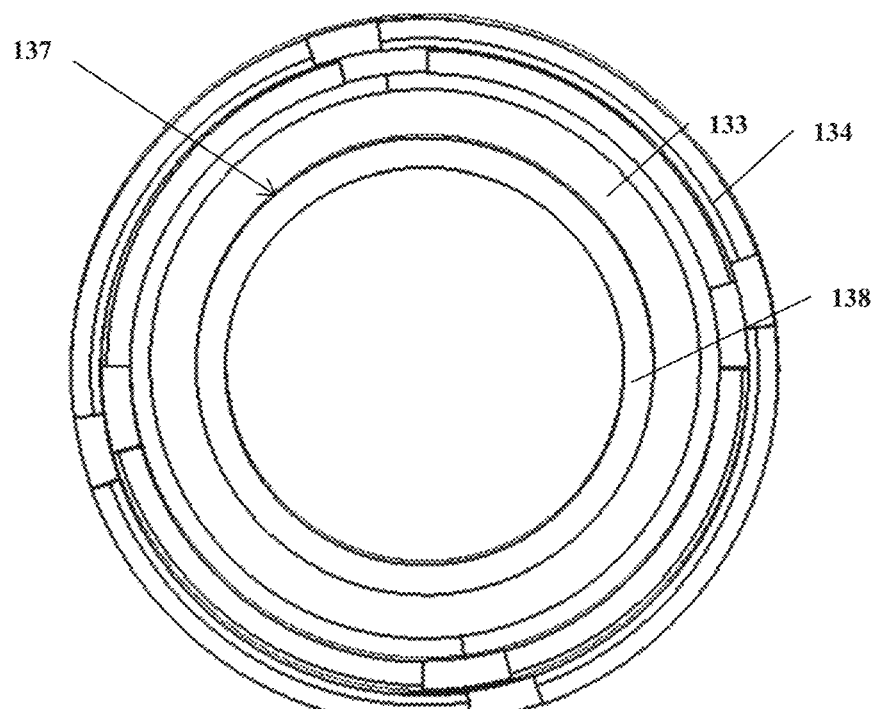
FIG. 3D is a bottom view of the main housing.

As shown in FIG. 3A, the main housing 130 includes a housing lumen 131 disposed within a stepped portion 132 including a first housing member 133, a second housing member 134, and a plurality of openings 135 disposed between the first housing member 133 and the second housing member 134. The second housing member 134 includes a plurality of tab openings 136 disposed on the bottom portion of the second housing member 134. In one embodiment, the plurality of tab openings 136 include a generally L-shape to permit locking of the main housing with the sensor socket 150. The first housing member 133 includes a first diameter D1 and the second housing member 134 includes a second diameter D2, as shown in FIGS. 3B-3C. The first diameter D1 operably couples with the tube connector 140. The first housing member 133 includes an inner annular ring 137, as shown in FIGS. 3C-3D. The second diameter D2 operably couples with the a sensor cover 160, a connector thermistor proximity 170, a battery cover, a force sensor unit 180, a memory circuit 190, an accelerometer 200, a temperature sensor 210, a battery 220, a PCB cap 230, and a battery cover 240. The inner annular ring 137 includes a bottom lipped portion 138, as shown in FIGS. 3C-3D.

Figure 4A:
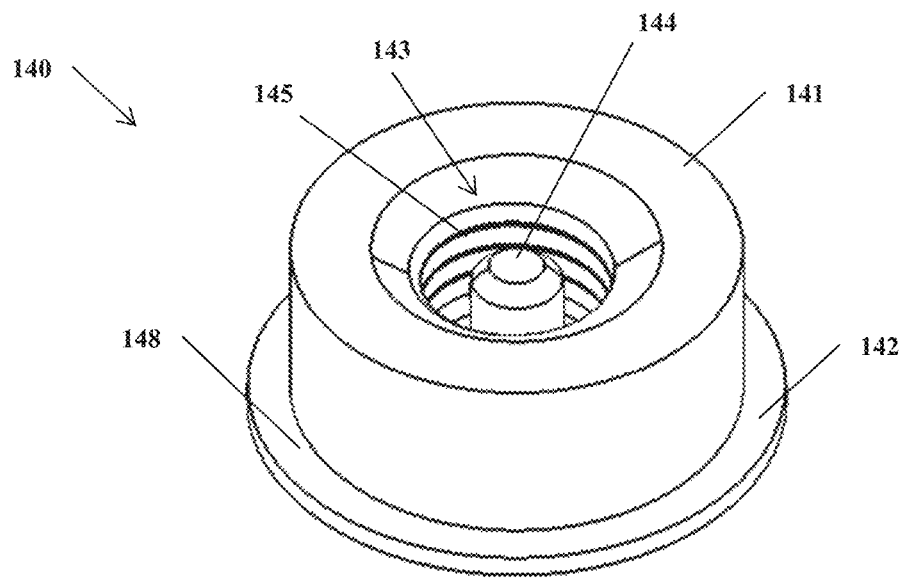
FIG. 4A is a perspective top view of the tube connector.
Figure 4B:
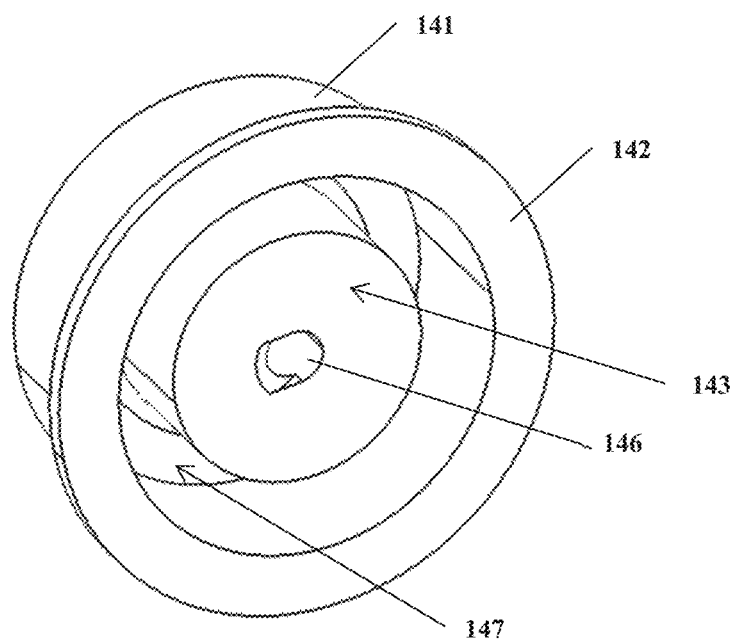
FIG. 4B is a perspective bottom view of the tube connector.
Figure 4C:
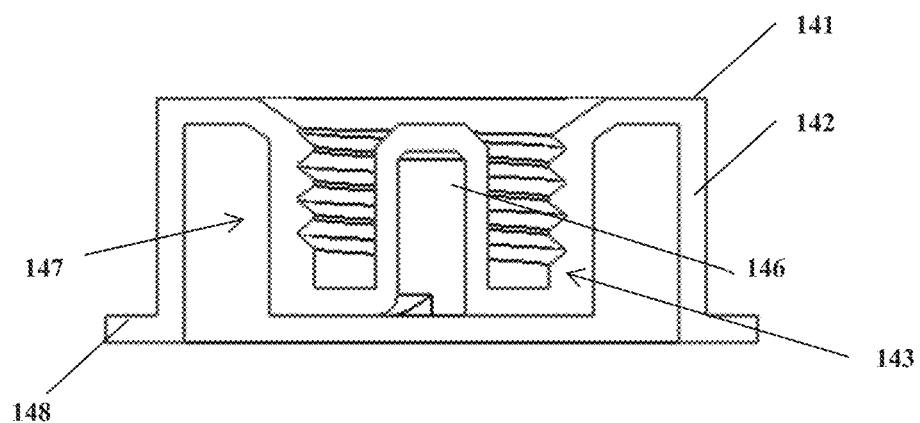
FIG. 4C is a cross-sectional view of the tube connector.
Figure 4D:
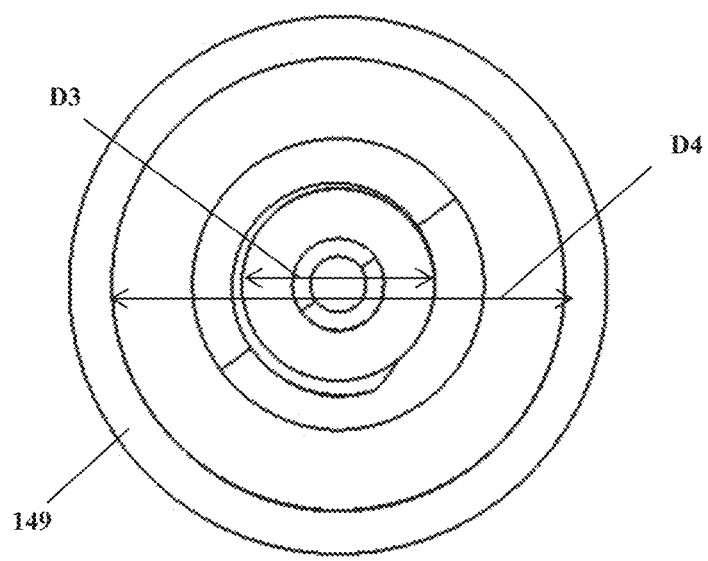
FIG. 4D is a top view of the tube connector.

As shown in FIGS. 4A-4D, the tube connector 140 includes a top connecting portion 141 and a bottom portion 142 with a central tube lumen 143 disposed through the top connecting portion 141 and the bottom portion 142. The central tube lumen 143 includes a hollow central tip 144 and a threaded interior portion 145. As shown in FIG. 4B, the hollow central tip 144 includes a hollow opening 146, and the top connecting portion 141 includes an annular ring 147 disposed around the central tube lumen 143. The hollow central tip 144 operably couples with the temperature sensor 210 and the connector thermistor proximity 170. The threaded interior portion 145 includes a diameter D3 and the annular ring 147 includes a diameter D4, as shown in FIG. 4D. The threaded interior portion 145 operably couples with the top connecting portion of the container 110 as to secure the cap device to the container 110. The diameter D3 is sized to fit the top portion of the container 110. The diameter D4 is sized to fit sensor socket 150 and the annular ring 147 operably couples with sensor socket 150. The central tube lumen 143 includes a bottom portion 148 that operably couples with the sensor cover 160. The bottom portion 142 includes a lip 149 that abuts bottom lipped portion 138 of the inner annular ring 137.

Figure 5A:
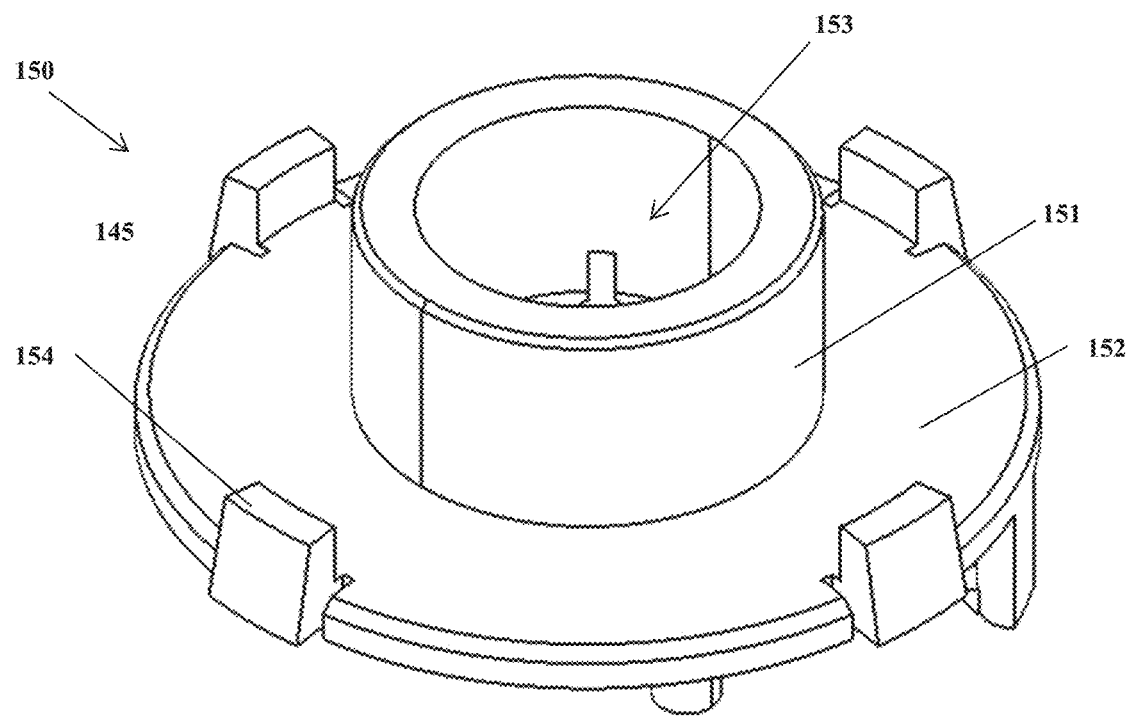
FIG. 5A is a perspective top view of the sensor socket.
Figure 5B:
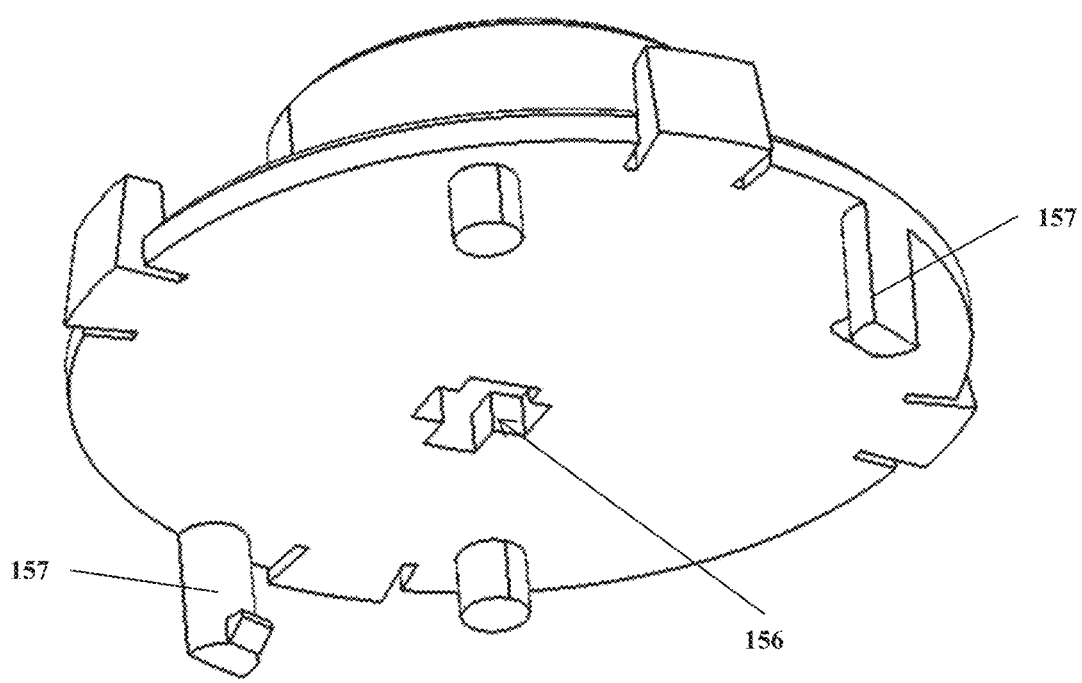
FIG. 5B is a perspective bottom view of the sensor socket.
Figure 5C:
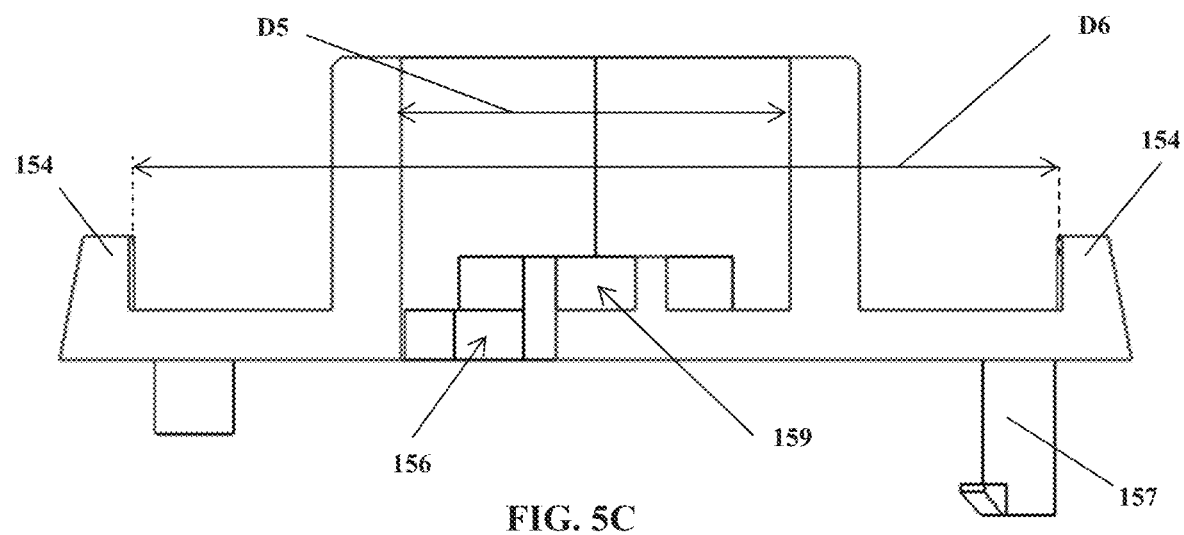
FIG. 5C is a cross-sectional view of the sensor socket.
Figure 5D:
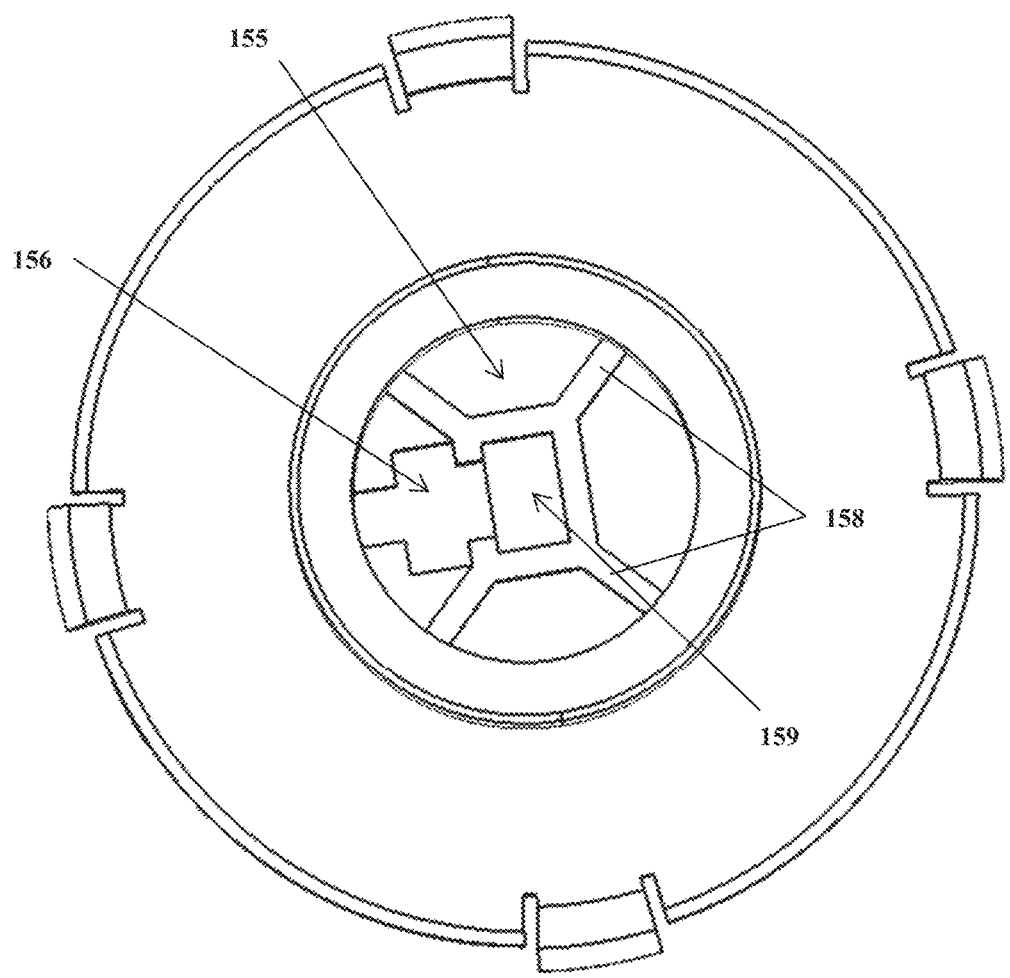
FIG. 5D is a top view of the sensor socket.
Figure 6A:
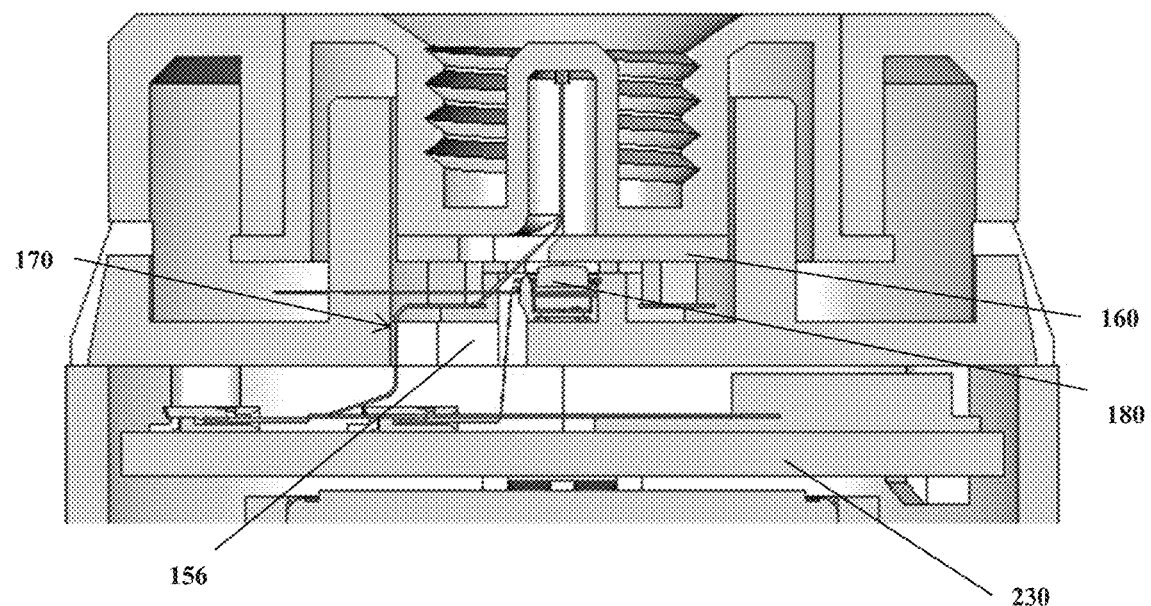
FIG. 6A is cross-sectional view of the cap device with the main housing, tube connector, and sensor socket.
Figure 6B:
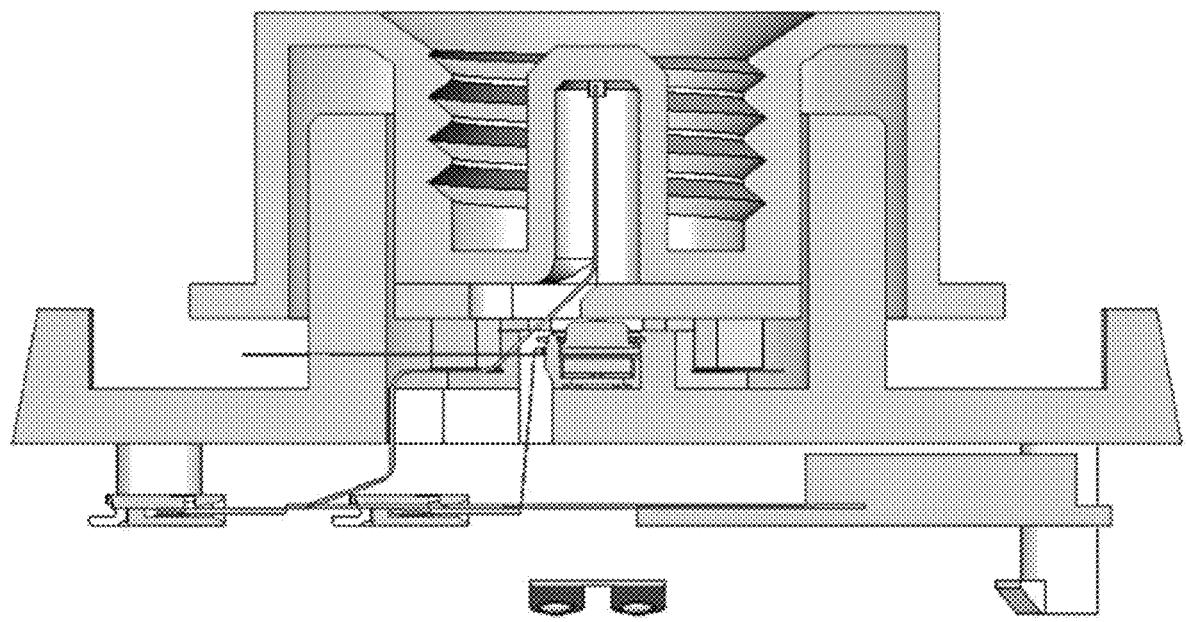
FIG. 6B is a cross-sectional view of the cap device showing the tube connector and the sensor socket with the sensor.

As shown in FIGS. 5A-5D, the sensor socket 150 includes a top socket portion 151 and a bottom socket portion 152. The top socket portion 151 includes an annular lumen 153 and the bottom socket portion 152 includes a plurality of outer tabs 154 on the top surface of the bottom socket portion 152. The annular lumen 153 includes a diameter D5, as shown in FIG. 5C, which operably couples with the diameter D4 of the annular ring 147 of the tube connector 140. The bottom socket portion 152 includes a plurality of lower tabs 157 on the bottom surface of the bottom socket portion 152. The plurality of outer tabs 154 operably couple with the plurality of openings 135 of the main housing 130 as to secure the sensor socket 150 within the main housing 130. As shown in FIG. 5C, the plurality of outer tabs 154 are separated by distance D6 which operably couples with the diameter D2 of the main housing 130. The annular lumen 153 includes a bottom seated portion 155 with a bottom opening 156, as shown in FIG. 5D. The bottom seated portion 155 includes a plurality of sides 158 forming a seat 159 that holds the force sensor unit 180 to sit at the bottom of the annular lumen 153 and abut the sensor cover 160 on top of the force sensor unit 180, as shown in FIG. 6A. In one embodiment, the plurality of sides 158 are generally in an X-formation, although other formations may be used such as a Y formation in other embodiments. The bottom opening 156 is sized to permit the force sensor unit 180 and the connector thermistor proximity 170 to operably couple with the PCB cap 230 and electronics, as shown in FIG. 6A. In one embodiment, the plurality of lower tabs 157 include a generally L-shape as to secure the PCB cap 230, although other shapes may be used.

Figure 7A:
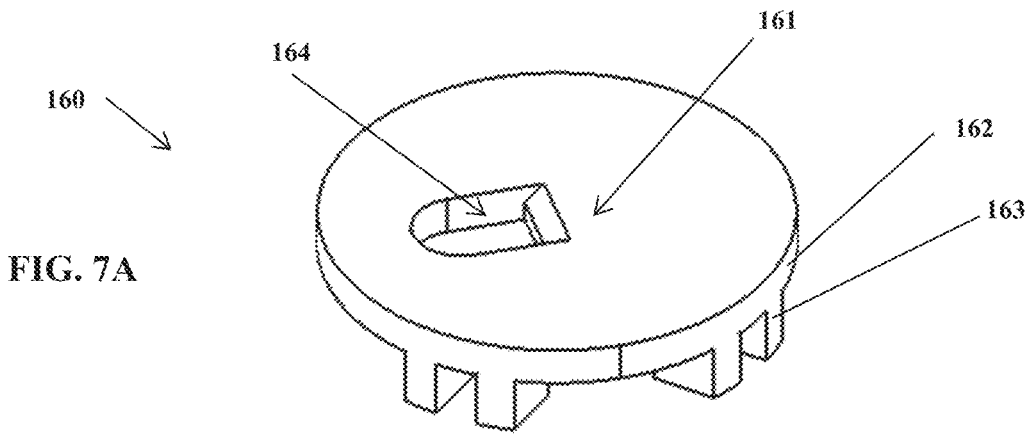
FIG. 7A is a perspective top view of the sensor cover.
Figure 7B:
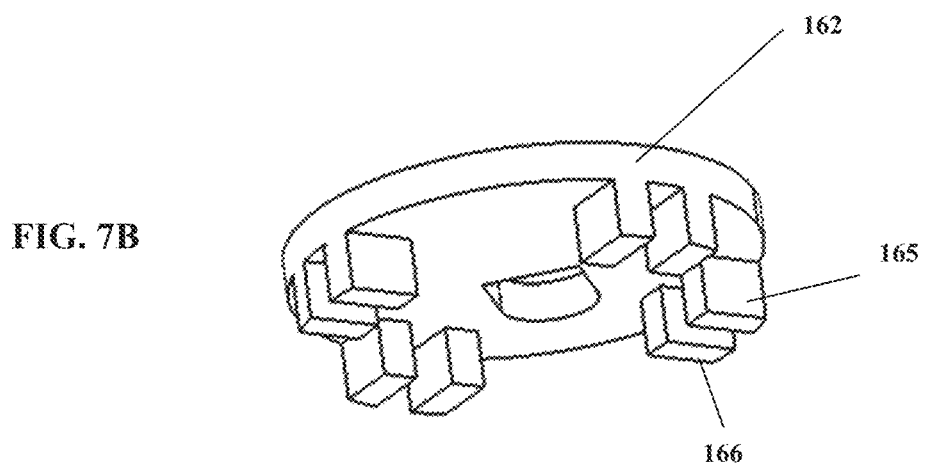
FIG. 7B is a perspective bottom view of the sensor cover.
Figure 7C:
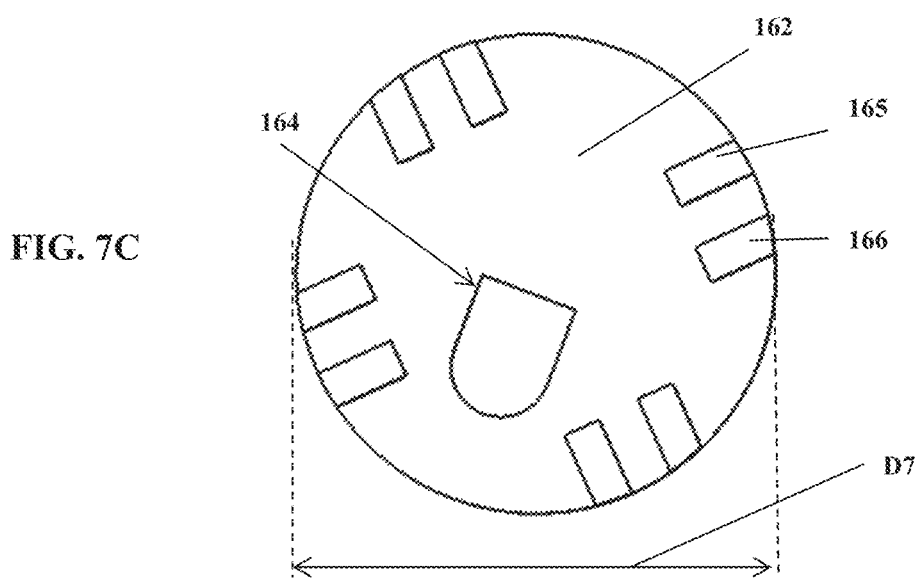
FIG. 7C is a bottom view of the sensor cover.

As shown in FIG. 7A-7C, the sensor cover 160 includes a top sensor cover 161 and a bottom sensor cover 162. The bottom sensor cover 162 includes a plurality of holders 163 and the top sensor cover 161 includes a sensor opening 164 traversing the top and bottom sensor covers. The plurality of holders 163 include a first side 165 and a second side 166 sized to receive the plurality of sides 158 of the bottom seated portion 155. The plurality of sides 158 are generally in opposed and align with the X shape formation of the plurality of sides 158 of the sensor socket 150. The sensor cover 160 includes a diameter D8 which aligns with the diameter D5 of the sensor socket 150 and the annular lumen 153. The sensor opening 164 is sized to permit the connector thermistor proximity 170 and operably couple the force sensor unit 180, as shown in FIGS. 8A-8D.

Figure 8A:
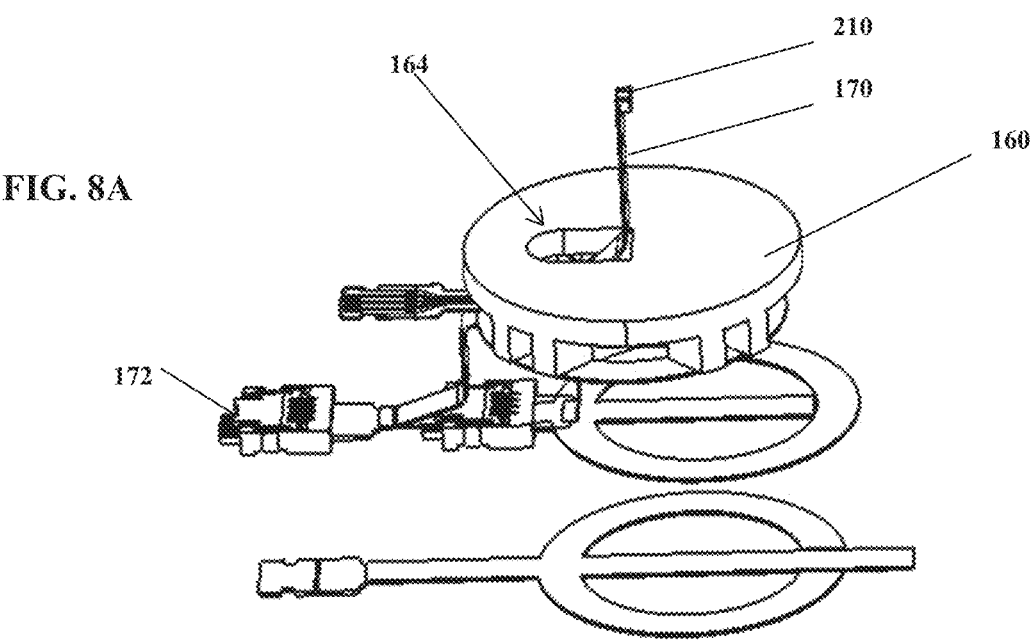
FIG. 8A is a perspective top view of the sensor cover with the force sensor and the thermistor proximity connector.
Figure 8B:
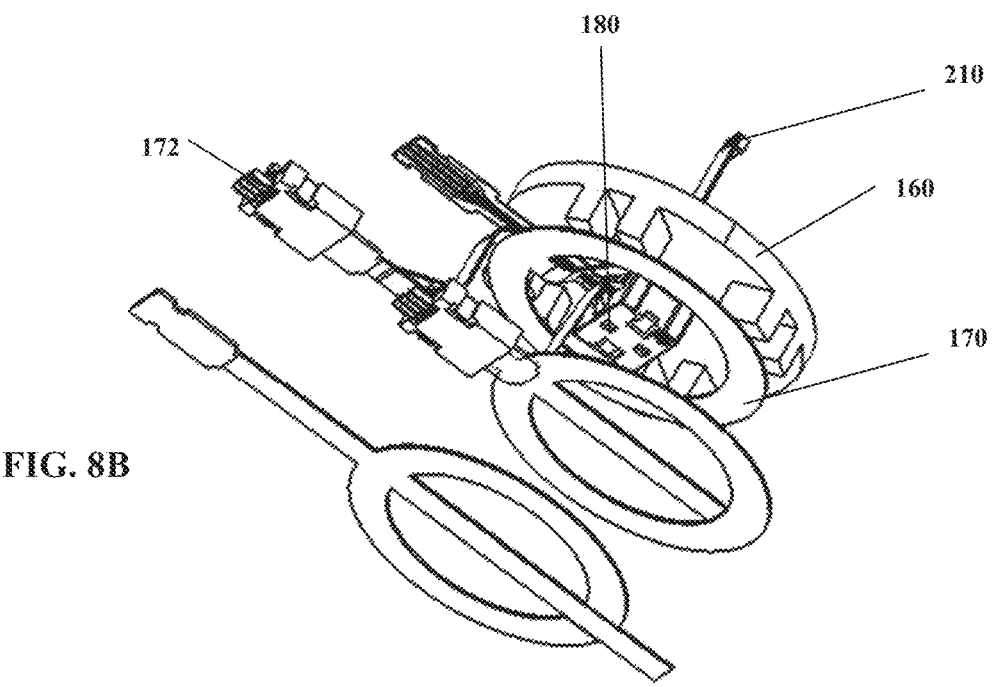
FIG. 8B is a perspective bottom view of the sensor cover with the force sensor and the thermistor proximity connector.
Figure 8C:
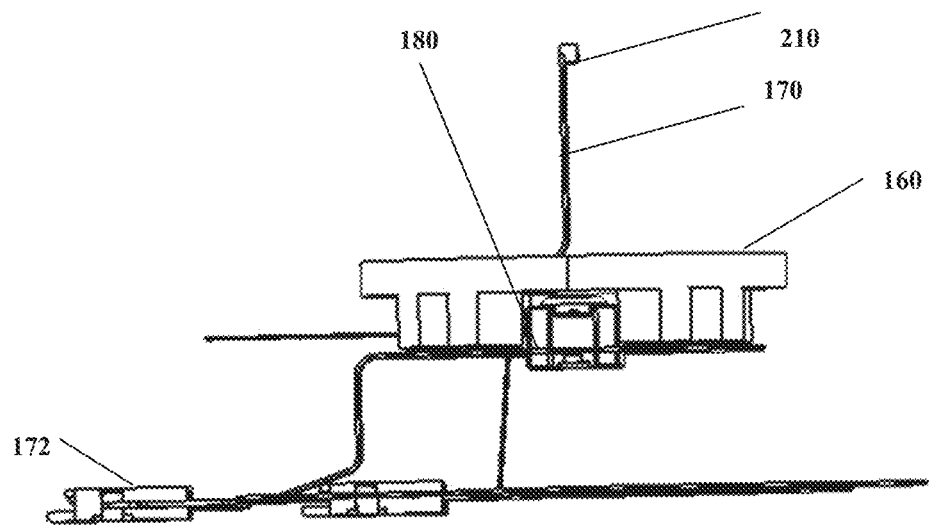
FIG. 8C is a side view of the sensor cover with the force sensor and the thermistor proximity connector.
Figure 8D:
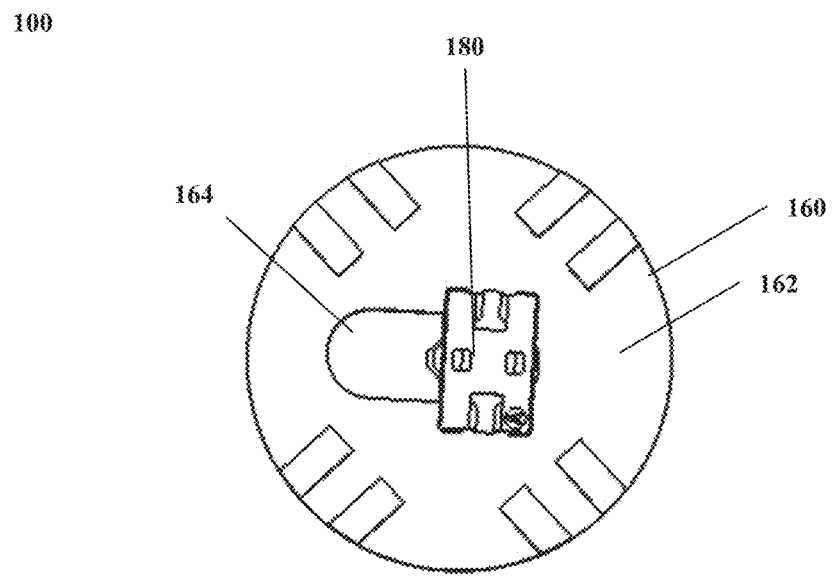
FIG. 8D is a bottom view of the sensor cover with the force sensor.

As shown in FIGS. 8A-8C, the sensor cover 160 operably couples the connector thermistor proximity 170 and the force sensor unit 180. The force sensor unit 180 is disposed on the bottom sensor cover 162 and the sensor opening 164, as shown in FIG. 8D. The connector thermistor proximity 170 connects to the temperature sensor 210 and the force sensor unit 180. In one embodiment, the connector thermistor proximity 170 operably couples with end terminal regions 172.

Figure 9A:
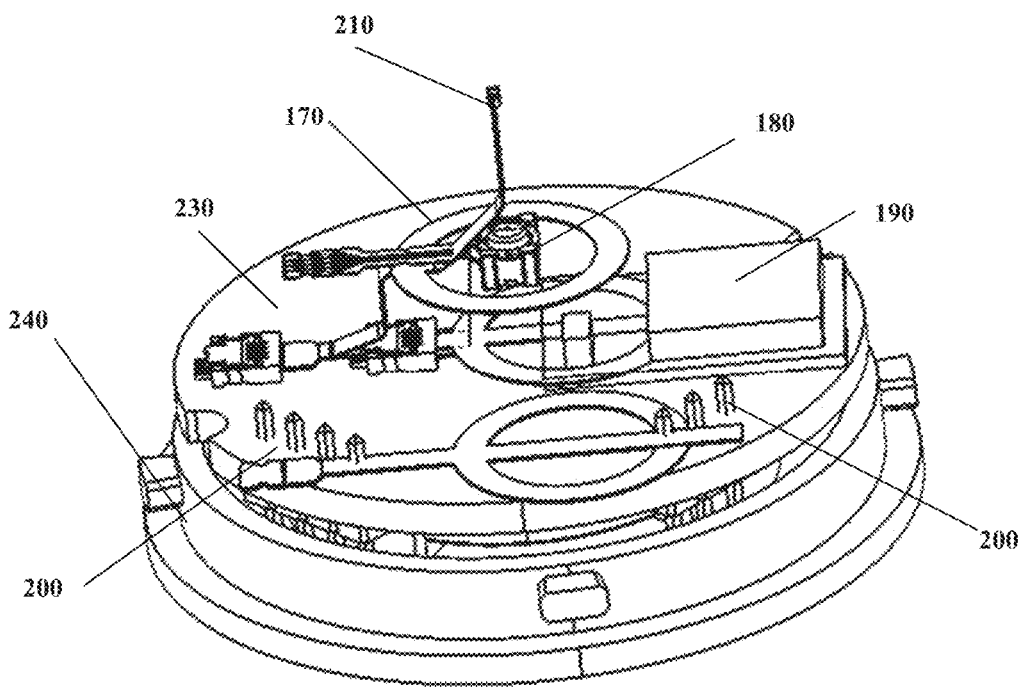
FIG. 9A is a perspective top view of the PCB cap coupled with the thermistor proximity connector, the force motion unit, the temperature sensor, and the battery cover.
Figure 9B:
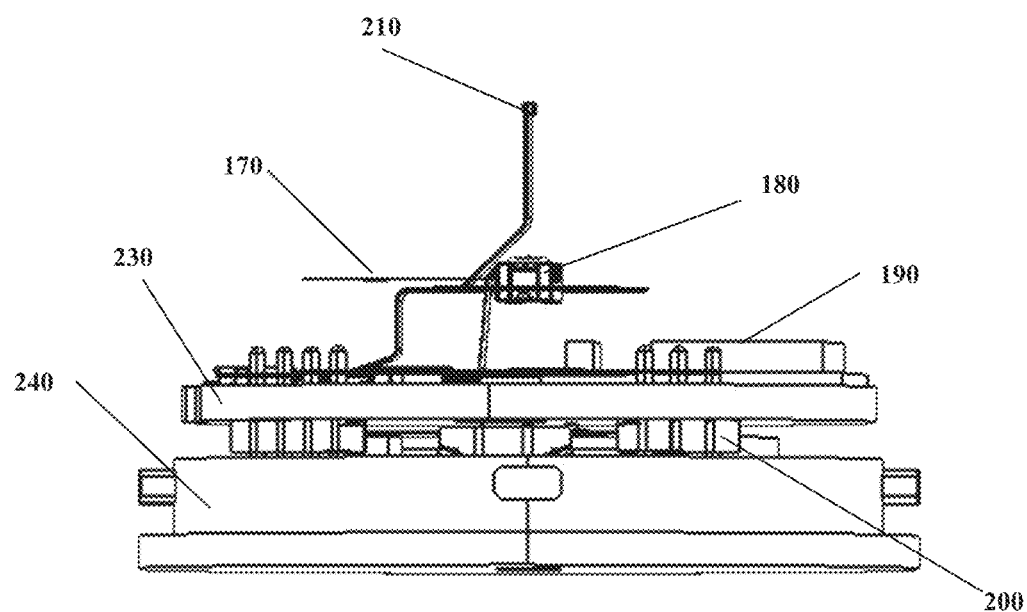
FIG. 9B is a side view of the PCB cap coupled with the thermistor proximity connector, the force motion unit, the temperature sensor, and the battery cover.
Figure 9C:
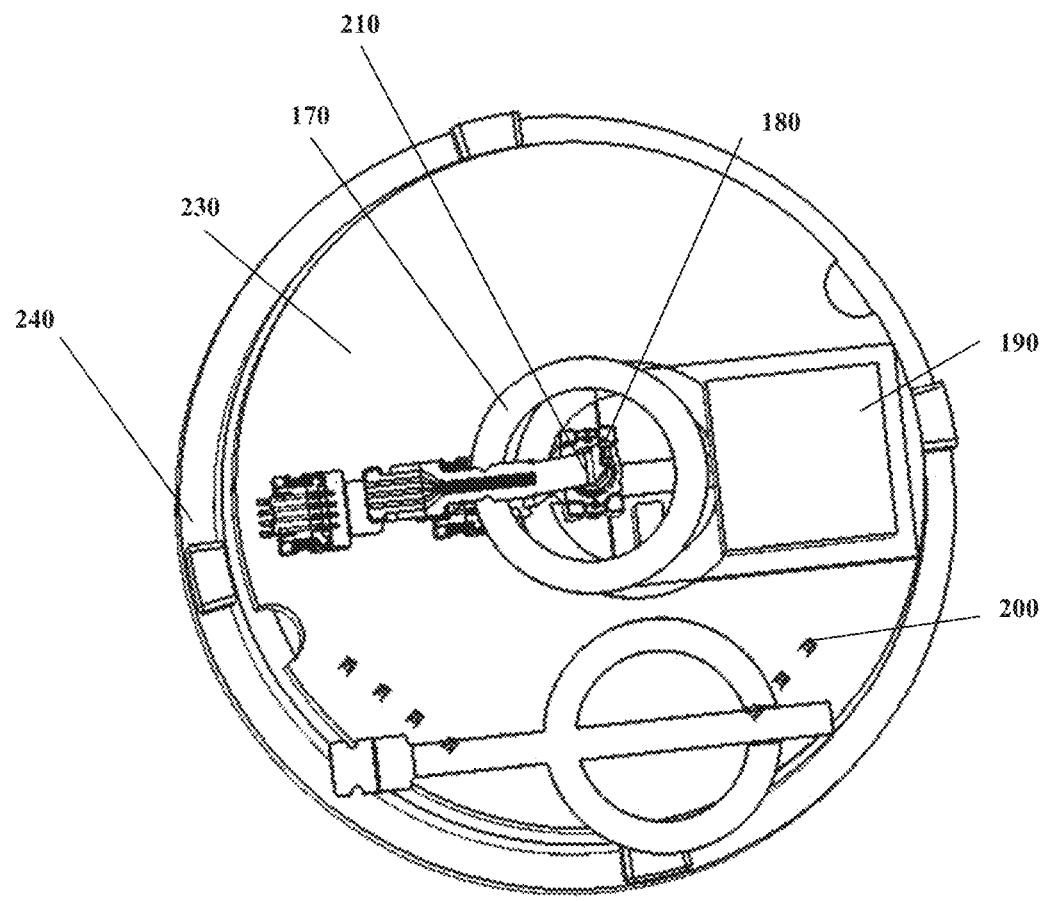
FIG. 9C is a top view of the PCB cap coupled with the thermistor proximity connector, the force motion unit, the temperature sensor, and the battery cover.

As shown in FIGS. 9A-9C, the PCB cap 230 is shown including the connector thermistor proximity 170 disposed on the PCB cap, the force sensor unit 180 operably coupled with the connector thermistor proximity 170, the temperature sensor 210 operably coupled with the connector thermistor proximity 170, the memory circuit 190 disposed on the PCB cap 230, and the accelerometer 200 disposed through the PCB cap 230.

Figure 10A:
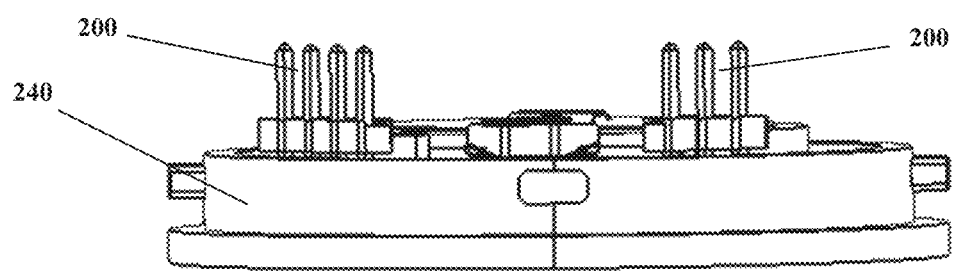
FIG. 10A is a side view of the accelerometers coupled with the battery cover.
Figure 10B:
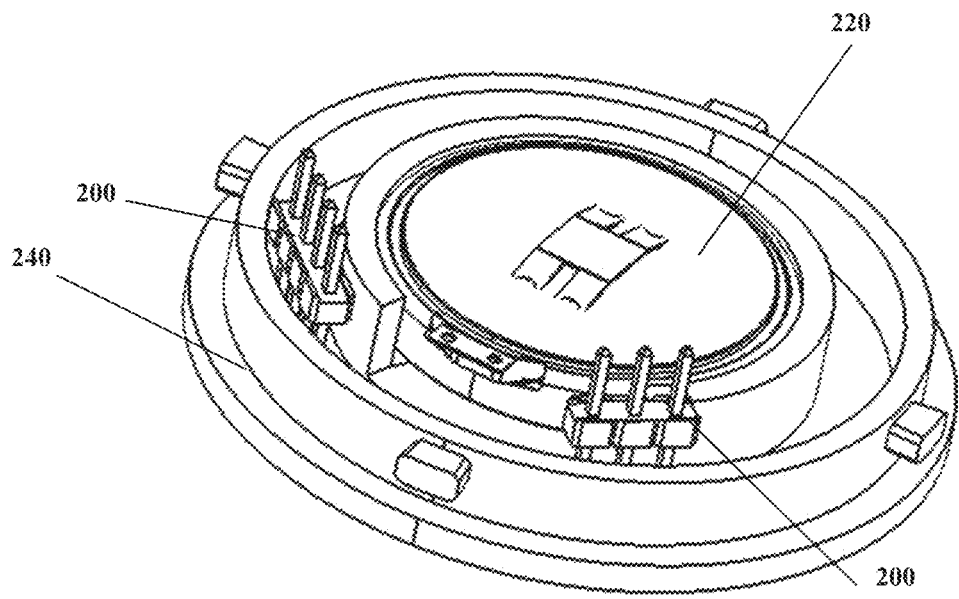
FIG. 10B is a top perspective view of the battery and accelerometers coupled with the battery cover.
Figure 10C:
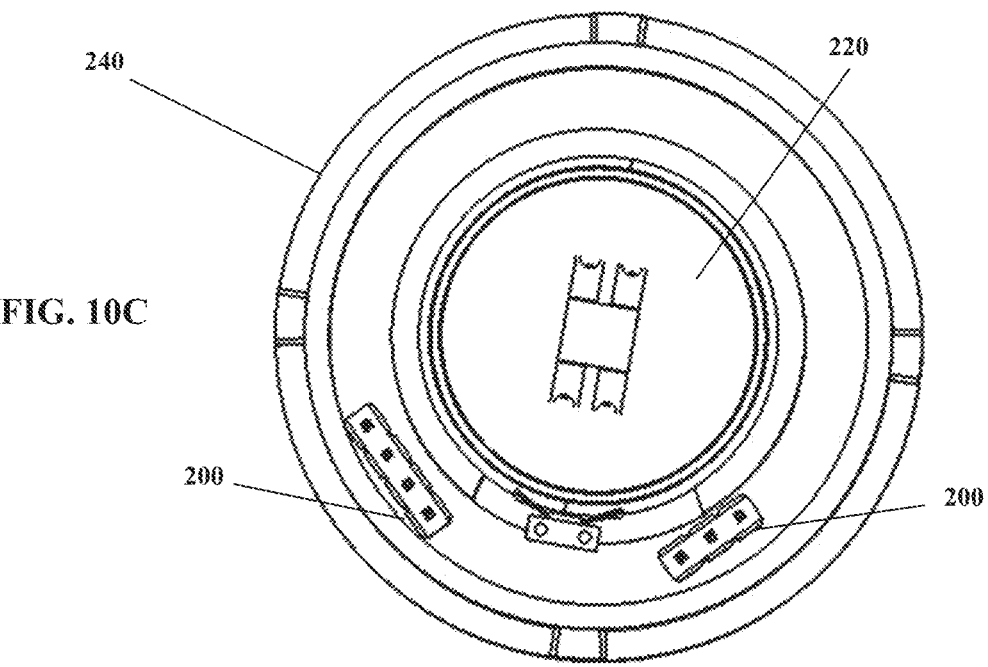
FIG. 10C is a top view of the battery and accelerometers coupled with the battery cover.

As shown in FIG. 10A-10C, the accelerometers 200 are operably coupled with the battery cover 240 and are situated below the PCB cap 230.

Figure 11A:
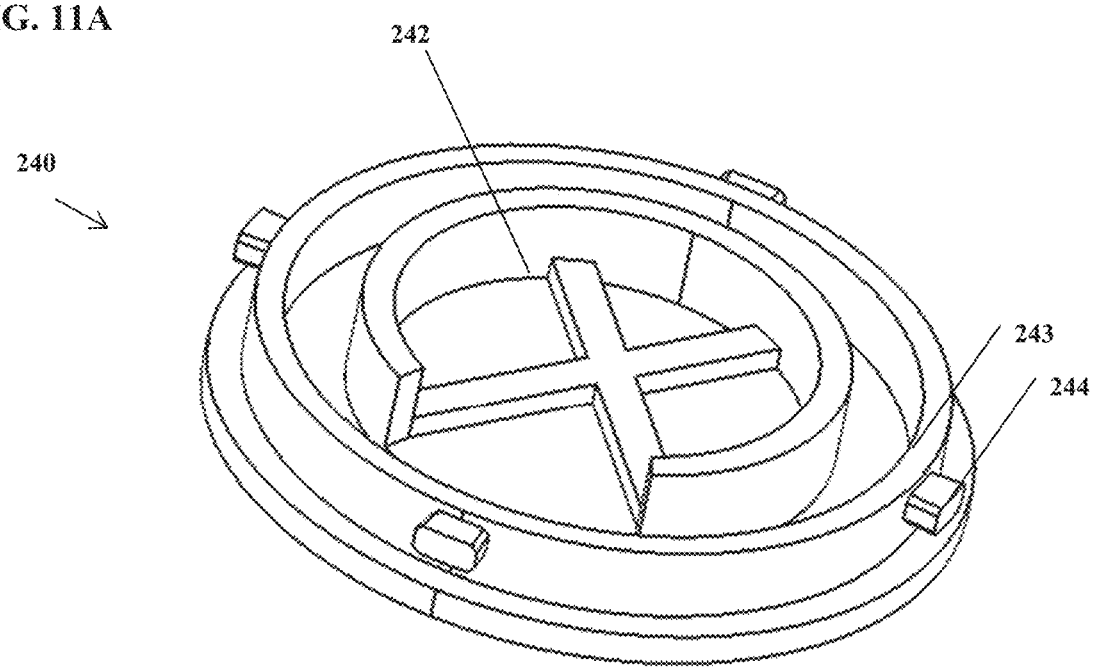
FIG. 11A is a perspective top view of the battery cover.
Figure 11B:
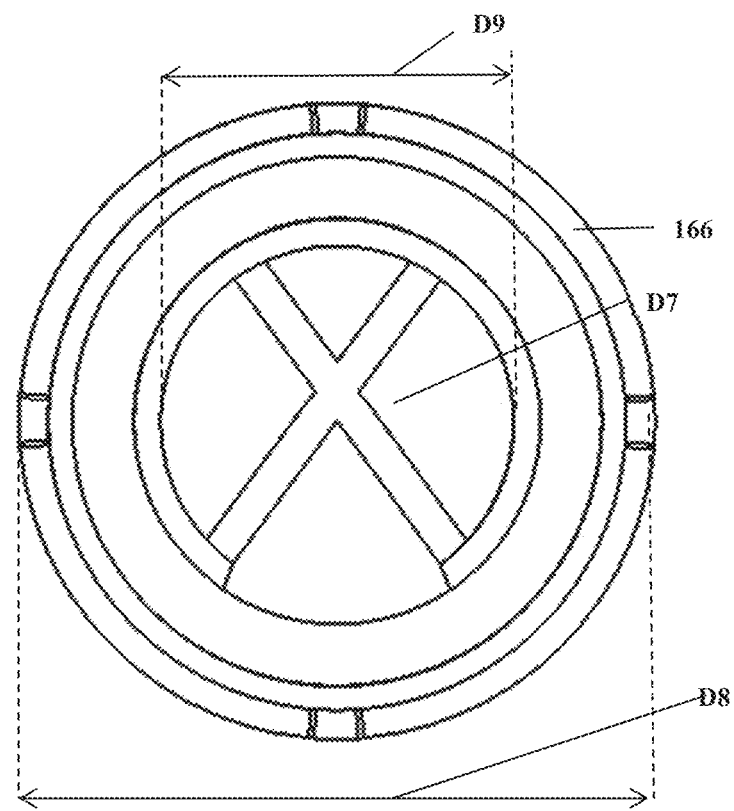
FIG. 11B is a top view of the battery cover.

As shown in FIGS. 11A-11B, the battery 220 is disposed within the battery cover 240. The battery cover 240 includes a central holding portion 242 disposed in the center and an outer annular ring 243. The outer annular ring 243 includes a plurality of tabs 244. The plurality of tabs 244 are separated by a diameter D8, which aligns with diameter D2 of the main housing and couple with the plurality tab openings 136. The central holding portion 242 includes a diameter D9 to operably couple with the battery 220.

Figure 12A:
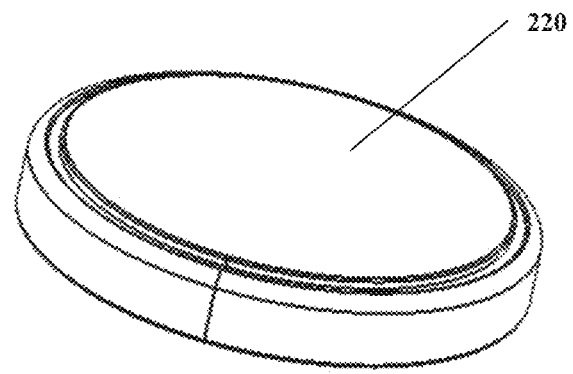
FIG. 12A is a top perspective view of the battery.
Figure 12B:
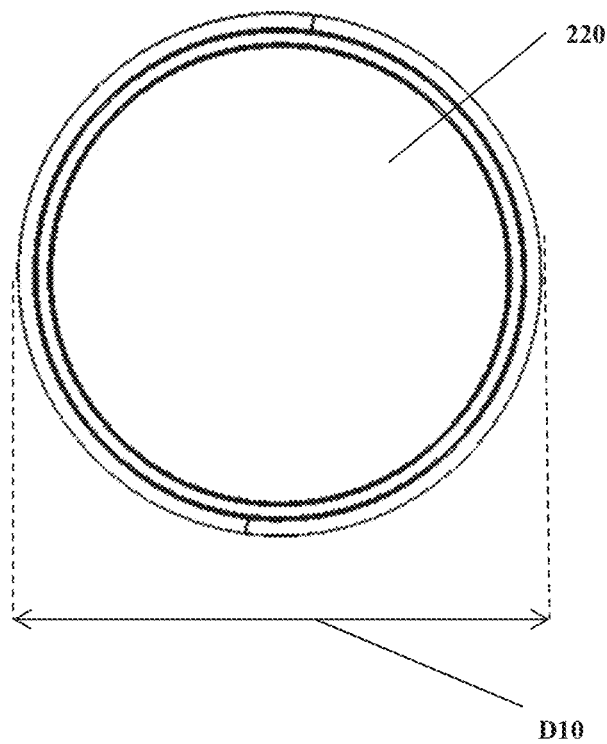
FIG. 12B is a top view of the battery.

As shown in FIGS. 12A-12B, the battery 220 includes a diameter D10 which aligns with the diameter D9 of the batter cover 240.

Figure 13:
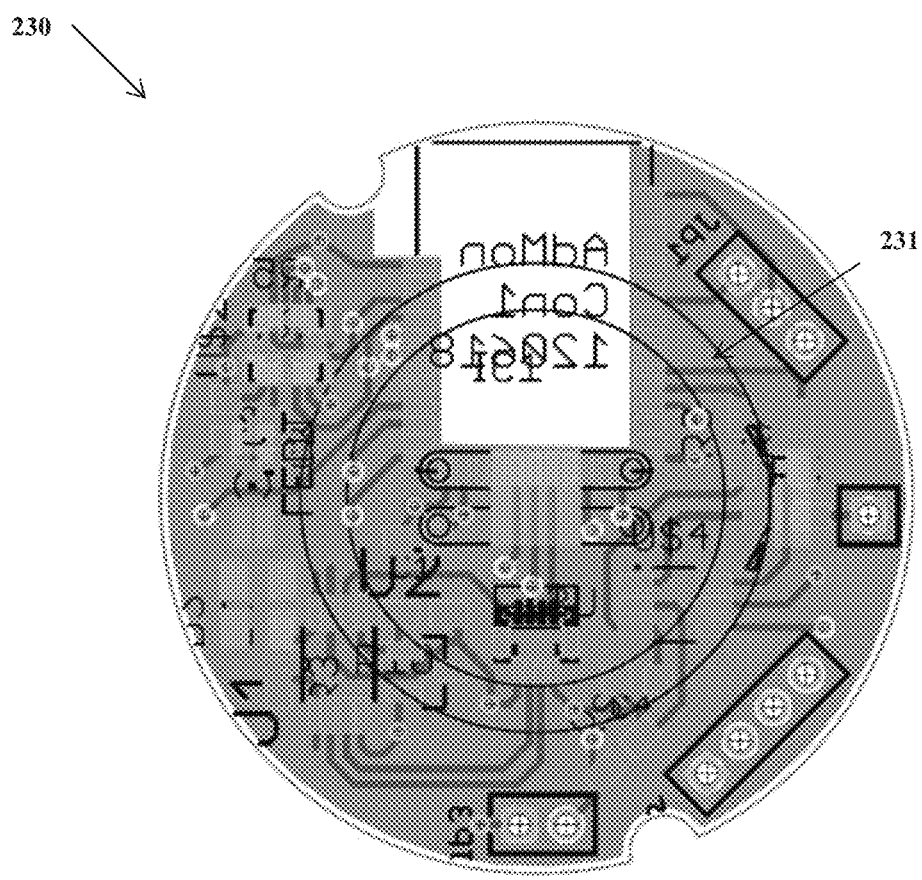
FIG. 13 is a top view of the PCB cap with the printed circuitry.

As shown in FIG. 13, the PCB cap 230 includes circuitry 231 for input and control of the temperature sensor 210, the force sensor unit 180, the connector thermistor proximity 170, the accelerometer 200, and the memory circuit 190.

Figure 14:
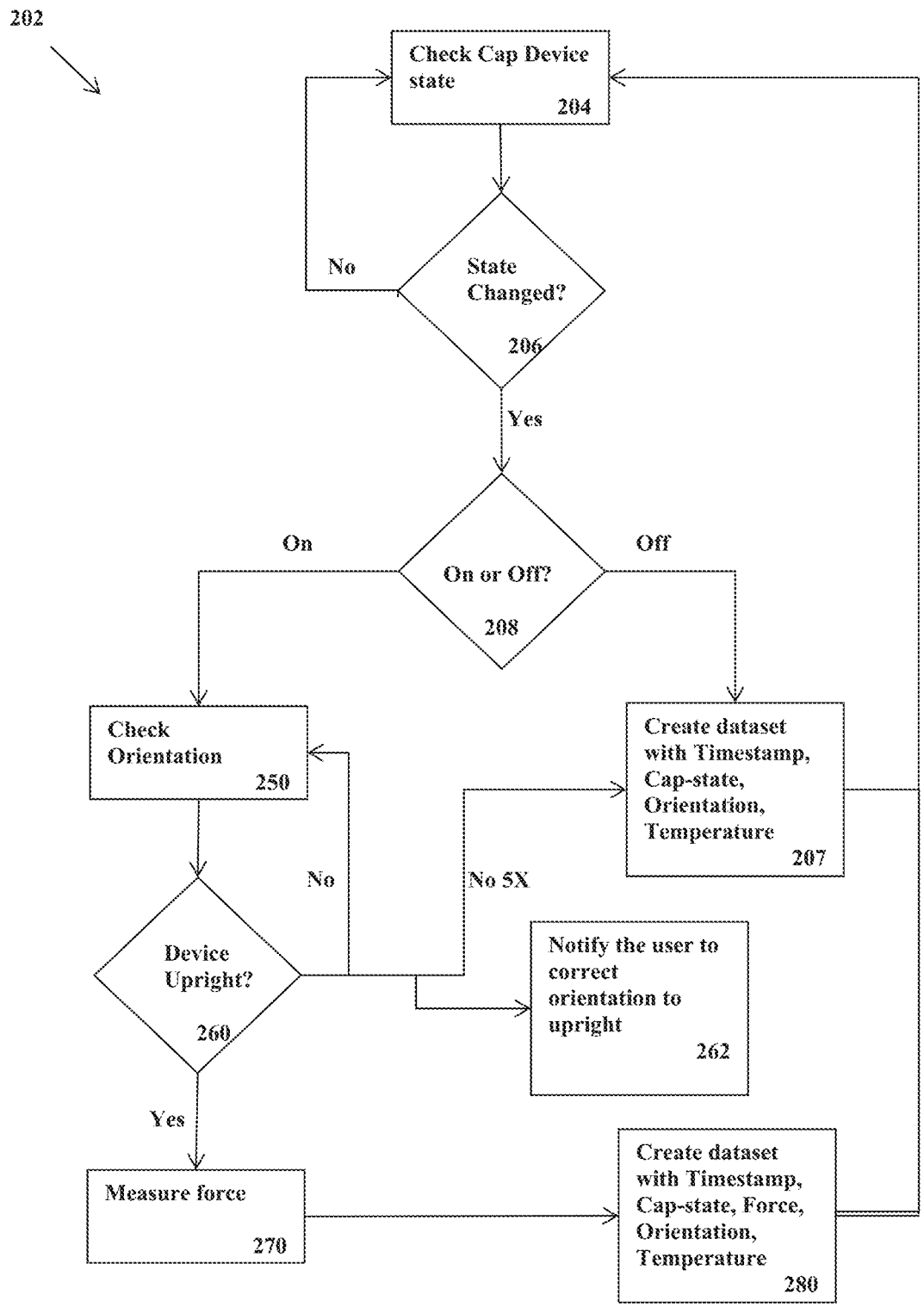
FIG. 14 is a flow chart of one embodiment of the medication adherence system.

As shown in FIG. 14, the procedure for acquisition 202 starts with checking the cap device state 204. If the state of the cap device has changed in step 206, then the cap device determines if it's on or off the container element 208. If the cap device is off, then the cap device creates a dataset with a timestamp, a state of the cap device, the orientation of the cap device, and a temperature of the cap device in step 207. If the cap device is on, then the cap device checks the orientation in step 250. After step 250, the cap device in step 260 to check the orientation of the cap device and determines if the cap device is upright along the axial direction.

If the cap device is not upright, the procedure reverts back to step 250 to check the orientation of the cap device and notifies the user to correct the orientation in step 262. If the cap device is not upright after checking the orientation at least 5 times, then step 207 creates a dataset with a timestamp, a state of the cap device, the orientation of the cap device, and a temperature of the cap device. If the cap device is upright, the step 270 measures the force of the container element. Then step 280 creates a dataset with a timestamp, a state of the cap device, the orientation of the cap device, and a temperature of the cap device. Both step 207 and step 280 proceed back to step 204 to check the cap device state.

Figure 15A:
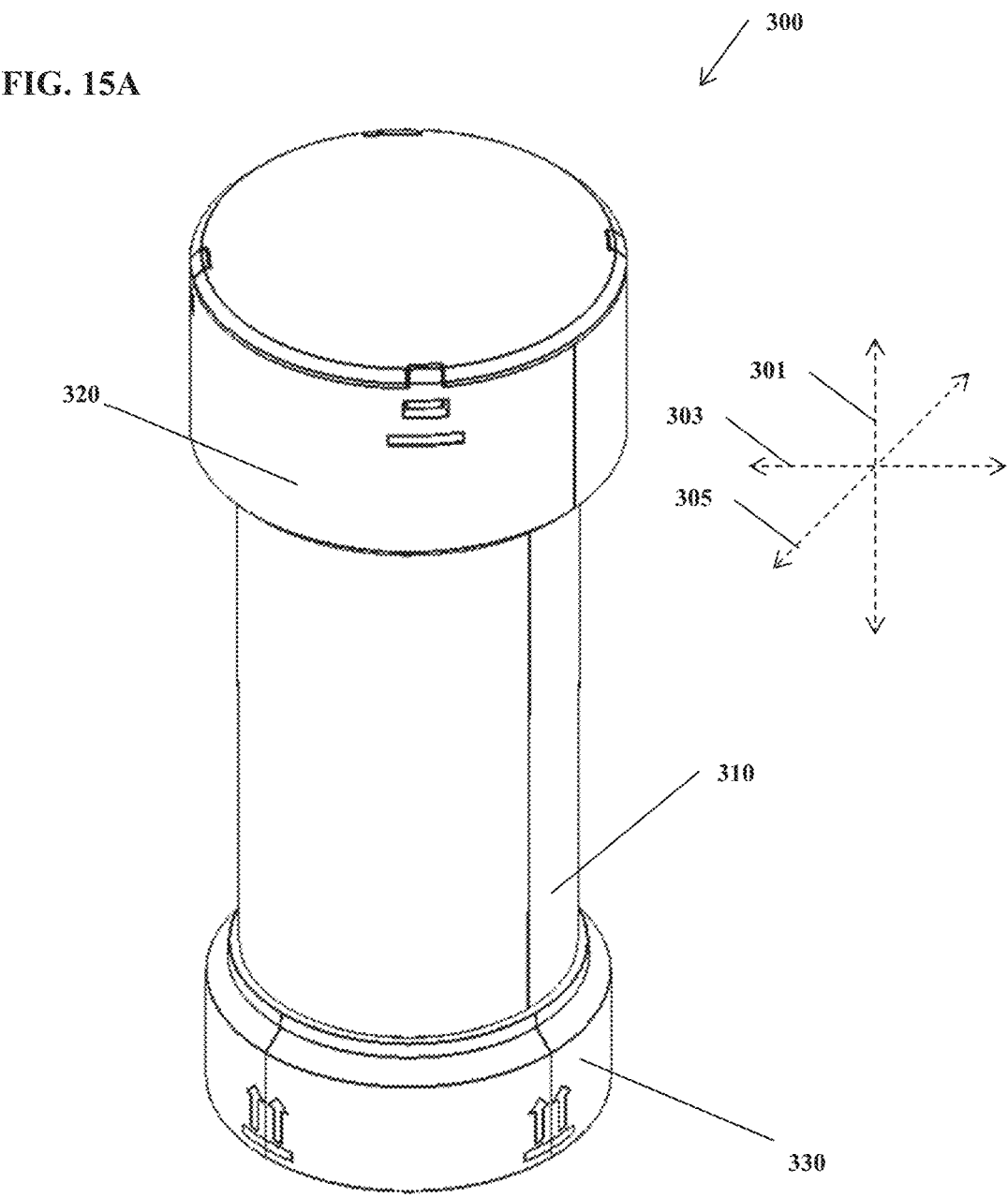
FIG. 15A a perspective view of an alternative embodiment of the medication adherence apparatus.

An alternative embodiment of the medication adherence apparatus 300 is shown in FIG. 15A. The medication adherence apparatus 300 comprises a container element 310 and a first cap device 320 and a second cap device 330, as shown in FIG. 15A. The container element 310 may be any container element to house a medication, such as an ointment tube, wide-mouthed plastic jar, or a platform developed for storage, display, and utilization of medicament container such as a tube, pill bottle, balm jar or tray. The medication may be any type of medication, either in pill, powder, liquid, or gas form. The cap state comprises the force or weight of the container element, the orientation of the first cap device 320 or second cap device 330, the temperature of the first cap device 320 or second cap device 330, and the time stamp including the day, time, and date. The force or weight of the container element 310 is obtained when the container element 310 is inserted into the first cap device 320 or the second cap device 330. The temperature inside the mouth of the container element 310 is obtained by the first cap device 320 or second cap device 330. The presence or absence of the container element 310 in the first cap device 320 is detected by the first cap device 320. The orientation of the first cap device 320 or second cap device 330 is detected to determine if the first cap device 320 or second cap device 330 and/or the container element 110 is upright, which is generally along the vertical axis 301. And any movements of the first cap device 320 or second cap device 330 may be detected, such as along the vertical axis 301, the longitudinal axis 303, or the lateral axis 305. The second cap device 330 detects the weight of the container element 310. The first cap device 320 or second cap device 330 receives a medication schedule and notification parameters to notify a patient by an alarm if medication is missed. The alarm may be an audio sound, a visual notification, an electronic notification, or a cell phone notification.

Figure 15B:
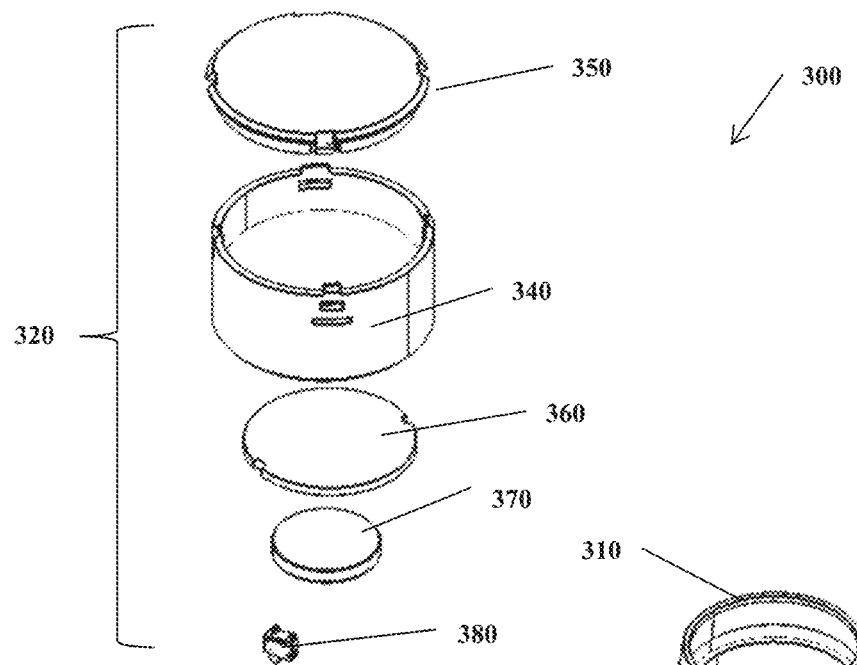
FIG. 15B is an exploded view of the first cap device and second cap device, according to one embodiment.
Figure 15B:
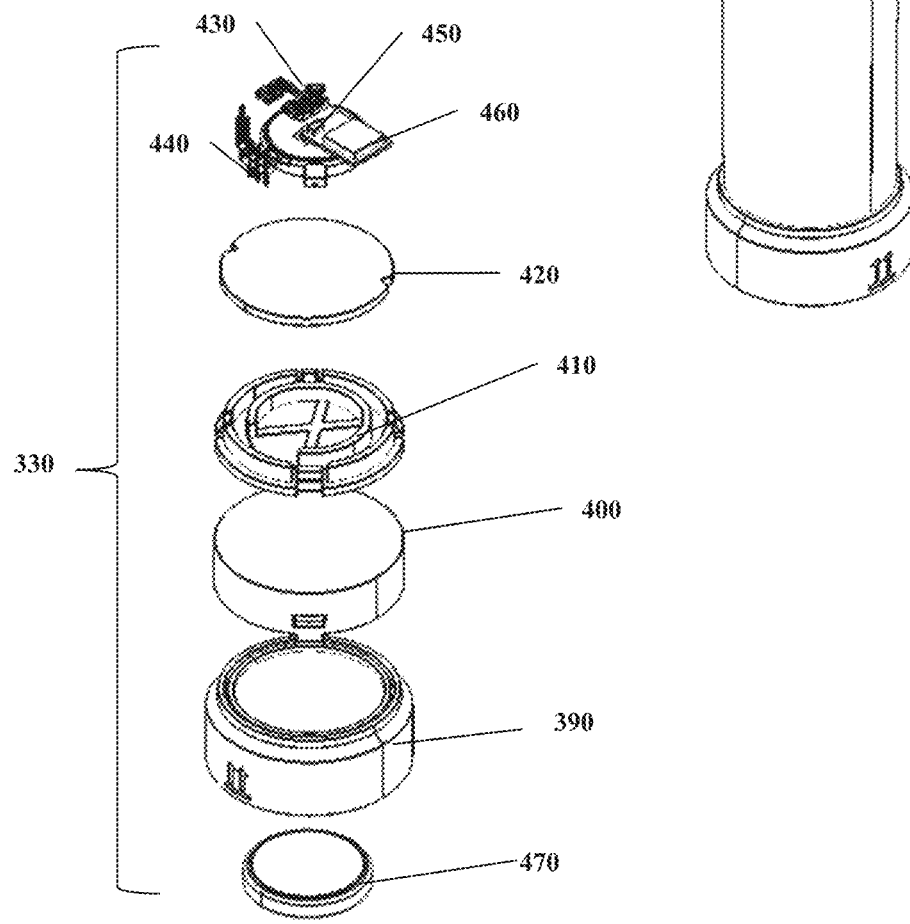

As shown in FIG. 15B, the medication adherence apparatus 300 and the components of the first cap device 320 and the second cap device 330. The first cap device 320 includes a first main housing 340, a first battery cover 350, a first PCB cap 360, a first battery 370, and a detector switch 380. The second cap device 330 includes a bottom connector 390, a second battery 470, a bottom sensor socket 400, a second battery cover 410, a second PCB cap 420, a force sensor 430, an accelerometer 440, a wireless module 450, and a memory circuit card 460.

Figure 15C:
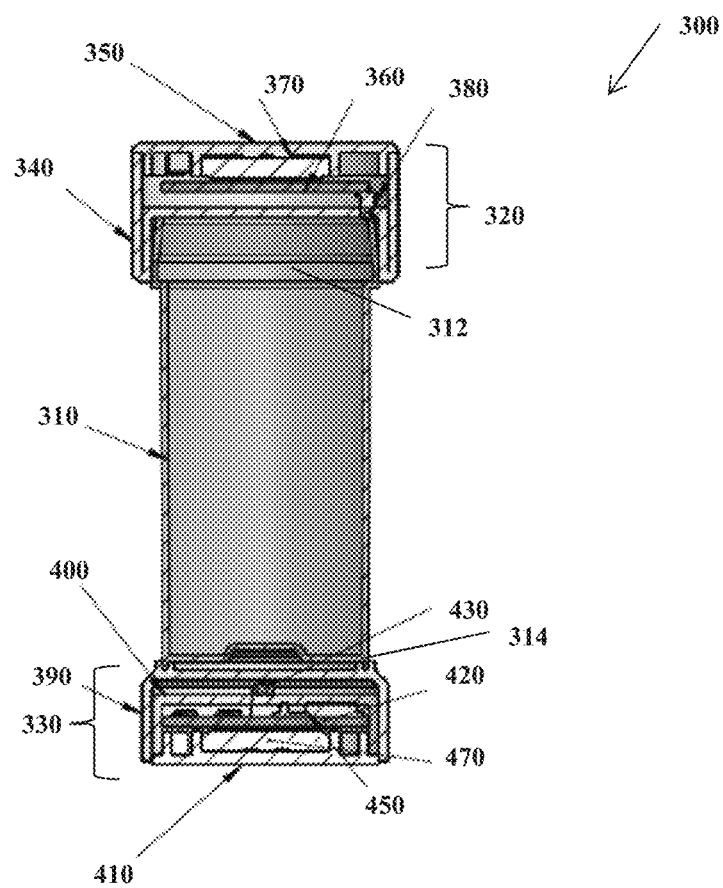
FIG. 15C is a cross sectional view of the medication adherence apparatus from FIG. 15A.
Figure 15D:
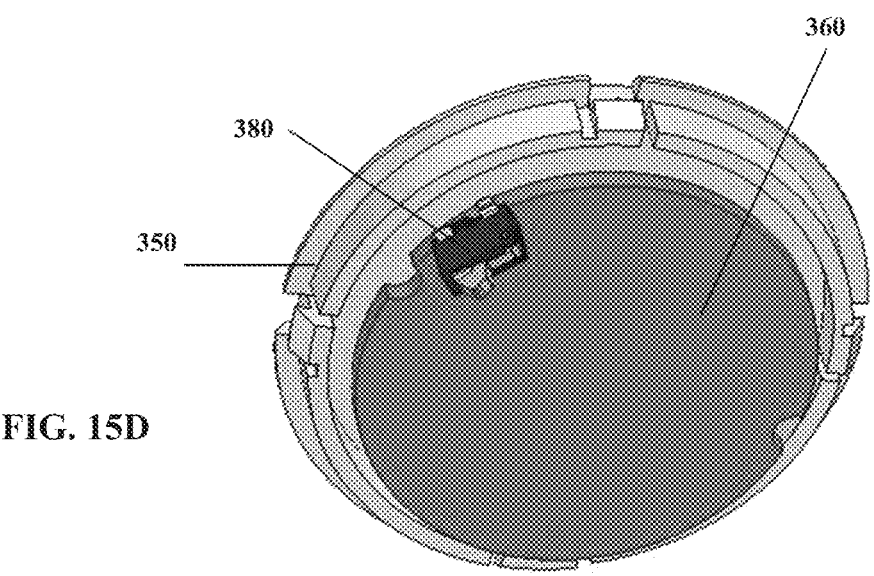
FIG. 15D is a perspective bottom view of the first battery cover.

As shown in FIG. 15C, the first battery cover 350 is operably disposed over the first main housing 340 and the first battery 370 to enclose the top portion of the first cap device 320. The first main housing 340 secures the first cap device 320 to the container element 310 by way of a threaded connection or capped connection 312 on the top end of the container element 310. The first battery 370 is operably disposed over the first PCB cap 360 and the detector switch 380 is operably coupled with the PCB cap 360 as to detect the movement and connection of the first cap device 320 to the container element 310. The detection signal is sent to remote module to notify the user if the first cap device 320 is secured to the container element 310 and notifies a program or module every time the first cap device 320 is removed or secured to the container element 310. The first battery cover 350 may include a snap fit connection to secure to the first main housing 340, as shown in FIG. 15D.

As shown in FIG. 15C, the bottom end 314 of the container element 310 is operably secured on the bottom connector 390. The bottom connector 390 may be altered such that different types of container elements 310 may be secured with the second cap device 330. The force sensor 430 is operably disposed under the top portion of the bottom connector 390 as to detect the force or weight of the container element 310 secured into the second cap device 330.

Figure 15E:
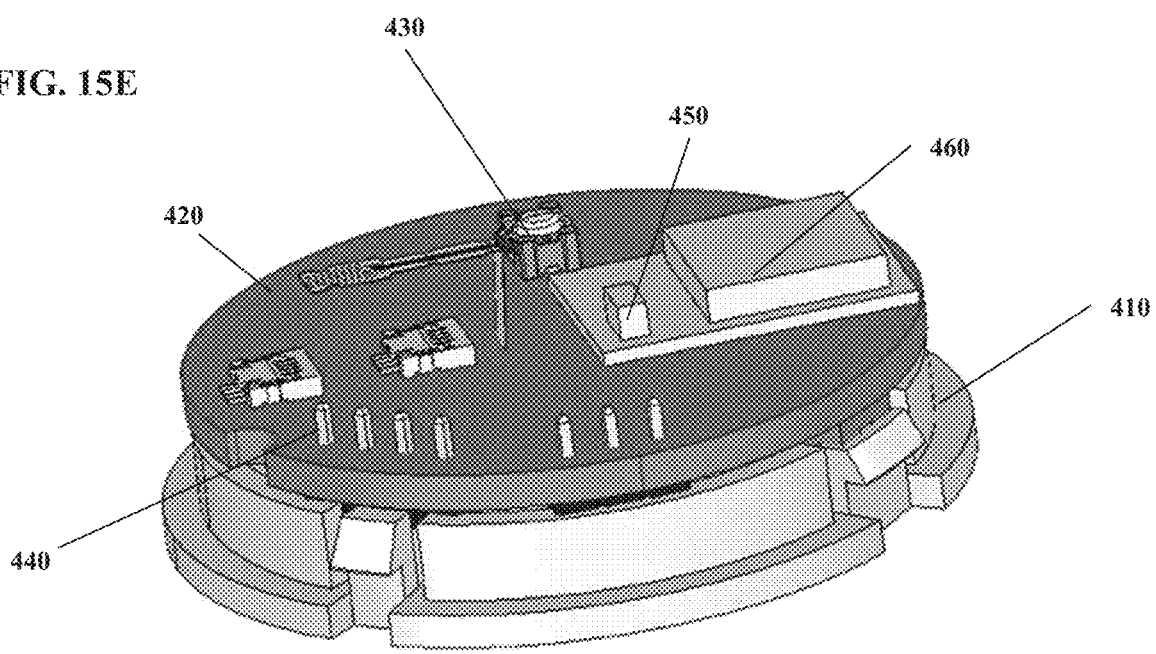
FIG. 15E is a perspective top view of the second battery cover and the second PCB cap.
Figure 15F:
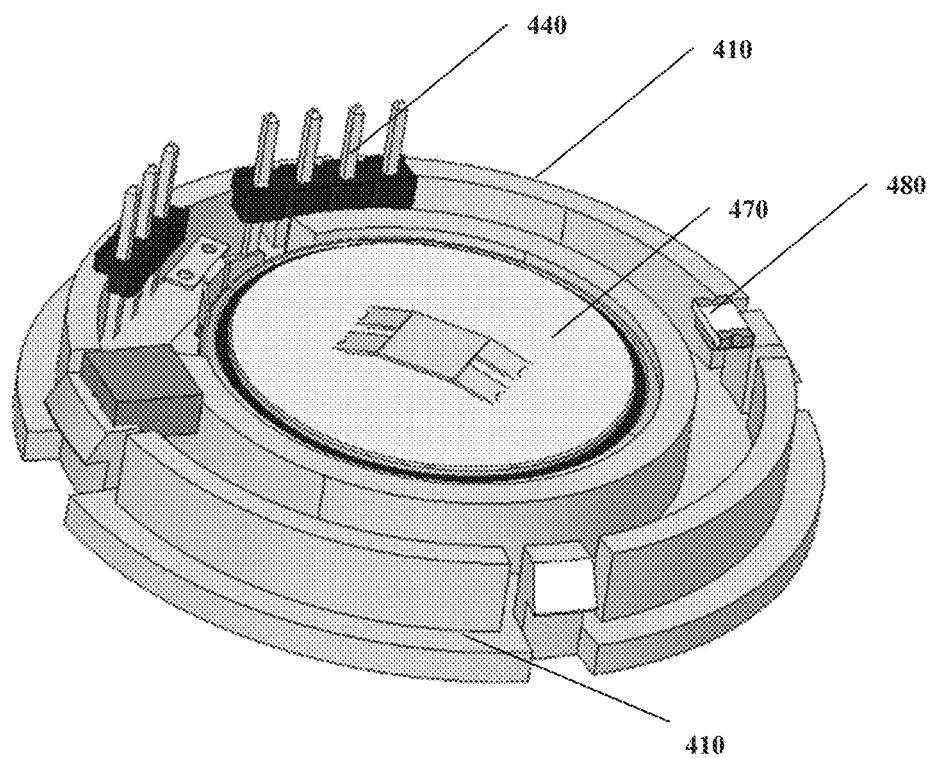
FIG. 15F is a perspective top view of the second battery cover and the second battery.

The force sensor 430 is operably disposed on the bottom sensor socket 400 and operably coupled to the second PCB cap 420. The bottom sensor socket 400 includes a rigid snap connection to the second battery cover 410. The second PCB cap 420 is operably disposed within the bottom sensor socket 400 and on top of the second battery cover 410. The second PCB cap 420 includes the wireless module 450, the force sensor 430, the accelerometer 440, and the memory circuit 460, as shown in FIG. 15E. The accelerometer 440 is operably disposed in the second battery cover 410 and through the second PCB cap 420. The accelerometer 440 detects the orientation of the second cap device 330 and registers when the second cap device 330 is upright along vertical axis direction 301 so the weight can be measured. The accelerometer 440 also detects movements of the container element 310 such as twisting cap device open or close, shaking the container element 310, or tilting of the container element 310. The second battery 470 is operably disposed within the second battery cover 410, as shown in FIG. 15F. Optionally, an LED light 480 is disposed within the second battery cover 410 as to indicate a status or alarm.

The LED light 480 comprise 2 ultra-bright LED chips with a viewing angle of about 120°, forming various color combinations (blue/green, blue/red, red/green, yellow/green) and producing unique color blends. The LED light 480 can achieve variable hues and intensity levels tailoring to a chosen ambience. The LED light 480 includes a low power consumption, IR reflow solderable, and automation friendly series operates under a current as low as 1 mA and meet industrial temperature ratings of −40 C to +85 C.

The detector switch 380 is a type of switch has to be touched by an object to operate and send a signal. In one embodiment, the detector switch is a tactile sensor that measures information arising from first cap device being turned on the top of the container element and disconnecting or connecting with the container element. Tactile sensors are capable of detecting stimuli resulting from mechanical stimulation, temperature. Tactile sensors may be of different types including piezoresistive, piezoelectric, capacitive and elastoresistive sensor. Piezo touch switches are based on mechanical bending of piezo ceramic, typically constructed directly behind a surface. A resistance switch needs two electrodes to be physically in contact with something electrically conductive to operate. A capacitance switch needs one electrode to function. The electrode can be placed behind a non-conductive panel.

Optionally, a temperature sensor may be operably disposed within the bottom connector 390 or the tube connector 590. The temperature sensor detects the temperature inside the mouth of the container element 310. Optionally, a connector thermistor proximity may be operably coupled the bottom sensor socket 400 and the PCB cap 230. The connector thermistor proximity sensor senses when the container element 310 is present or absent from the second cap device 330.

Figure 16A:
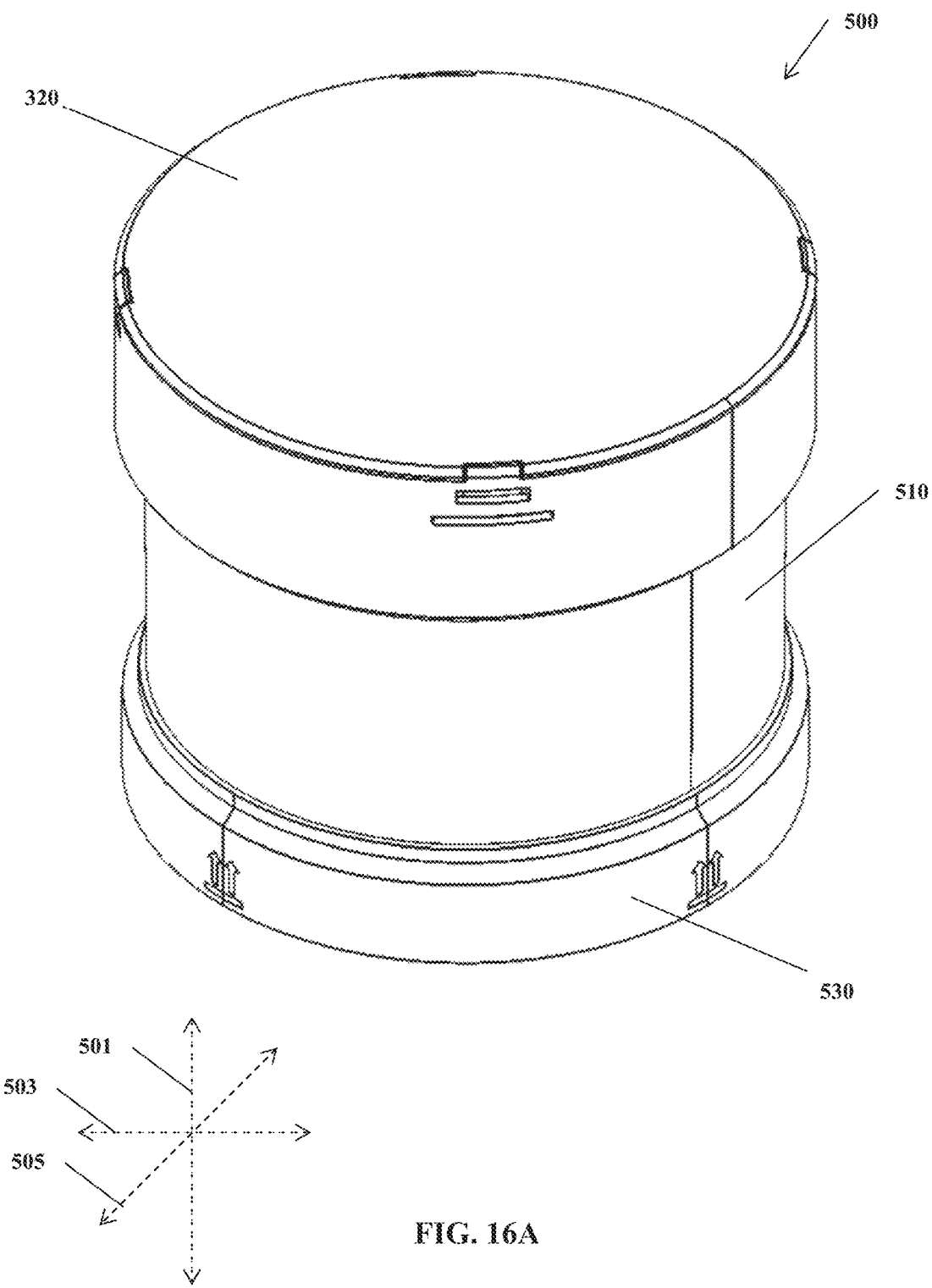
FIG. 16A a perspective view of an alternative embodiment of the medication adherence apparatus.

An alternative embodiment of the medication adherence apparatus 500 is shown in FIG. 16A. The medication adherence apparatus 500 comprises a container element 510 and a first cap device 520 and a second cap device 530, as shown in FIG. 16A. The container element 510 may be any container element to house a medication, such as an ointment tube, wide-mouthed plastic jar, or a platform developed for storage, display, and utilization of medicament container such as a tube, pill bottle, balm jar or tray. The medication may be any type of medication, either in pill, powder, liquid, or gas form. The cap state comprises the force or weight of the container element, the orientation of the first cap device 520 or second cap device 530, the temperature of the first cap device 520 or second cap device 530, and the time stamp including the day, time, and date. The force or weight of the container element 510 is obtained when the container element 510 is inserted into the first cap device 520 or the second cap device 530. The temperature inside the mouth of the container element 310 is obtained by the first cap device 520 or second cap device 530. The presence or absence of the container element 510 in the first cap device 520 is detected by the first cap device 520. The orientation of the first cap device 520 or second cap device 330 is detected to determine if the first cap device 520 or second cap device 530 and/or the container element 510 is upright, which is generally along the vertical axis 301. And any movements of the first cap device 520 or second cap device 530 may be detected, such as along the vertical axis direction 501, the longitudinal axis 503, or the lateral axis 505. The second cap device 530 detects the weight of the container element 510. The first cap device 520 or second cap device 530 receives a medication schedule and notification parameters to notify a patient by an alarm if medication is missed. The alarm may be an audio sound, a visual notification, an electronic notification, or a cell phone notification.

Figure 16B:
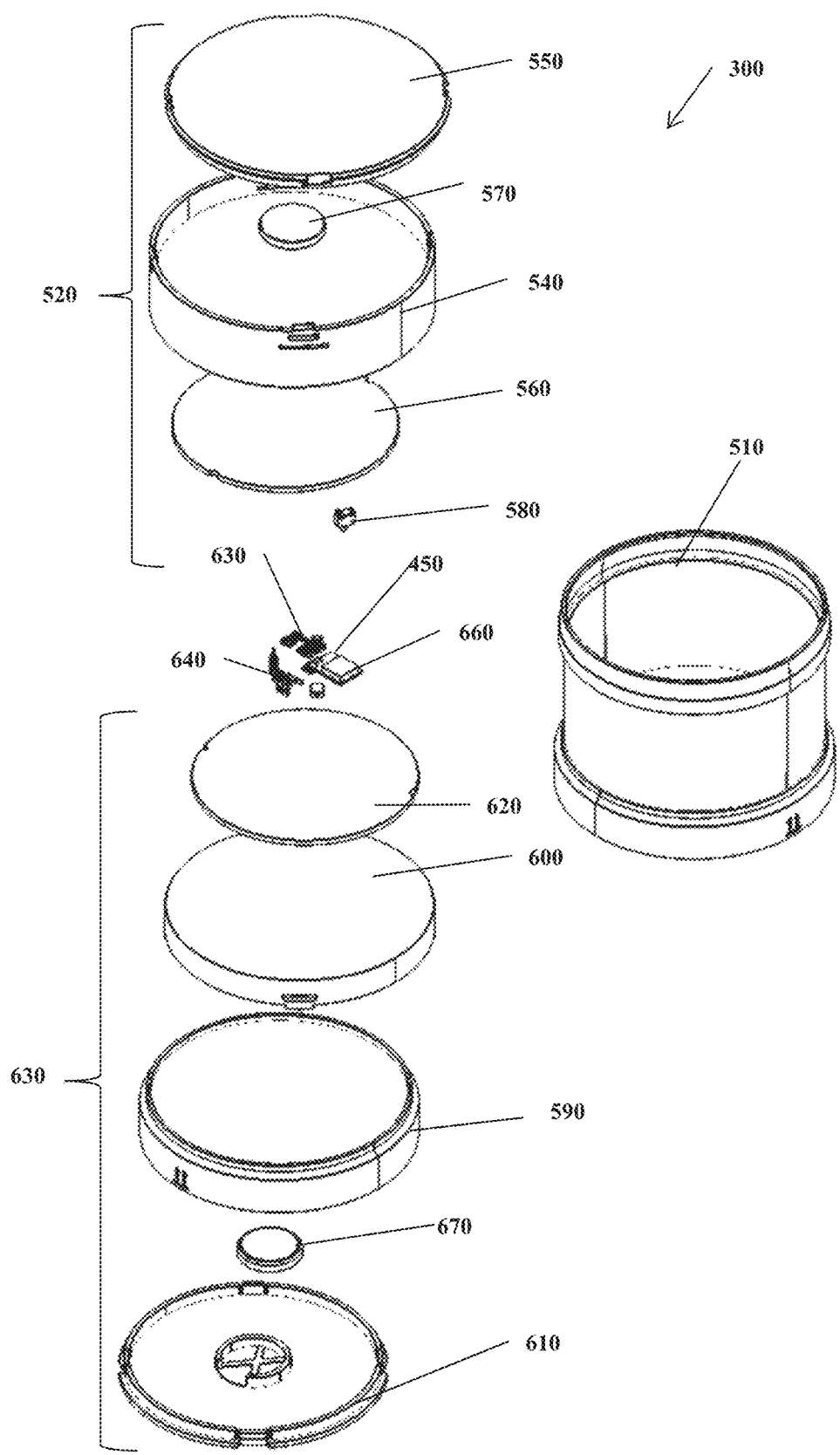
FIG. 16B is an exploded view of the first cap device and second cap device, according to one embodiment.

As shown in FIG. 16B, the medication adherence apparatus 500 and the components of the first cap device 520 and the second cap device 530 are shown. The first cap device 520 includes a first main housing 540, a first battery cover 550, a first PCB cap 560, a first battery 570, and a detector switch 580. The second cap device 530 includes a bottom connector 590, a second battery 670, a bottom sensor socket 600, a second battery cover 610, a second PCB cap 620, a force sensor 630, an accelerometer 640, a wireless module 650, and a memory card 660.

Figure 16C:
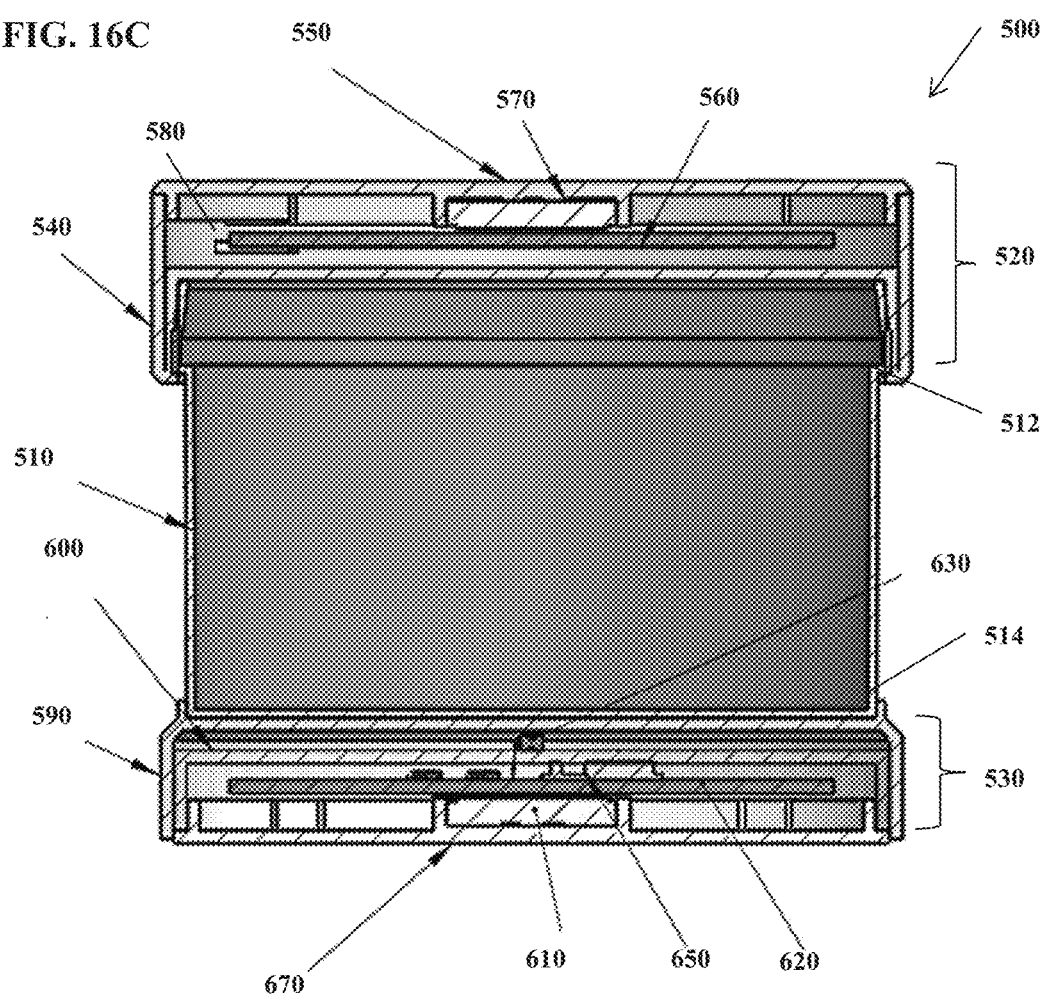
FIG. 16C is a cross sectional view of the medication adherence apparatus from FIG. 16A.
Figure 16D:
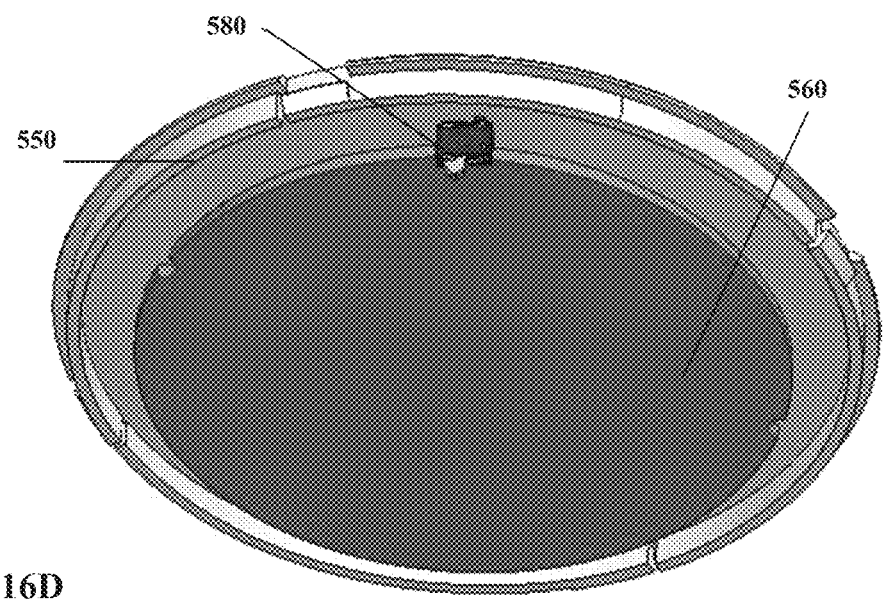
FIG. 16D is a perspective bottom view of the first battery cover.

As shown in FIG. 16C, the first battery cover 550 is operably disposed over the first main housing 540 and the first battery 570 to enclose the top portion of the first cap device 520. The first main housing 540 secures the first cap device 520 to the container element 510 by way of a threaded connection or capped connection 512 on the top end of the container element 510. The first battery 570 is operably disposed over the first PCB cap 560 and the detector switch 580 is operably coupled with the PCB cap 560 as to detect the movement and connection of the first cap device 520 to the container element 510. The detection signal is sent to remote module to notify the user if the first cap device 520 is secured to the container element 510 and notifies a program or module every time the first cap device 520 is removed or secured to the container element 510. The first battery cover 550 may include a snap fit connection to secure to the first main housing 540, as shown in FIG. 16D.

As shown in FIG. 16C, the bottom end 514 of the container element 510 is operably secured on the bottom connector 590. The bottom connector 590 may be altered such that different types of container elements 510 may be secured with the second cap device 530. The force sensor 630 is operably disposed under the top portion of the bottom connector 590 as to detect the force or weight of the container element 510 secured into the second cap device 530.

Figure 16E:
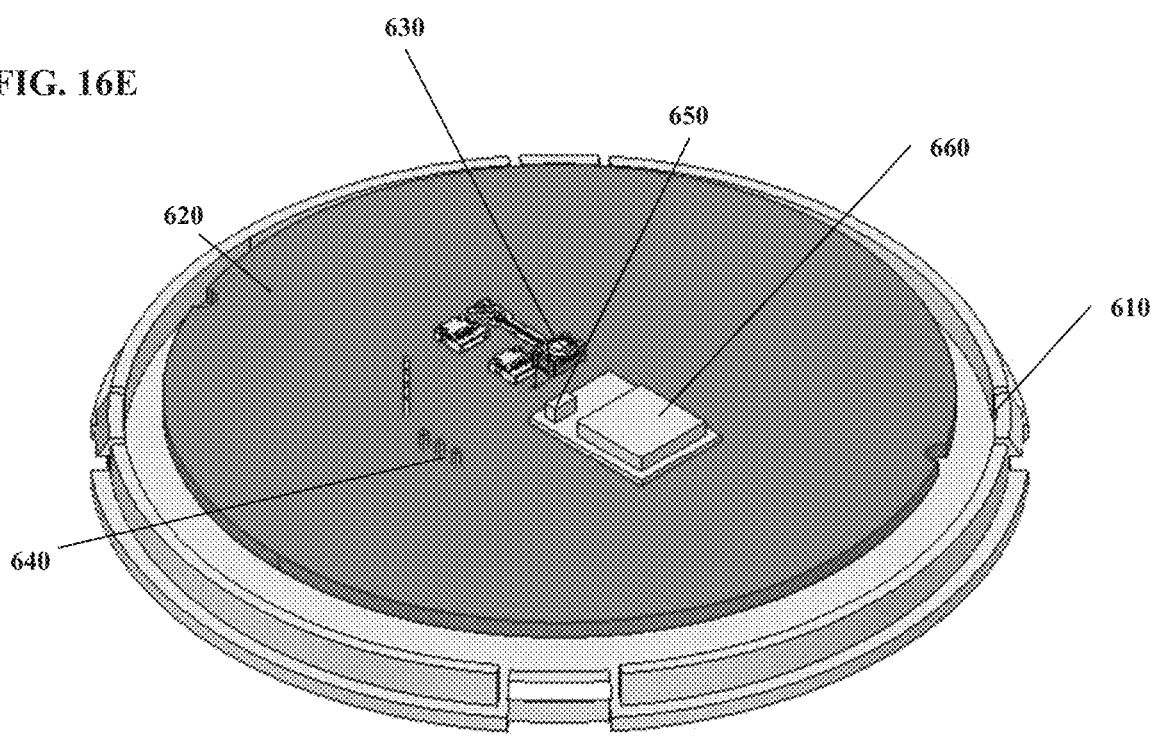
FIG. 16E is a perspective top view of the second battery cover and the second PCB cap.
Figure 16F:
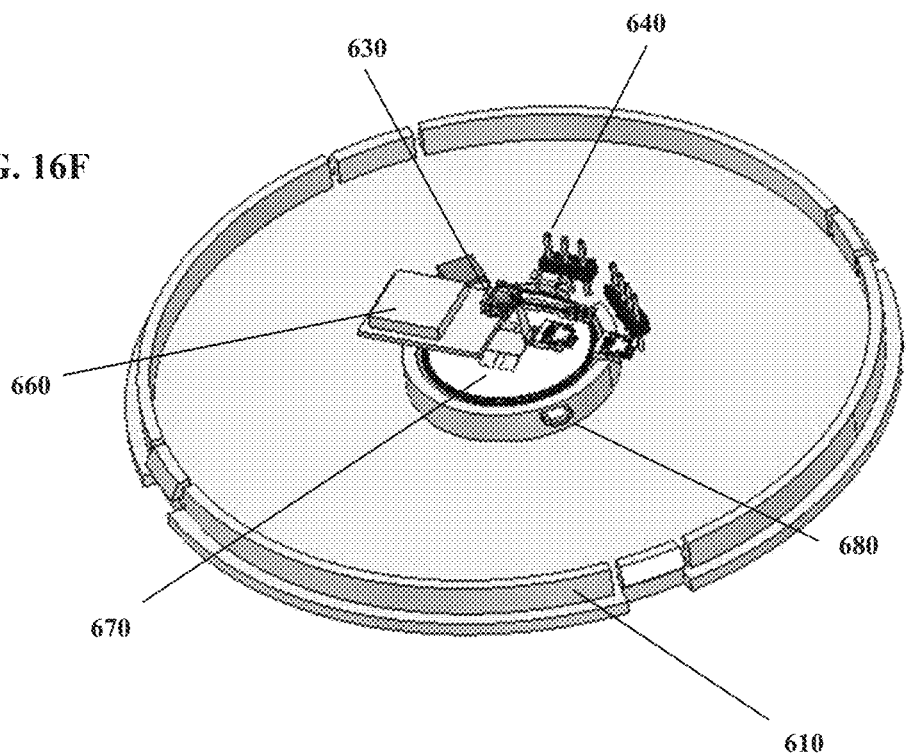
FIG. 16F is a perspective top view of the second battery cover and the second battery.

The force sensor 630 is operably disposed on the bottom sensor socket 400 and operably coupled to the second PCB cap 620. The bottom sensor socket 600 includes a rigid snap connection to the second battery cover 610. The second PCB cap 620 is operably disposed within the bottom sensor socket 600 and on top of the second battery cover 610. The second PCB cap 620 includes the wireless module 650, the force sensor 630, the accelerometer 640, and the memory circuit 660, as shown in FIG. 16E. The accelerometer 640 is operably disposed in the second battery cover 610 and through the second PCB cap 620. The accelerometer 640 detects the orientation of the second cap device 530 and registers when the second cap device 330 is upright along vertical direction 501 so the weight can be measured. The accelerometer 640 also detects movements of the container element 510 such as twisting cap device open or close, shaking the container element 510, or tilting of the container element 510. The second battery 670 is operably disposed within the second battery cover 610, as shown in FIG. 16F. Optionally, an LED light 680 is disposed within the second battery cover 610 as to indicate a status or alarm.

Optionally, a temperature sensor may be operably disposed within the bottom connector 590 or the tube connector. The temperature sensor detects the temperature inside the mouth of the container element 510. Optionally, a connector thermistor proximity may be operably coupled the bottom sensor socket 600 and the PCB cap 620. The connector thermistor proximity sensor senses when the container element 510 is present or absent from the second cap device 530.

Adherence Monitoring: Cap Device and Data Acquisition, Storing and Sharing

In one embodiment, data recording comprises recording data in intervals of 1 about second in sets consisting of: a Timestamp (Unix-time); a Cap device status (On/Off); an Orientation of Device (16 bit code of motion-sensor, Z-gravity vector), a Force (for calculating weight), a Temperature (Resistance of thermistor). In one embodiment, a trigger event time-based may be a time period for continuous tracking of temperature and other tracking parameters. In one embodiment, the time period may be about 30 minutes.

Data storing comprises storing data in a floating buffer of about 50 to about 200 datasets. When a new set of Data is created, old data is moved to next "slot" and latest set stored in first slot. In one embodiment, the newest set of Data is always in first slot. Data is not deleted from device after reading by a mobile device. But when the Buffer is full, then the oldest set is deleted whenever a new set is added in subsequent order.

In one embodiment, data sharing comprises broadcasting 1 Service with a 1 Characteristic for each Value, a +1 Characteristic for slot-selection. Then the mobile device connects to cap device, selects Dataset, reads desired Values, and selects next Dataset. In one embodiment, the data sharing comprises broadcasting 1 Service with a 1 Characteristic for live-timestamp in the cap device, a +1 Characteristic for setting Timestamp through the mobile device, a +1 Characteristic to initiate pairing mode. In one embodiment, the data sharing comprises broadcasting 1 Service with a 1 Characteristic for Battery Level of the Cap Device. In one embodiment, the data sharing comprises broadcasting 1 Service with Characteristics for uploading medication schedule to Device for user-notifications.

Security/Pairing/Bonding comprises using Bluetooth Low Energy (BLE) Encrypted Connection through Trusted device database. In one embodiment, any device is allowed to pair/bond. The cap device may receive updates and further security measures at a later time point. In one embodiment, at first startup of the device, the next mobile device connecting is allowed to bond, and hence is able to access the datasets and settings; other attempts are rejected, unless: bonded device activates paring mode, then bonding of another device are allowed for about 30 seconds.

Figure 17A:
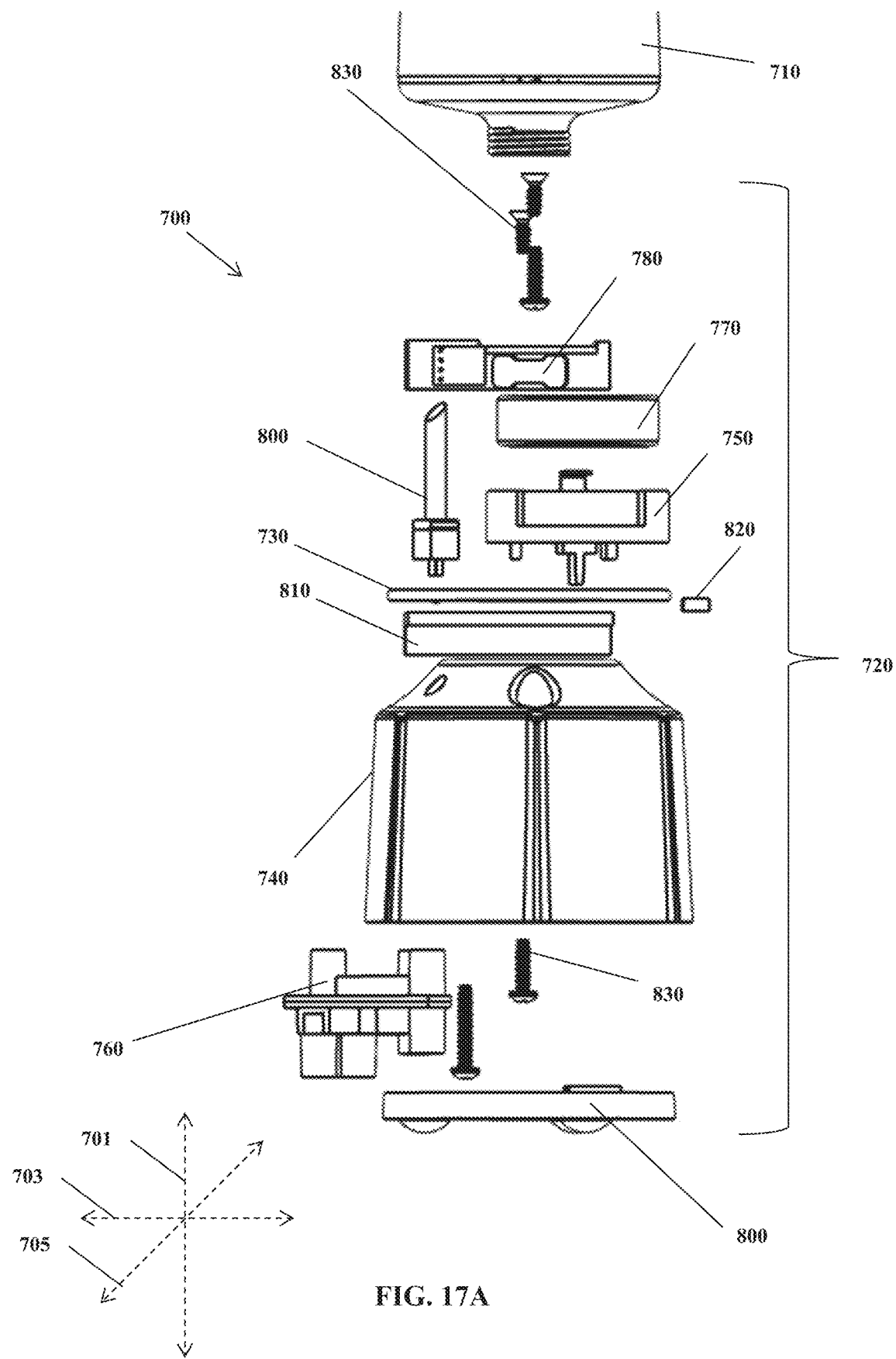
FIG. 17A is an exploded view of another embodiment of the medication adherence apparatus and the components of the third cap device.

An alternative embodiment of the medication adherence apparatus 700 is shown in FIG. 17A. The medication adherence apparatus 700 comprises a container element 710 and a third cap device 720, as shown in FIG. 17A. The elements, sensors, and components of the third cap device are interchangeable with the first cap device and second cap device. The container element 710 may be any container element to house a medication, such as an ointment tube, wide-mouthed plastic jar, or a platform developed for storage, display, and utilization of medicament container such as a tube, pill bottle, balm jar or tray. The medication may be any type of medication, either in pill, powder, liquid, or gas form. The cap state comprises the force or weight of the container element, the orientation of the third cap device 720, the temperature of the third cap device 720, and the time stamp including the day, time, and date. The force or weight of the container element 710 is obtained when the container element 710 is inserted into the third cap device 720. The temperature inside the mouth of the container element 710 is obtained by the third cap device 720. The presence or absence of the container element 710 in the third cap device 720 is detected by the third cap device 720. The orientation of the third cap device 720 is detected to determine if the third cap device 720 or and/or the container element 110 is upright, which is generally along the vertical axis 701. And any movements of the third cap device 720 may be detected, such as along the vertical axis 701, the longitudinal axis 703, or the lateral axis 705. The third cap device 720 receives a medication schedule and notification parameters to notify a patient by an alarm if medication is missed. The alarm may be an audio sound, a visual notification, an electronic notification, or a cell phone notification.

Figure 17B:
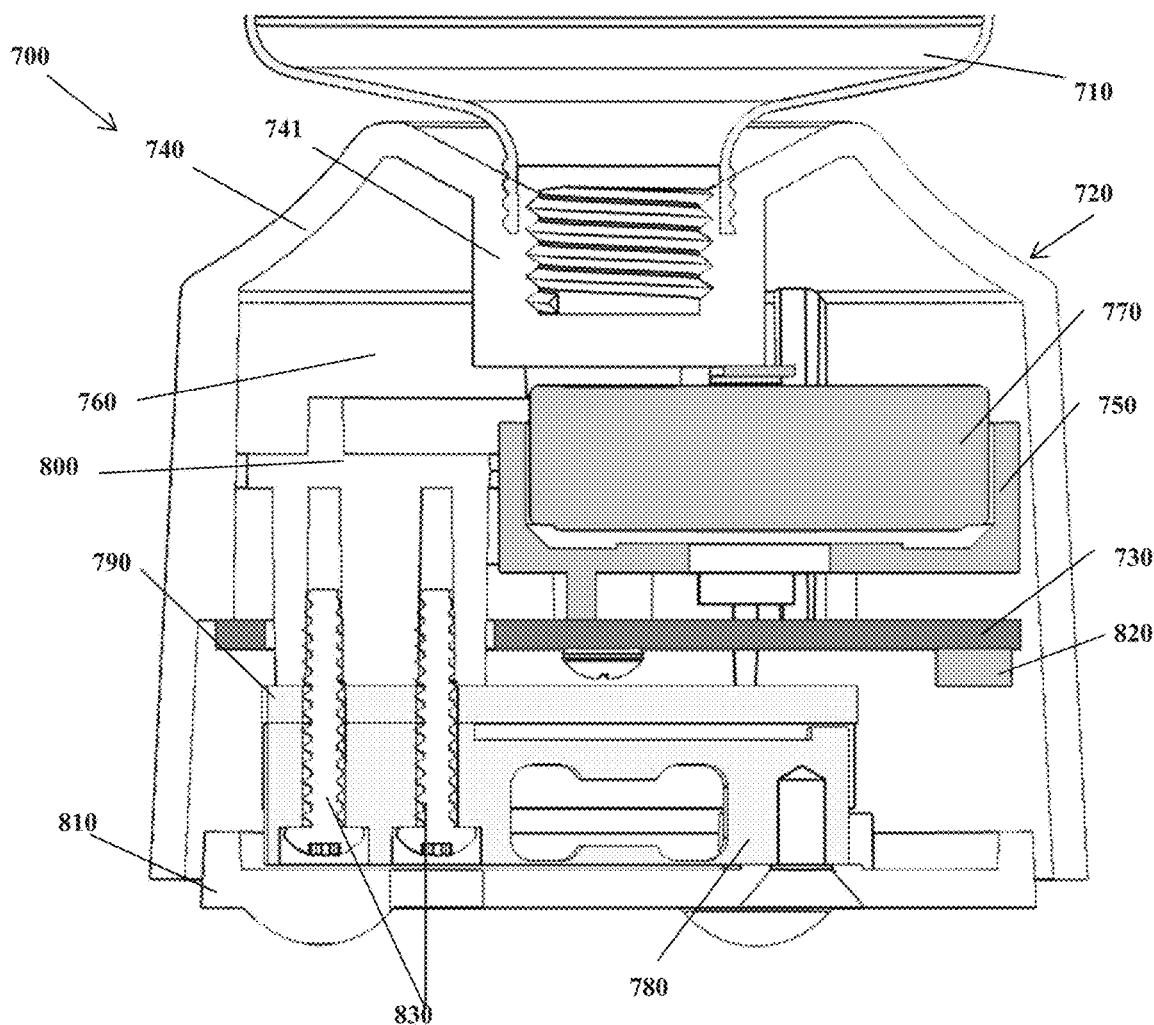
FIG. 17B is cross sectional view of the third cap device.
Figure 17B:
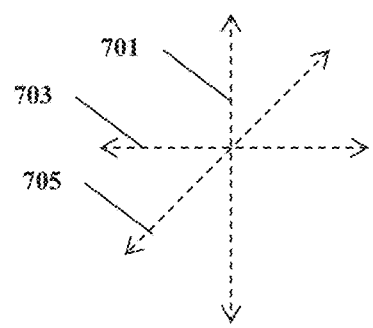

As shown in FIG. 17A-17B, the medication adherence apparatus 700 and the components of the third cap device 720 are shown in one embodiment. The third cap device 720 includes a PCB 730, a first main housing 740, a first battery cover 750, a first spacer cap 760, a battery 770, a load cell 780, a bottom stop cap 790, a light pipe 800, and a base cap 810, a Surface Mount Transducer 820; and a plurality of screws 830. The load cell 780 detects the movement and connection of the third cap device 720 to the container element 710. The detection signal is sent to a remote module to notify the user if the third cap device 720 is secured to the container element 710 and notifies a program or module every time the third cap device 720 is removed or secured to the container element 710. The first main housing 740 includes a top threaded portion 741 to secure the container element 710 to the top portion of the first main housing 740. As shown in FIG. 17E, a proximity sensor 916 is disposed on the top portion of the first main housing 740 to detect the securement of the container of the first main housing. In one embodiment, the proximity sensor is a copper wire operable to detect the presence of the first container by way of electrical connection. In another embodiment, the proximity sensor 916 is a copper sheet 917 disposed on the top portion of the first main housing 740. The copper sheet 917 is operably coupled to a shield 919 to protect the proximity sensor 916 from false readings when connected with the container. The proximity sensor 916 can connect with the PCB by way of a coupler 921.

Figure 17C:
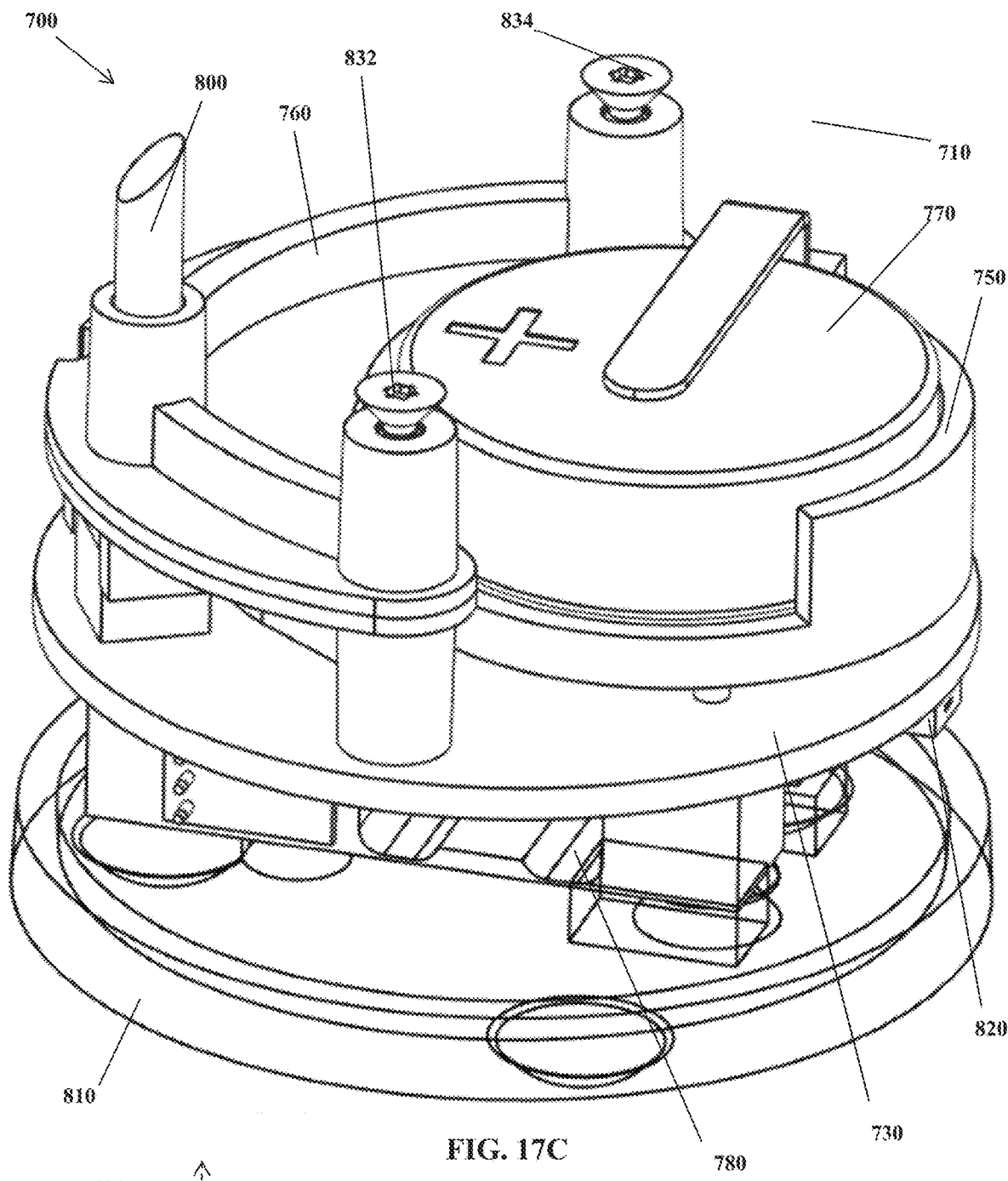
FIG. 17C is a perspective view of the battery operably disposed in the first battery cover operably disposed over the PCB.
Figure 17C:
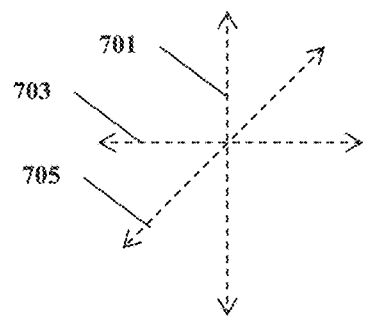

As shown in FIG. 17C, the battery 770 is operably disposed in the first battery cover 750 is operably disposed over the PCB 730. The first battery cover 750 is operably coupled with the first spacer cap 760. The first spacer cap 760 is operably coupled with the light pipe 800 and is operably disposed over the PCB 730. A first screw 832 and a second screw 834 secures the first main housing 740 to the first spacer cap 760. The PCB 730 is operably coupled with the Surface Mount Transducer 820 and the PCB 730 is operably disposed with the load cell 780. The load cell 780 is operably disposed on the base cap 810.

Figure 17D:
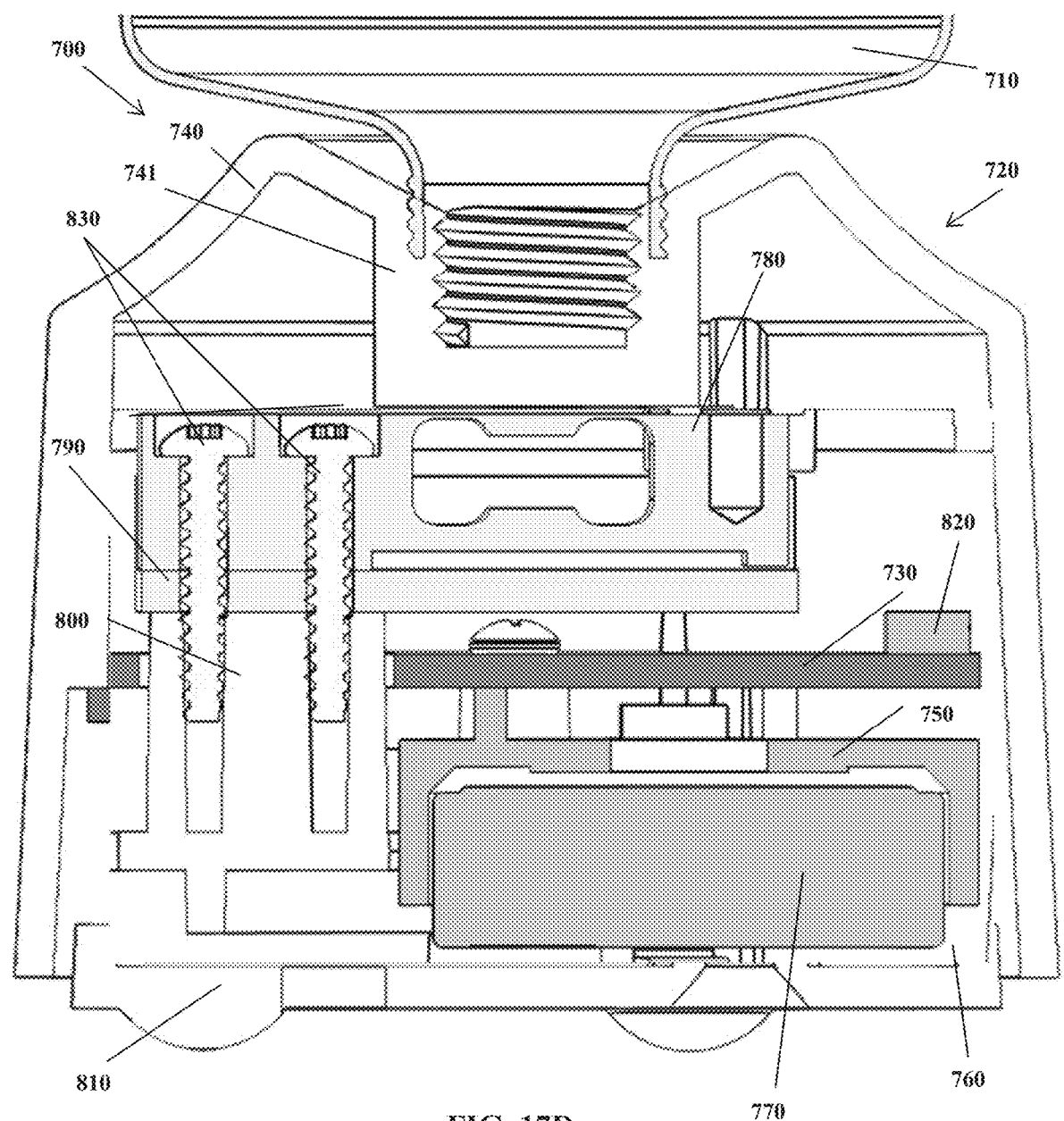
FIG. 17D is a cross-sectional view of another embodiment of the third cap device.
Figure 17E:
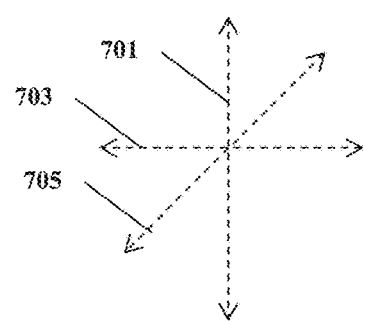
FIG. 17E is a top view of one embodiment of the proximity sensor.

In another embodiment, as shown in FIG. 17D, the load cell 780 is operably coupled to top portion of the first main housing 740. The bottom stop cap 790 is disposed on the top portion of the first main housing 740 with the load cell 780 and secured with the plurality of screws 830. The battery 770 and the first battery cover 750 are operably disposed on the bottom portion of the first main housing 740 with the first spacer cap 760 and the base cap 810. The light pipe 800, PCB 730, and the Surface Mount Transducer 820 are operably disposed in the middle portion of the first main housing.

Figure 17F:
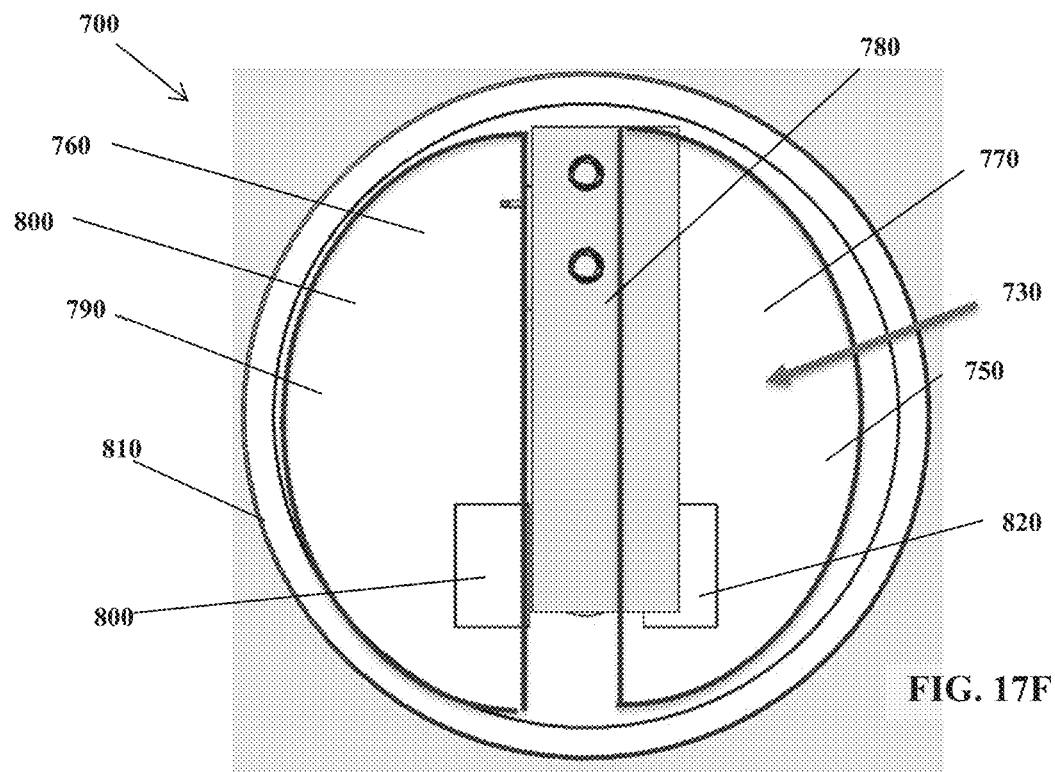
FIG. 17F is a top view of another embodiment of the third cap device.
Figure 17G:
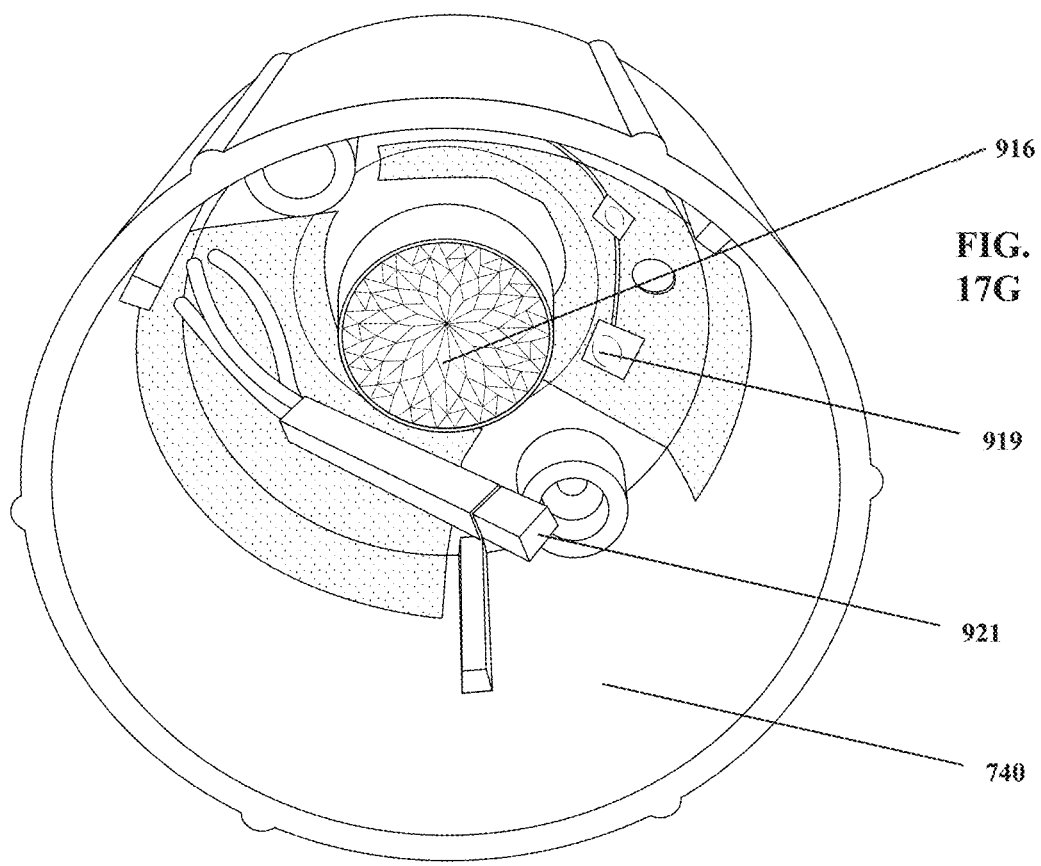
FIG. 17G is a bottom perspective view of the first main housing with an alternative proximity sensor.

In another embodiment, as shown in FIG. 17F, the PCB 730, the first battery cover 750, the first spacer cap 760, the battery 770, the bottom stop cap 790, the light pipe 800, the Surface Mount Transducer 820 are mounted around the load cell 780.

Figure 18A:
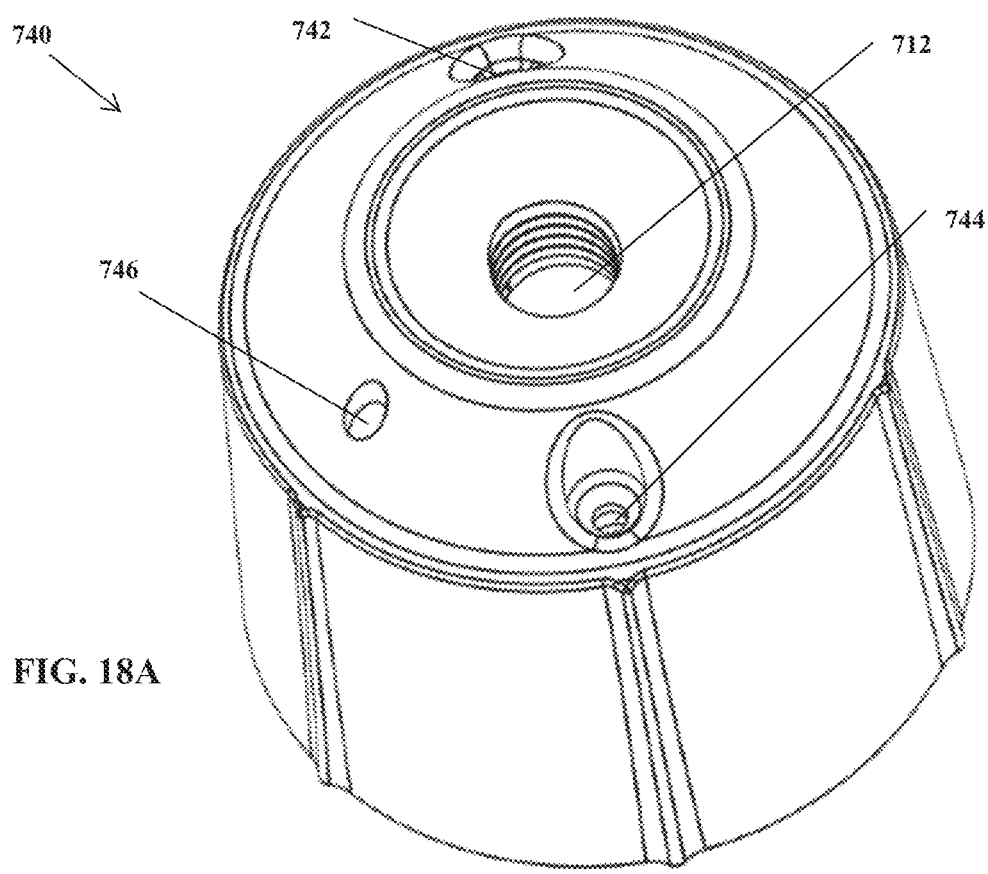
FIG. 18A is a perspective top view of the first main housing.
Figure 18B:
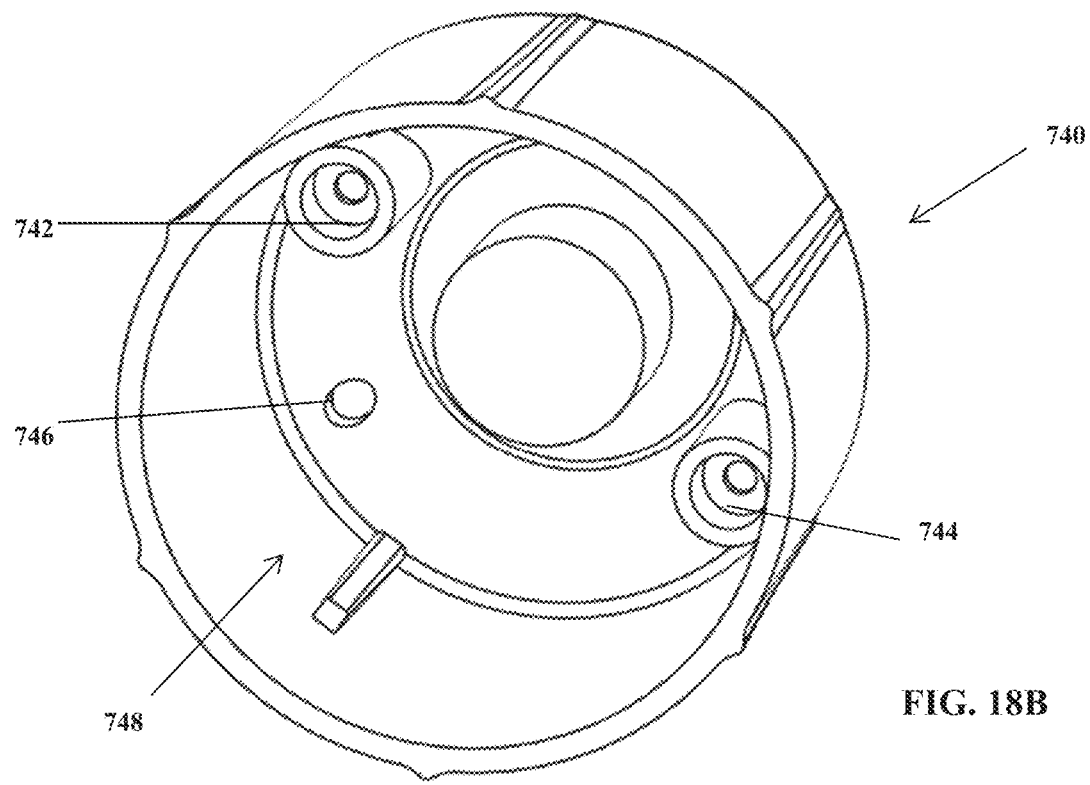
FIG. 18B is a perspective bottom view of the first main housing.

As shown in FIG. 18A-18B, the first main housing 740 includes a first screw hole 742 and second screw hole 744 to operably secure the first main housing 740 to the first spacer cap 760 by way of the first screw 832 and the second screw 834. The first main housing 740 includes a central lumen 748 that encloses the PCB 730, the first battery cover 750, the first spacer cap 760, the battery 770, the load cell 780, the bottom stop cap 790, the light pipe 800, a base cap 810, the Surface Mount Transducer 820. The first main housing 740 secures to the container by way of a threaded connection or capped connection 712 on the top end of the container element. The first main housing 740 includes a light hole 746 through which the light pipe 800 traverses for the alarm notification.

Figure 19A:
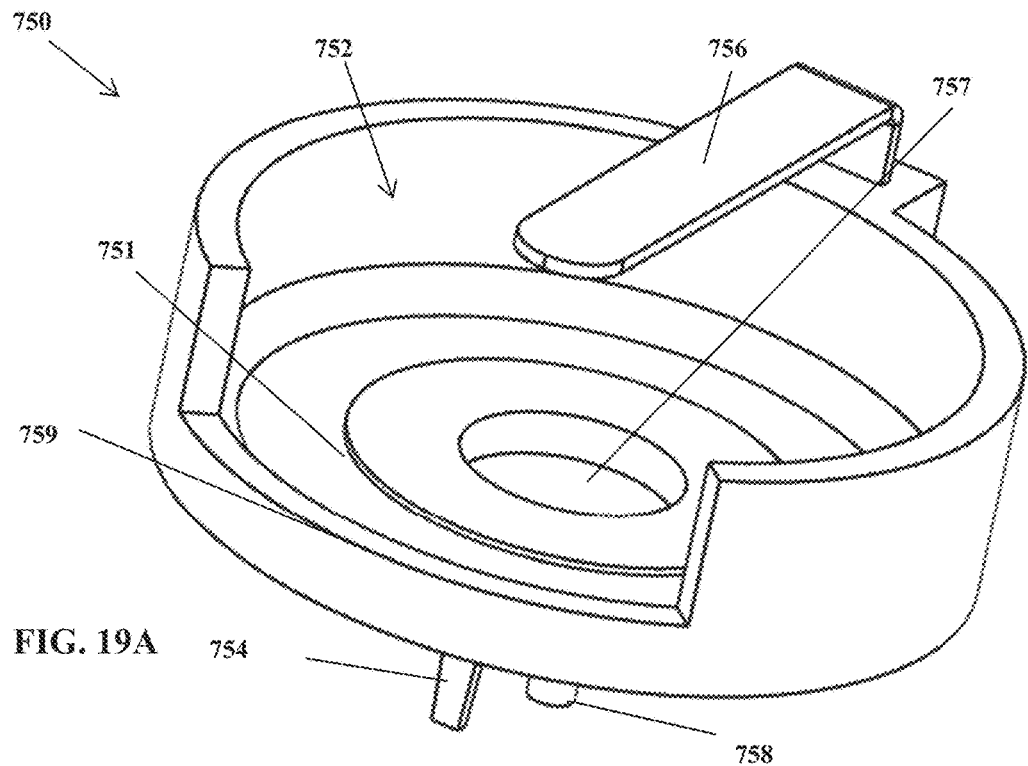
FIG. 19A is a perspective top view of the first battery cover.
Figure 19B:
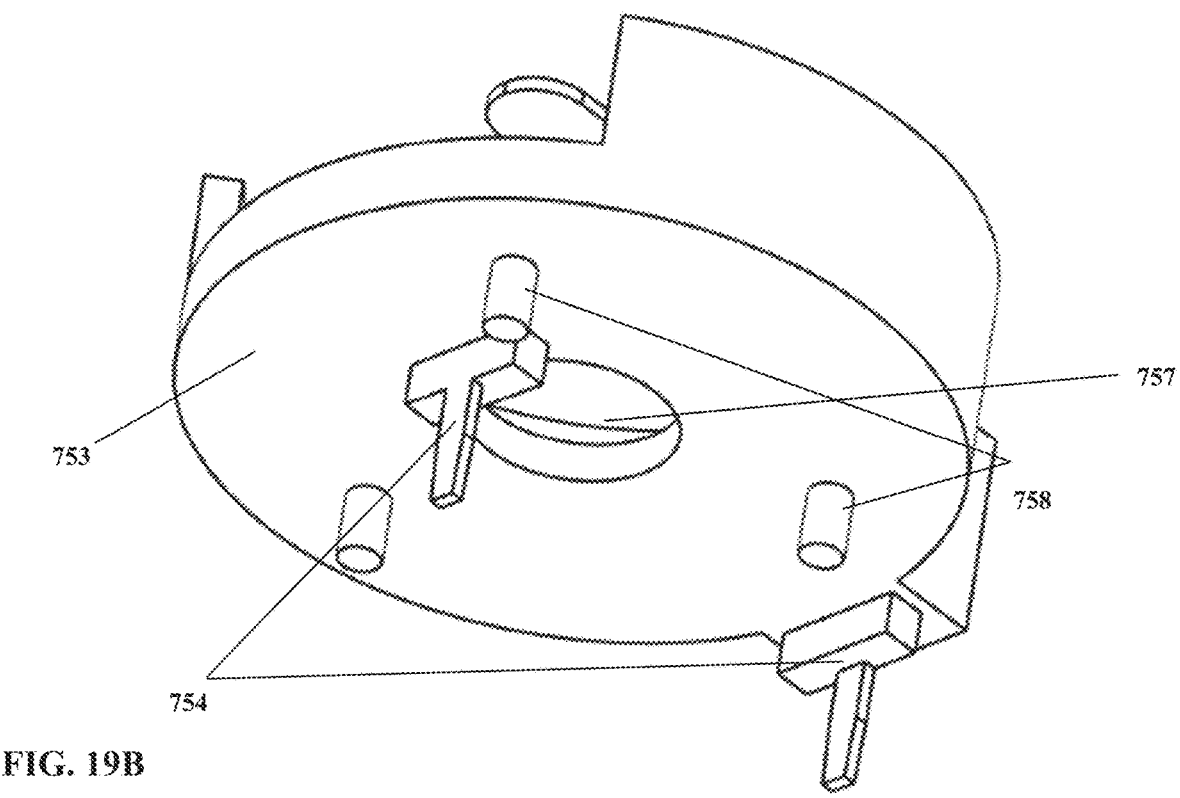
FIG. 19B is a perspective bottom view of the first battery cover.

As shown in FIG. 19A-19B, the first battery cover 750 including a top side 751 and a bottom side 753 in a general circular profile. The top side 751 includes a central holding lumen 752 to house the battery, and the bottom side 753 includes a plurality of tabs 754 to secure the first battery cover 750 to the PCB and operably couple with the PCB. The top side 751 includes a holding tab 756 to secure the battery within the central holding lumen 752 and a central bore 757 traversing the top side 751 and the bottom side 753. The bottom side 753 includes a plurality of battery contacts 758 to transmit the battery's electrical energy to the PCB and bottom tab. In one embodiment, the top side 751 includes a top open portion 759 to permit installation of the battery. Alternatively, a side insertion opening could be employed.

Figure 20A:
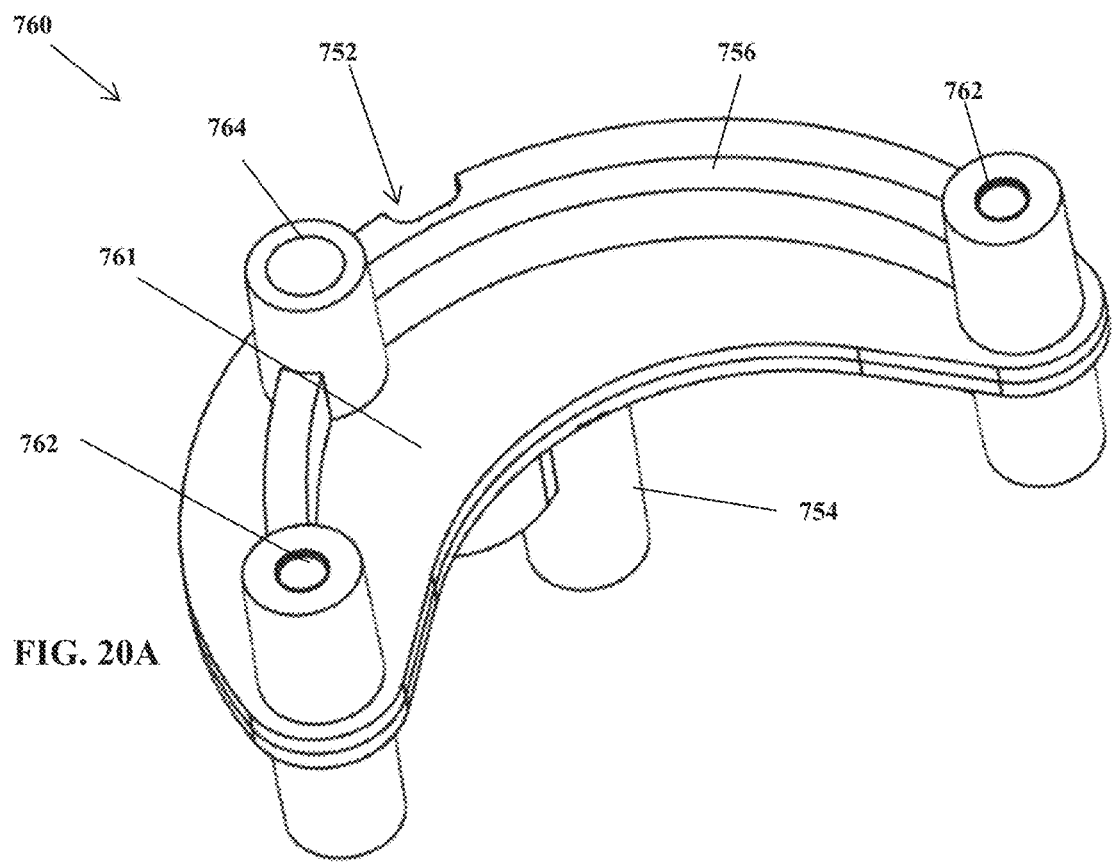
FIG. 20A is a perspective top view of the first spacer cap.
Figure 20B:
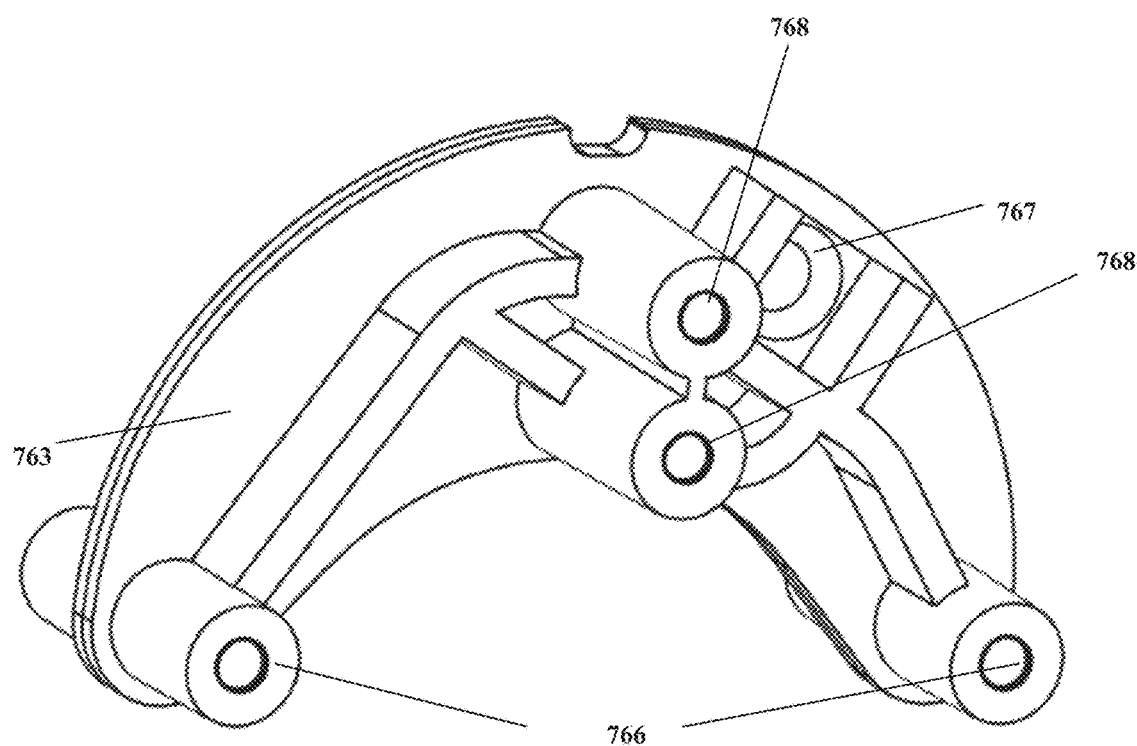
FIG. 20B is a perspective bottom view of the first spacer cap.

As shown in FIGS. 20A-20B, the first spacer cap 760 includes a top side 761 and a bottom side 763 in a general curvilinear profile. The top side 761 includes at least two screw lumens 762 including an inner threaded surface to engage the first screw and the second screw. The top side 761 includes a light pipe lumen 764 to permit the light pipe to traverse the bottom side 763 and the top side 761 and protrude through the light pipe lumen 764. The bottom side 763 includes at least two threaded lumens 766 to engage a plurality of screws and secure the PCB to the bottom side of the 763 of the first spacer cap 760. The bottom side 763 includes at least two second threaded lumens 768 to secure the load cell and the bottom stop cap to the first spacer cap 760. The bottom side 763 includes a light pipe holder 767 to secure the bottom end of the light pipe. The side of the first spacer cap 760 may include a c-shape 769 for operably coupling with the first main housing 740

Figure 21A:
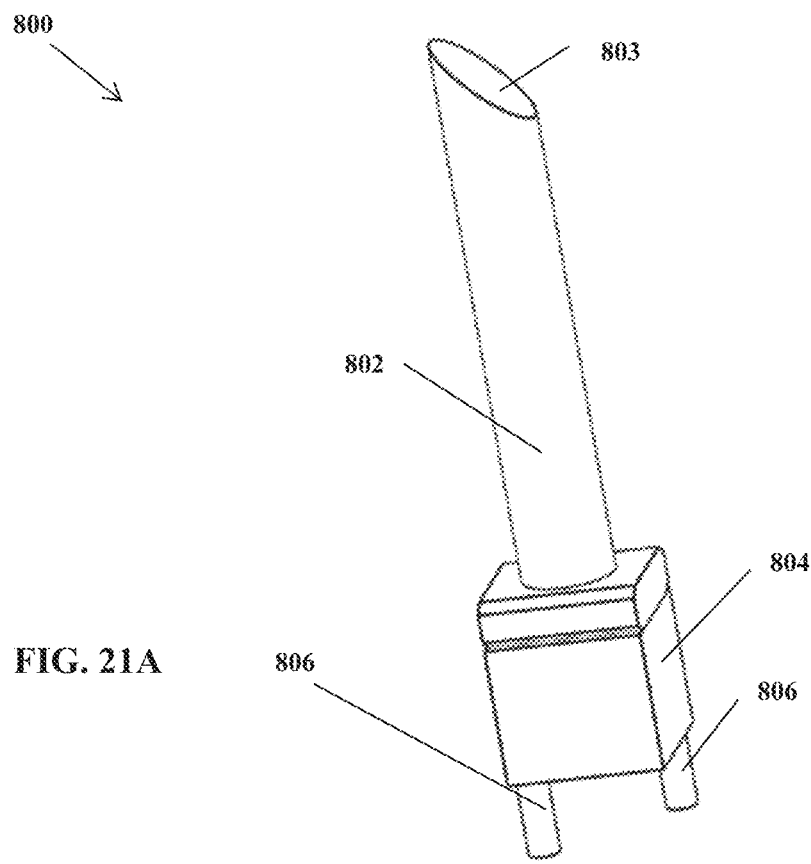
FIG. 21A is a perspective top view of the light pipe.
Figure 21B:
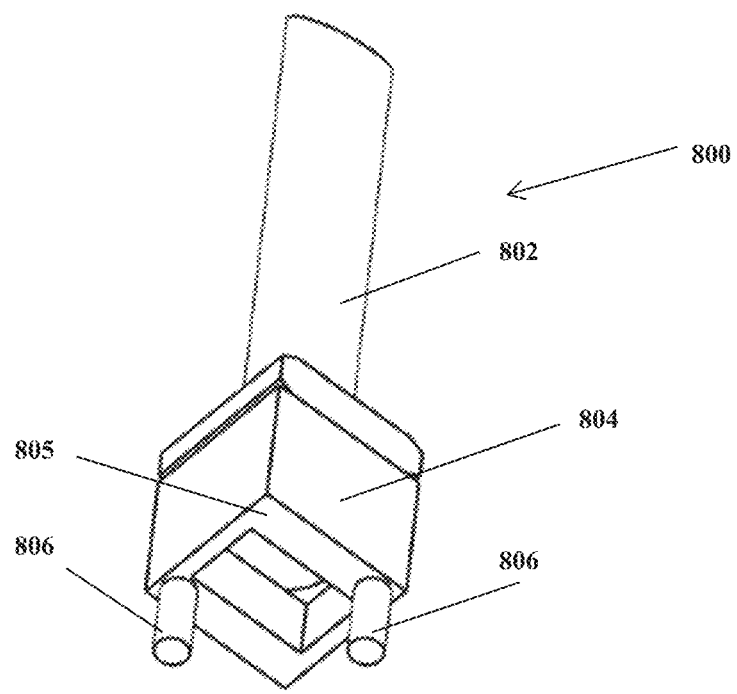
FIG. 21B is a perspective bottom view of the light pipe.

As shown in FIGS. 21A-21B, the light pipe 800 includes a central light portion 802 extending from a bottom base portion 804. The central light portion 802 is a light emitting alarm for the third cap device 720. In one embodiment, the central light portion 802 may be light emitting diode, although other light emitting energies may be used, such as fluorescence, incandescent light bulb, High-intensity discharge lamps, and the like. The central light portion 802 includes a top slanted portion 803, which operably couples with the first main housing 740. The bottom base portion 804 includes a bottom side 805 in which two electrical contacts 806 are disposed. The bottom side 805 sits on top of the PCB and the two electrical contacts 806 operably couple with the PCB to operate and control the light pipe 800.

Figure 22A:
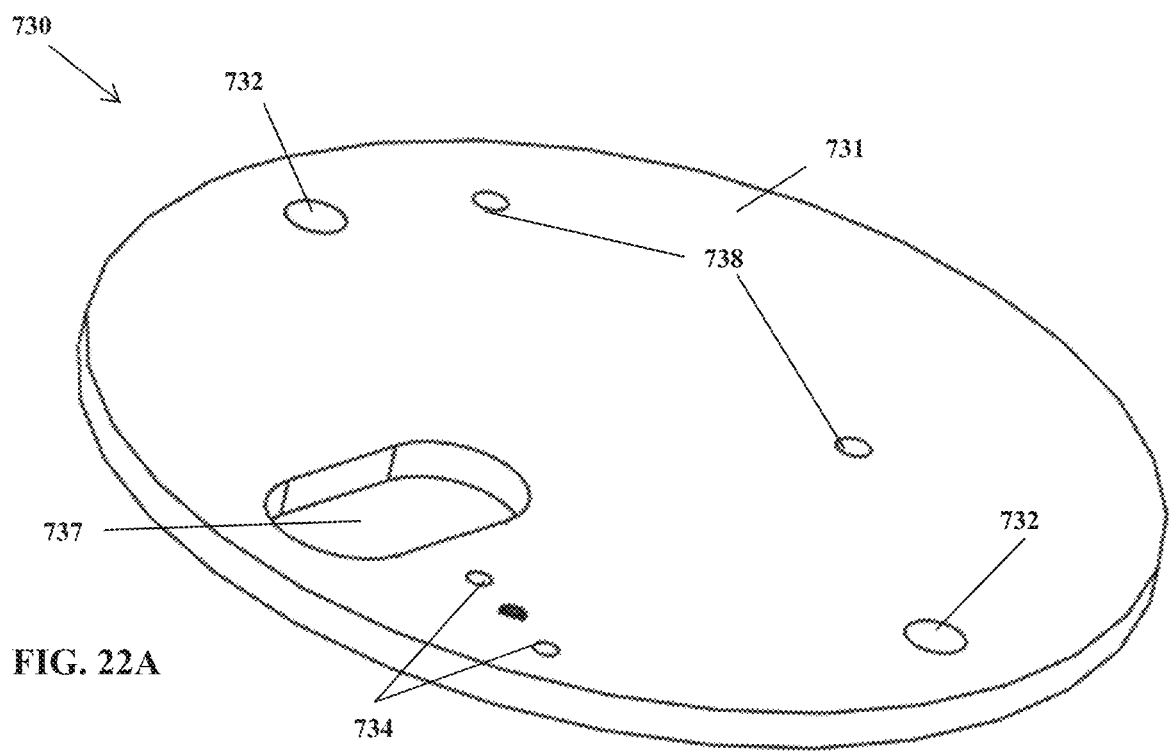
FIG. 22A is a perspective top view of the PCB.
Figure 22B:
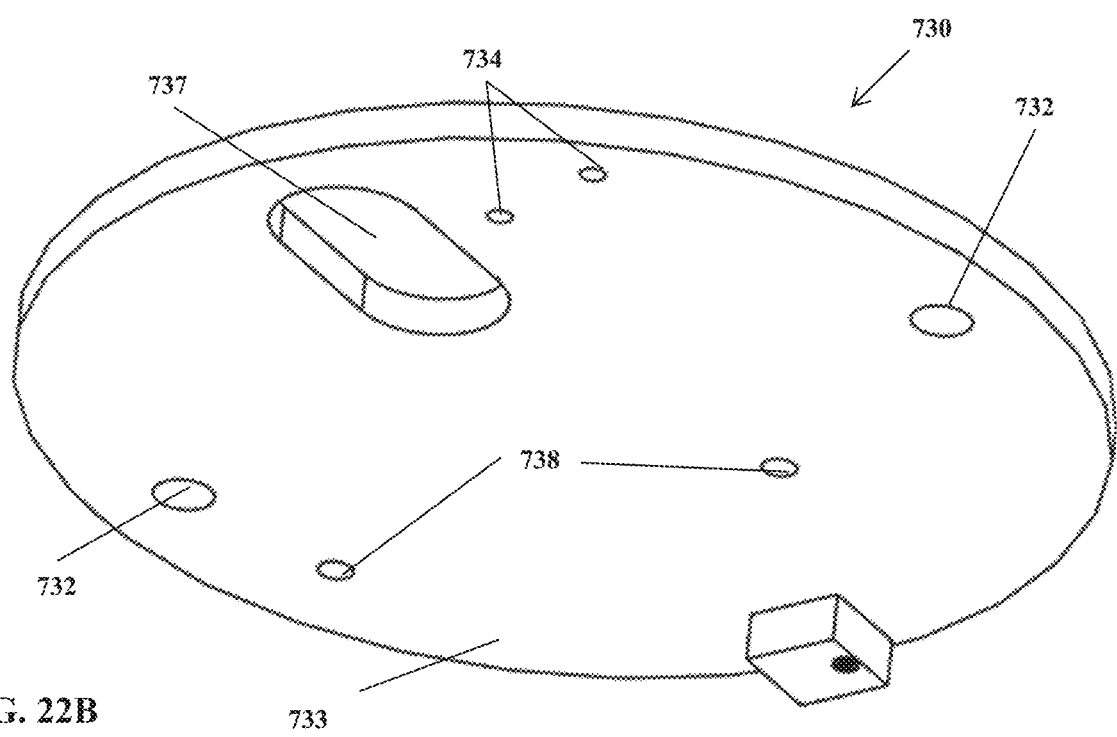
FIG. 22B is a perspective bottom view of the PCB.

As shown in FIGS. 22A-22B, the PCB 730 includes a top side 731 and a bottom side 733 in a general circular configuration. The PCB 730 includes at least two screw holes 732 located on opposing sides and traversing the top side 731 and the bottom side 733. The at least two screw holes 732 permit the plurality of screws 830 to secure the PCB to the first spacer cap 760. The PCB 730 includes at least two electrical contacts 734 to secure the light pipe 800 and operably couple with the electrical contacts 806 of the light pipe 800. The PCB 730 includes at least two battery contacts 738 to operably couple with the first battery cover 750 and the plurality of tabs 754. The PCB 730 includes a circular pass through 737 through which the at least two second threaded lumens 768 of the first spacer cap 760 pass through to secure the load cell. The Surface Mount Transducer 820 is operably disposed on the bottom side 733. The surface mount transducer 820 sounds an audible alarm when signaled by the PCB and the load cell.

Figure 22C:
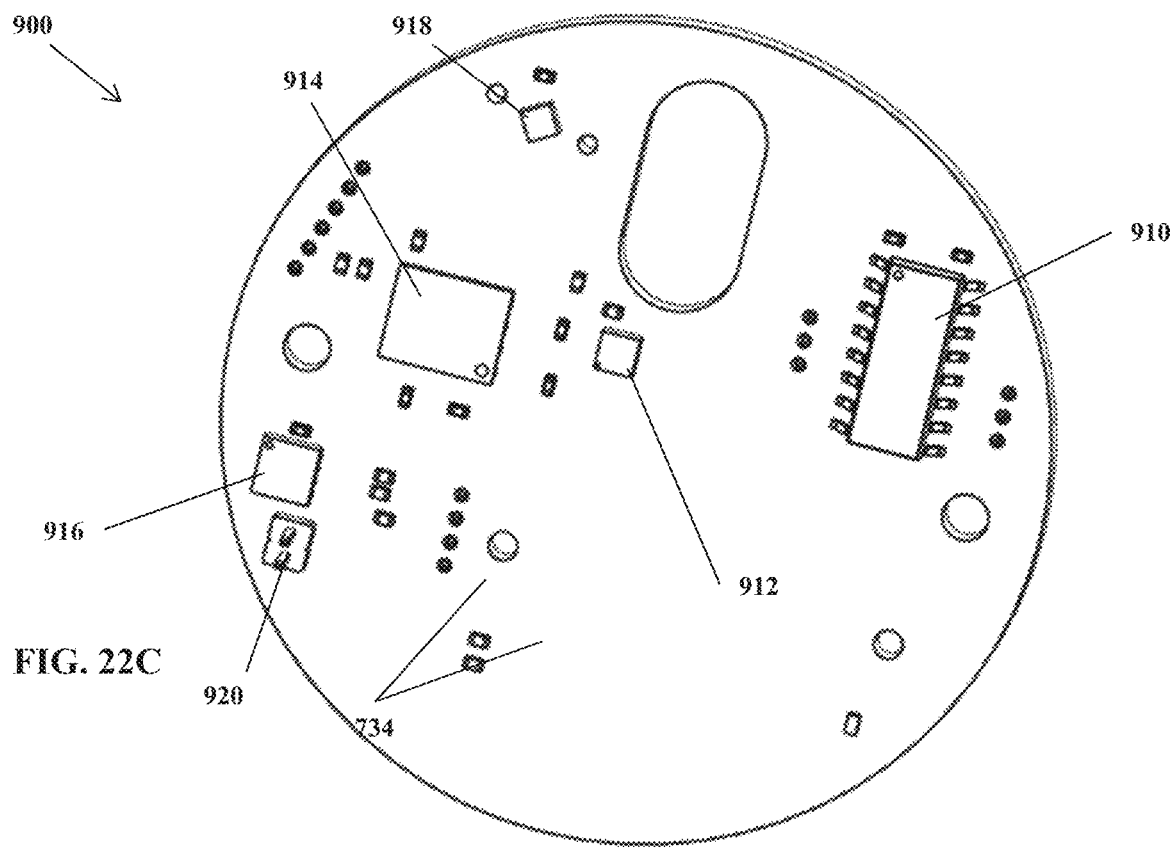
FIG. 22C is a perspective top view of the PCB layout.
Figure 22D:
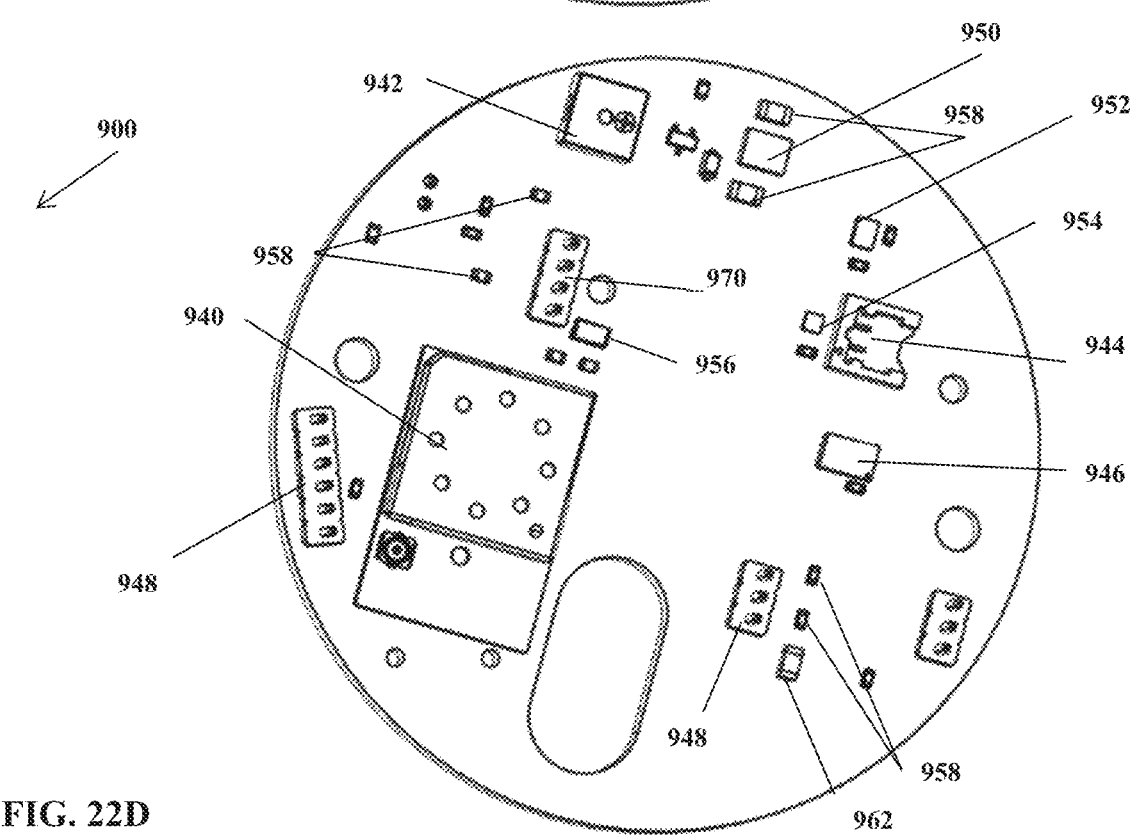
FIG. 22D is a perspective bottom view of the PCB layout.
Figure 22E:
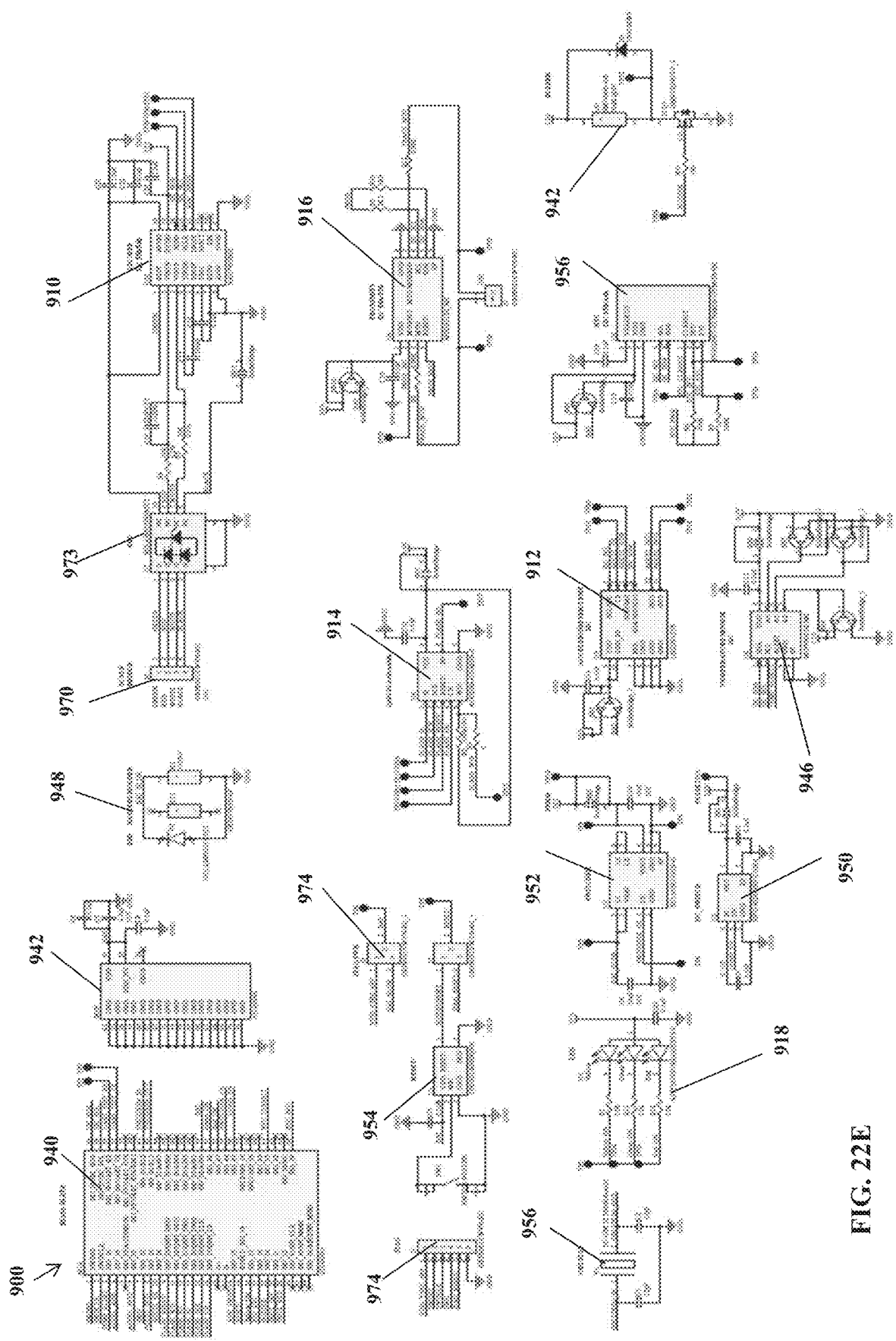
FIG. 22E is a schematic of the PCB layout.

As shown in FIGS. 22C-22E, the PCB layout 900 on the top side 731 of the PCB 730 and on the bottom side 733. The top side 731 includes an Analog to Digital Converters integrated circuit 910, an accelerometer 912, a memory card 914, a Proximity sensor 916, a LED array 918, a first connector 920, a JTAG connector 974. The bottom side 733 includes a Bluetooth module 940, a speaker 942, a switch 944, a temperature sensor 946, a plurality of connectors 948, a DC/DC converter 950, a load switch 952, a supervisory circuit 954, a clock crystal 956, first set of capacitors 958, thick film resistors 960, a second capacitor 962, and a bridge connector 970 operably coupled with the load cell.

As shown in FIG. 22E, a schematic of the PCB layout 900 is shown comprising the bridge connector 970, which is operably coupled with the load cell for measuring the third cap device and the associated container. The bridge connector 970 is operably coupled with a diode 973, which sends the load signal to the Analog to Digital Converters integrated circuit 910. At first Startup, the third cap Device is a 2-Point calibrated for weight-measurement and also proximity. A multi-point calibration and auto-tar (zeroing) functionality is in one embodiment. The calibration data stored in non-volatile ram storage component, so values are still stored after battery change. The calibration comprises the proximity sensor determine if the cap device is on/off the container, rather than checking if the proximity sensor is operable. And after the accelerometer interrupt has occurred, the proximity sensor checks if the cap device is on or off the container. If the proximity sensor detects that the cap device is on the container, then a weight measurement is conducted with the load cell. If off, the cap-off event is saved without taking the weight. The accelerometer is used to initiate the checking of the proximity sensor.

During Start-up, the hardware conducts an Initialization of BLE and Sensors. The sensors are I2C-slaves, according to one embodiment. I2C is a serial protocol for two-wire interface to connect low-speed devices like microcontrollers, EEPROMs, A/D and D/A converters, I/O interfaces and other similar peripherals in embedded systems. I2C is a synchronous, multi-master, multi-slave, packet switched, single-ended, serial computer bus. Bluetooth module reads data from the sensors digitally. Sensors have each one or more "interrupt lines" connected to the BLE module to wake up the module (if asleep) and indicate new data has been captured. The Sensors include the ADC, accelerometer, the proximity sensor, the temperature sensor. The ADC is the Analog-Digital-Converter for reading the force-sensor. The Accelerometer detects general movement/activity of device and orientation during weight-measurement. The proximity sensor detects if a container is attached to the cap device or not attached to the cap device. The proximity sensor consists of chip on the PCB to read the sensor and the actual sensor/antenna. The temperature sensor captures Temperature of the Device/Medication. The RTC is the Real Time Clock for time (alternatively the BLE module can capture time). Power-Management: Boost-Converter to supply a stable and higher than battery voltage to force sensor. Speaker and LED: notifications to user. Additional memory communicating through QSPI. The Idle-mode comprises as many components asleep as possible, BLE can be connected to (or not) and accelerometer watches for activity. Accelerometer-Interrupt comprises triggers BLE module which turns on proximity sensor.

When the Proximity sensor detects Cap Off of the container comprises saving "Cap off event" to memory and going back to the Idle-mode. When the Proximity sensor detects the third Cap device is on the container, it comprises waking up ADC to measure weight. The third cap device check for accelerometer for no movement and proper orientation. If the third cap device is not upright, then it warns patient through app and indicators and go back to check the accelerometer for no movement and proper orientation. The third cap device tries 3 times and if the third cap device is not upright, it saves "Cap on event" with invalid weight to memory, "bad chime" and goes back to the Idle-mode. If the third cap device is upright and still with no movement, then the third cap device initiates weight-measurement. The ADC takes weight measurements (100 samples) while watching accelerometer and proximity. If the weight measurement process is disrupted by movements or cap off, then the third cap device warns the user with a "bad chime" and tries again. If at least three weight measurements are attempted and the weight measurement process is still disrupted, then it saves "Cap on event" with invalid weight to memory, "bad chime" and goes back to Idle-mode warning the user. If a plurality of weight measurements are taken successfully without disruption, then it save "Cap on event" with valid weight to memory, sounds a "good chime" or positive indication and goes back to the Idle-mode.

The third cap device includes a Reminder-Functionality operation where a software application sends times of adherences to cap. If medication wasn't taken yet, the third cap device sounds "good chime" 30 mins before adherence and on time of scheduled adherence, and the third cap device sounds a "bad chime" 30 mins after adherence.

Capturing of Data from the software comprises storing events in a buffer. Whenever an event is being added, other events move one slot up, when buffer is full, the oldest event gets deleted. Buffer-Data (Service) consists of one characteristic for Time (Unixtime), Capstate, Orientation, Weight, Temperature and buffer-select. The software application writes into buffer-select which slot it wants to access and then the third cap device loads the data of this slot into the characteristics accordingly. Therefore, the software application always starts reading at slot 1 an increases until it reads a slot whose timestamp it has already read.

Figure 23:
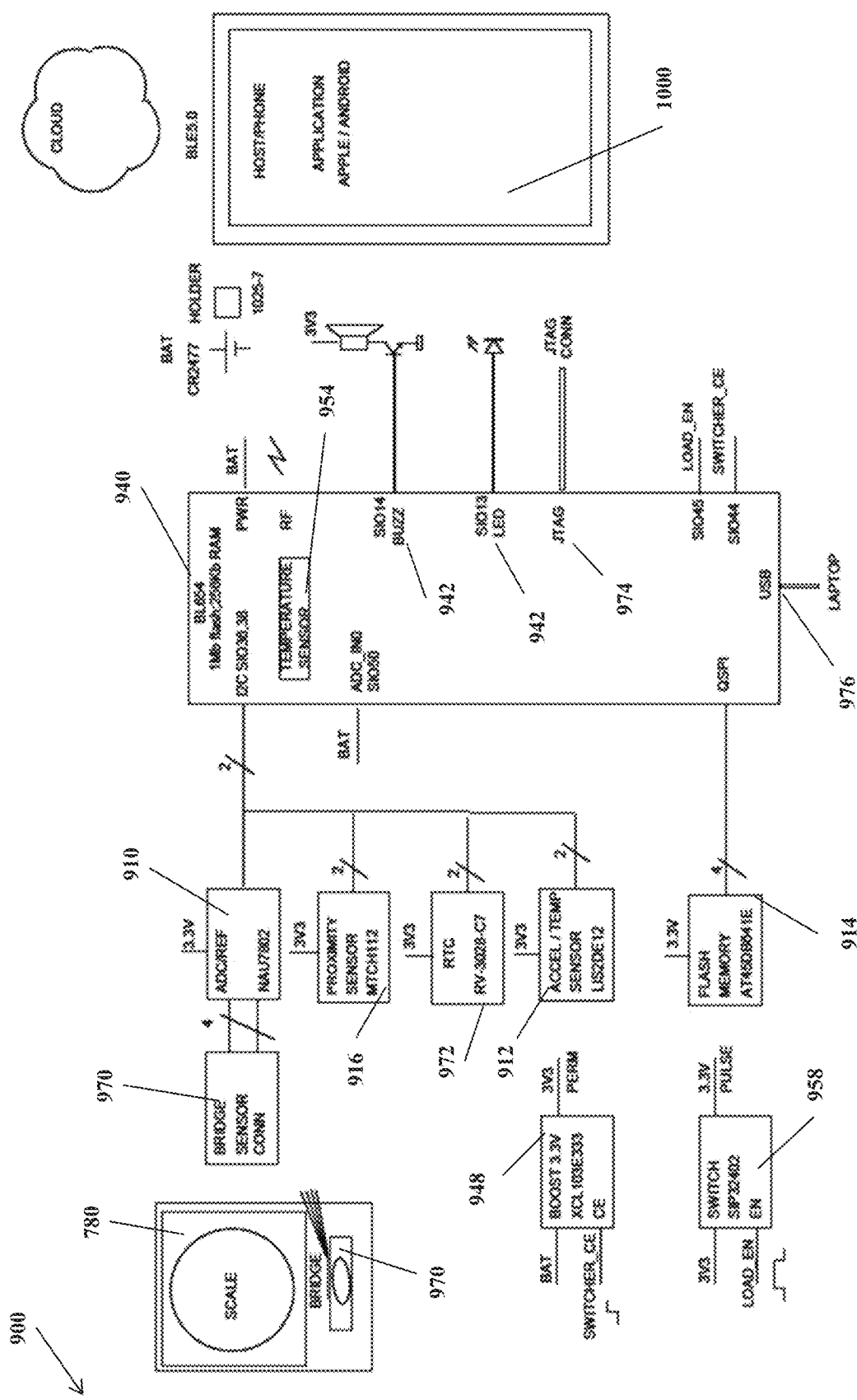
FIG. 23 is a flowchart of the PCB layout.

As shown in FIG. 23, a flowchart of the PCB layout 900 is shown comprising the load cell 780 operably coupled with the bridge connector 970. The bridge connector 970 is operably coupled with the Analog to Digital Converters integrated circuit 910. The Analog to Digital Converters integrated circuit 910 is operably coupled with the proximity sensor 916, a Real-time clock (RTC) 972, the accelerometer 912, and the Bluetooth module 940. The Bluetooth module 940 is operably coupled with the temperature sensor 946, the battery, the speaker 942, LED array 918, a JTAG connector 974, a USB port 976, and the memory card 914.

Figure 24A:
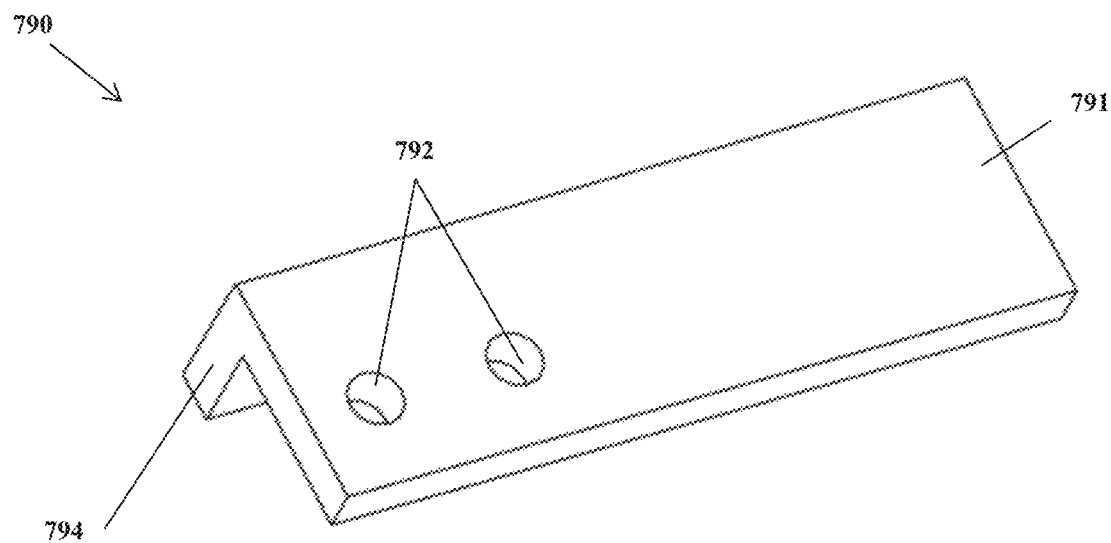
FIG. 24A is a perspective top view of the bottom stop cap.
Figure 24B:
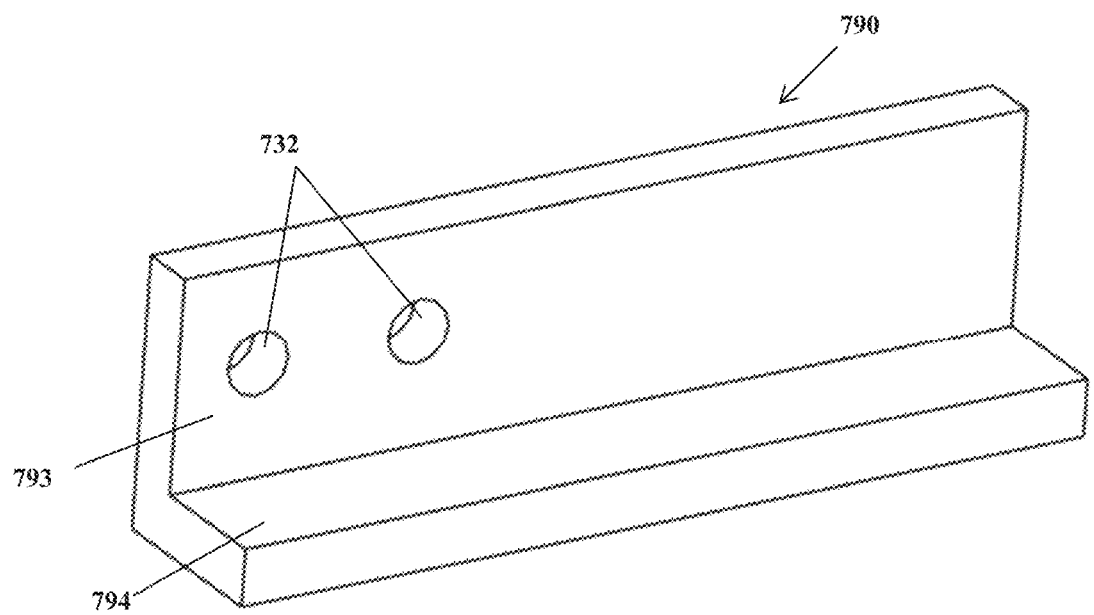
FIG. 24B is a perspective bottom view of the bottom stop cap.

As shown in FIGS. 24A-24B, the bottom stop cap 790 includes a top side 791 and a bottom side 793, and a general L-shape cross sectional configuration. The bottom stop cap 790 includes at least two holes 792 traversing the top side 791 and the bottom side 793. The at least two holes 792 operably couple with the plurality of screws 830 to secure the load cell and bottom stop cap 790 to the at least two second threaded lumens 768 of the first spacer cap 760. The bottom side 793 forms a right angle with an L-shaped portion 794, such as to sit and dispose on top of the load cell.

Figure 25A:
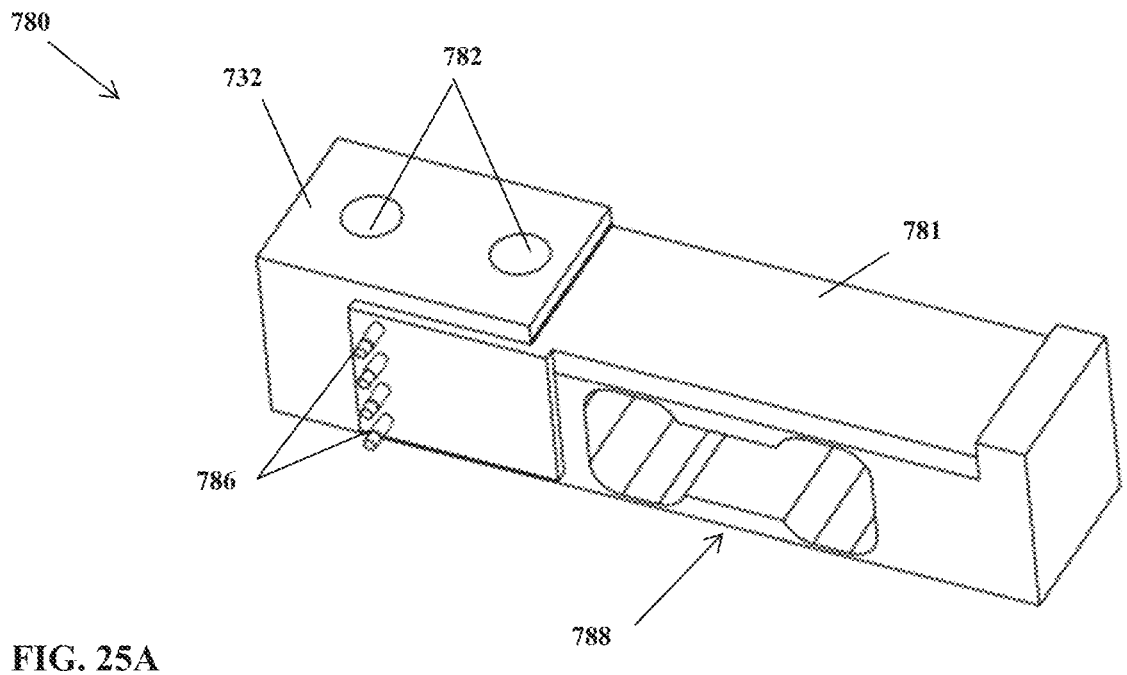
FIG. 25A is a perspective top view of the load cell.
Figure 25B:
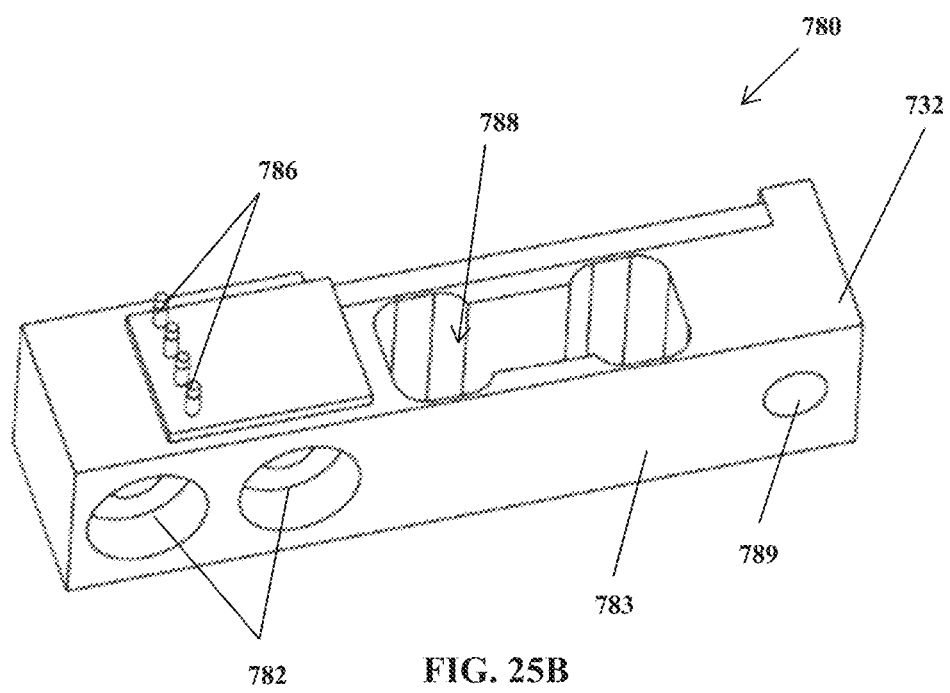
FIG. 25B is a perspective bottom view of the load cell.

As shown in FIGS. 25A-25B, the load cell 780 includes a top side 781, a bottom side 783, and a general rectangular configuration. The load cell 780 may be a force sensor as previously indicated or a type of transducer, specifically a force transducer. The load cell converts a force such as tension, compression, pressure, or torque into an electrical signal that can be measured and standardized. As the force applied to the load cell increases, the electrical signal changes proportionally. The load cell may be a hydraulic, pneumatic, piezoelectric, and strain gauge. Strain gauge load cells may be a Single point shear beam, a Pancake, a Double-ended shear beam, a Canister load cell, an S-type load cell, Wire rope clamps, a Tension link load cell. A Tension link load cell measures tension force. Wire rope clamps are an assembly attached to a wire rope and measures its tension. An S-type load cell comprises S-shaped spring element; can be used in both compression and tension. A Canister load cell comprises a cylindrical shaped spring element; can be used in both tension and compression. A Double-ended shear beam comprises a spring element fixed at both ends and loaded in the center. A Pancake comprises low-profile load cells often used in vessel weighing; can be tension or compression. Single point shear beam load cell comprises a spring element fixed at one end and loaded on the other.

As shown in FIGS. 25A-25B, the load cell 780 includes at least two holes 782 traversing the top side 781 and the bottom side 783. The at least two holes 782 operably couple with the plurality of screws 830 to secure the load cell and bottom stop cap 790 to the at least two second threaded lumens 768 of the first spacer cap 760. The at least two holes 782 can include a seated portion, such that the screw head abuts the seated portion when the screws are fastened. The load cell 780 includes a bottom hole 784 on the bottom side 783 as to secure the load cell 780 to the base cap 810 by way of a screw. The load cell 780 includes a plurality of electrical contacts 786 on the side of the load cell 780 to operably couple with the PCB. The load cell 780 includes a load lumen 788 through the load of the container may be measured. The load cell 780 includes a bottom hole 789 on the bottom side 783, wherein the bottom hole 789 operably couples with the base cap to secure the load cell 780 to the base cap 810. The Bluetooth module communicates with the medication adherence software application 1000, as further explained below.

Figure 26A:
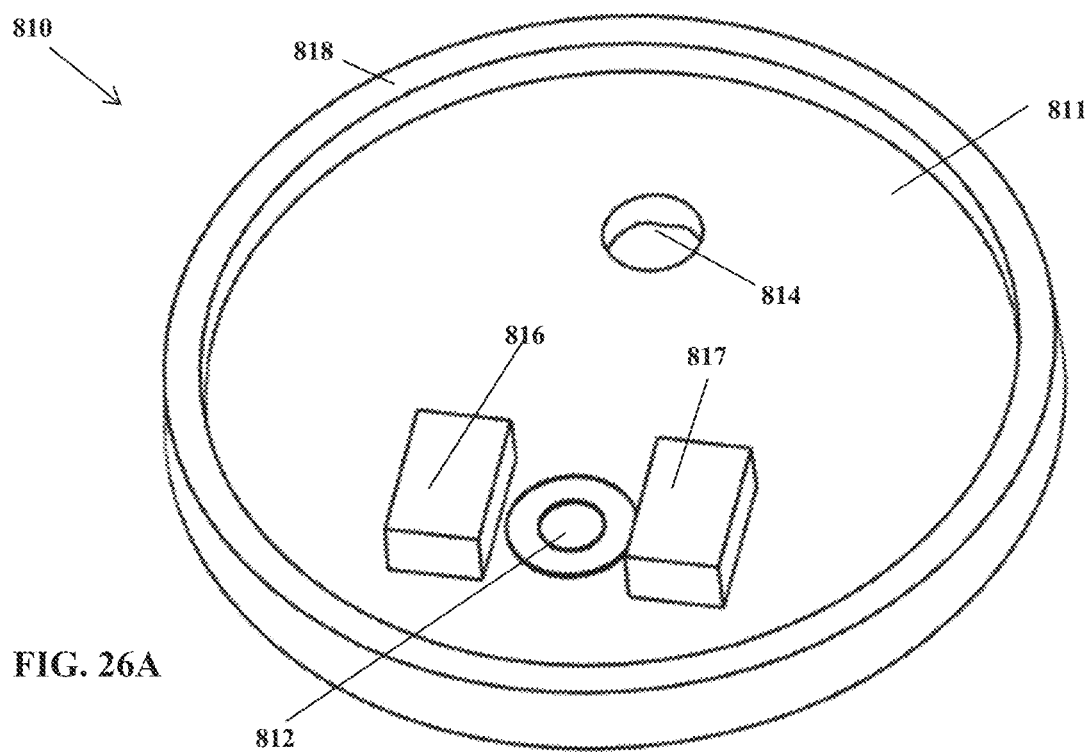
FIG. 26A is a perspective top view of the base cap.
Figure 26B:
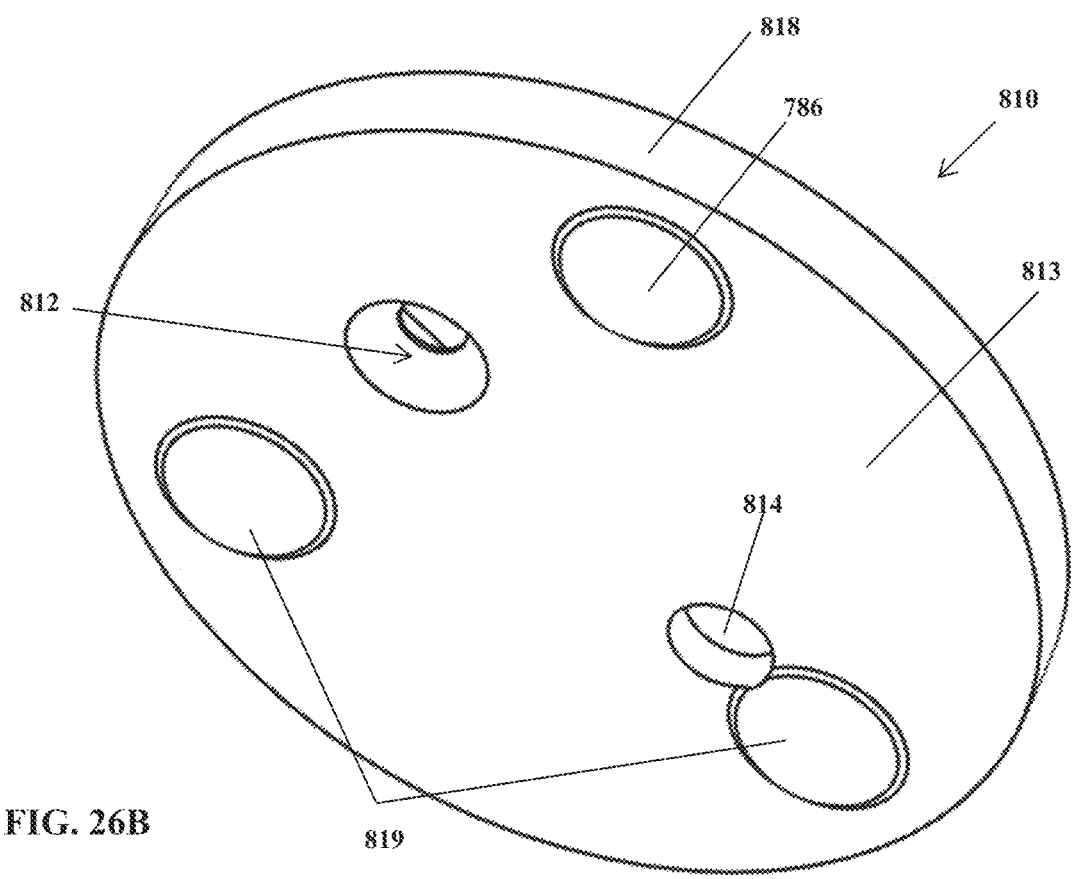
FIG. 26B is a perspective bottom view of the base cap.

As shown in FIGS. 26A-26B, the base cap 810 includes a top side 811, a bottom side 813, and a general circular configuration. The base cap 810 includes a first hole 812 traversing the top side 811 and bottom side 813, wherein the first hole 812 coaxially couples with the holes 782 of the load cell to secure the load cell to the base cap 810. In one embodiment, the first hole 812 includes a seated portion, such that the screw head abuts the seated portion when the screw is fastened. The base cap 810 includes a second hole 814 that coaxially couples with the bottom hole 789 of the load cell 780 to secure the load cell 780 to the base cap 810. The base cap 810 includes a first stop 816 and a second stop 817 which operably couple with the load cell 780 to seat the load cell in the base cap 810. In one embodiment, the second stop 817 abuts the L-shaped portion 794 of the bottom stop cap 790 and the first stop 816 abuts the load cell. The base cap 810 includes a circular lip 818 around the circumference of the top side 811. The base cap 810 includes a plurality of pads 819 on the bottom side 813.

Figure 27:
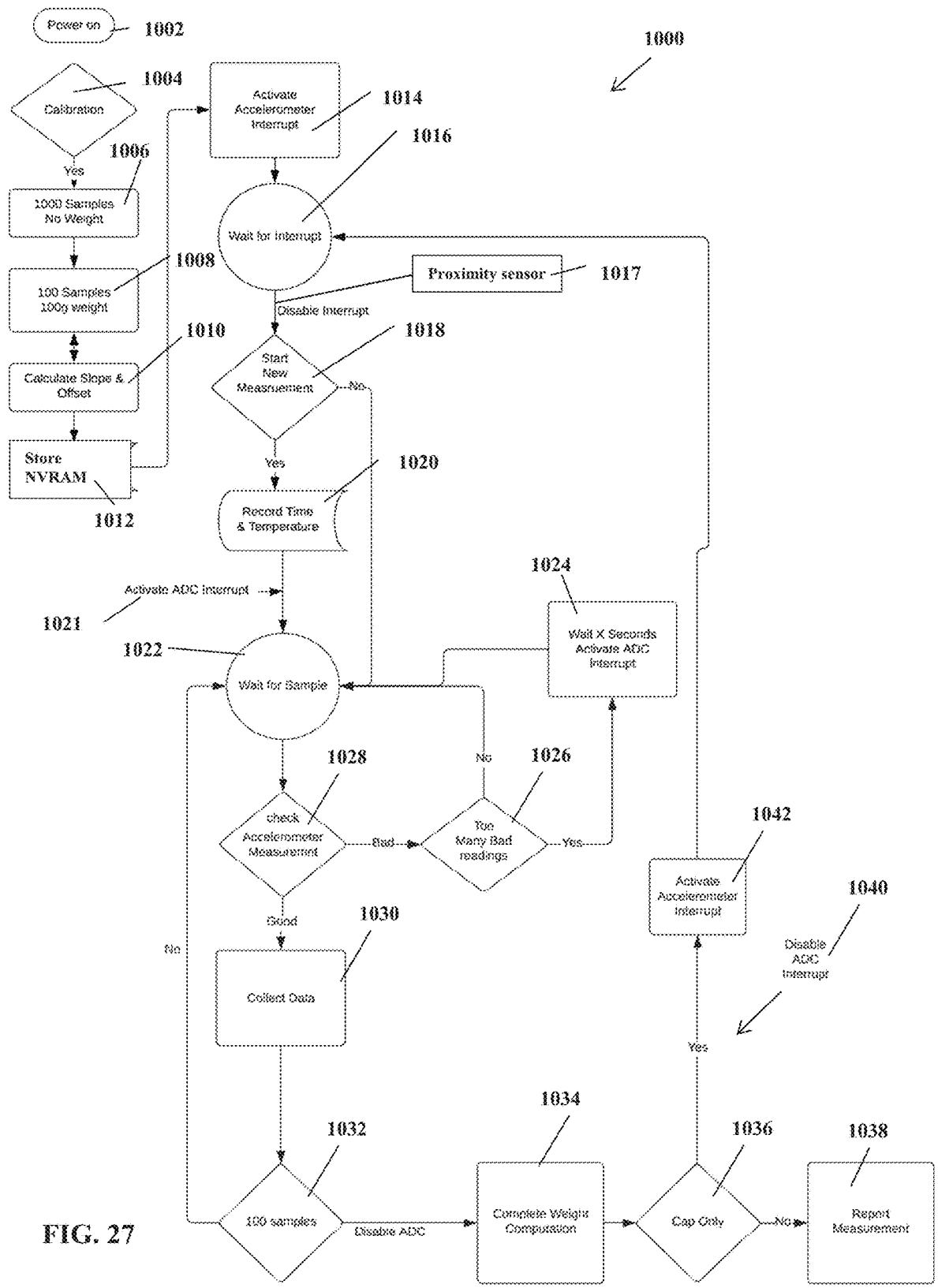
FIG. 27 is a schematic the medication adherence software application.

As shown in FIG. 27, in one embodiment, the medication adherence software application 1000 operates as follows: once the power is on 1002. The medication adherence software application 1000 then runs a calibration step 1004. Once the calibration step 1004 is complete and confirmed, samples for no weight is checked 1006, samples for a specific entered weight is checked 1008. Then, calculating the slope and offset is in step 1010 and storing the slope and offset calculation in the memory card in step 1012. The slope and offset calculation is sent to activate accelerometer interrupt in step 1014. Step 1016 waits for the interrupt in step 1014 and receives an input from activating the accelerometer interrupt is a disable ADC interrupt pathway 1040. And after the accelerometer interrupted has occurred, the proximity sensor checks if the cap device is on or off the container in step 1017. If the proximity sensor detects that the cap device is on the container, then a weight measurement is conducted with the load cell proceeding to decision step 1018. If the cap device is off of the container, then a cap-off event is saved without taking the weight measurement.

The disable interrupt proceeds to the decision step 1018 to start a new measurement. If a new measurement is started, then step 1020 records the time and temperature. If a new measurement is not started, then step 1022 waits for the sample. After the time and temperature are recorded in step 1020, the ADC interrupt is activated 1021 and step 1022 waits for the sample. Step 1022 receives two inputs and proceeds to step 1028 to check the accelerometer measurement. If the accelerometer measurement is good, the step 1030 collects the accelerometer data. If the accelerometer measurement is bad, the decision 1026 decides if there are too many bad readings. If there are not too many bad readings, then method proceeds to step 1022 to wait for the sample. If there are too many bad readings, then step 1024 waits X number of seconds to activate the ADC interrupt. After waiting X number of seconds, the method proceeds back to step 1022 to wait for the sample. If the accelerometer measurement is good, then step 1030 collects the data and Decision 1032 collects at least 100 samples. If 100 samples are not collected, then the method proceeds back to step 1022 to wait for the sample. If 100 samples are collected, then the ADC is disabled, and step 1034 completes the weight computation. The method proceeds to decision 1036 for the cap only. If there is a cap only, the ADC interrupt is disabled, and step 1042 activates the accelerometer interrupt. After activating the accelerometer interrupt in step 1042, the method proceeds back to step 1016 to wait for interrupt. If there is not the cap only in decision 1036, then step 1038 reports the measurement to the cloud or storage device.

In one embodiment, the load cell withstands about 200 g without changing the zero point. The cap device tolerates higher forces (withstanding weight) that that of the ointment being weighed to reduce frequency of product failure. If the ointment and container are greater than about 200 g, then the change in zero point is increased for the withstanding weight. The cap device includes a proximity sensor on the PCB, according to one embodiment. The cap device detect if a tube/container is attached to the third cap device. The cap device includes an ambient temperature sensor capable of measuring about 0 to about 60° C. with accuracy of ±2° C. between about 0 and about 60° C. Out-of-specification temperatures within the third cap device can compromise the performance of the cap device and storage of the prescription drug or ointment. Temperature is a parameter to be tracked by the device. The cap device includes an inclinometer. The third cap device measures tilt as it may affect accuracy of the weight measurement. The third cap device includes an accelerometer. The third cap device detects if the device is being moved or standing still. The load cell measures tubes up to about 100 g with a resolution between +/−0.1 g and +/−0.05 g. This parameter measures the mass difference after each use. Maximum tube mass is about 100 g. Dispensed range is between about 1.5-about 4 gm based on number and size of lesions.

In one embodiment, the power management requirements pertain to how the third cap device manages power. The third cap device measures battery voltage, such that there is a battery charge status. The third cap device includes a low power mode to prevent discharge when the third cap device is not in use by using low power requirements. The third cap device minimizes internal battery discharge. The third cap device includes a precision voltage regulation. Precision voltage achieves accurate measurements. The third cap device includes a non-rechargeable battery for enough power for the duration of use, according one embodiment.

In one embodiment, the timing requirements comprise details about how the third cap device creates and uses time. The third cap device log the times at which events occur. The third cap device requires an accurate time stamp for data logging. The third cap device includes a real time clock to determine when the patient takes their medication. The third cap device real time clock is accurate to +/− about 3 seconds after about 5 days of operation with Bluetooth connectivity. Time accuracy is for defining time of adherences. Main PCB includes a coin cell to maintain the real time clock and power the device. Battery power assists to maintain time, in one embodiment, the Data requirements include characteristics of data handled by the third cap device. Data saved in the third cap device is retrievable by Bluetooth. No wire connections are on the third cap device, in one embodiment. The third cap device saves at a minimum 80 events. If the device does not connect to a phone, the data is still available.

In one embodiment, the functional requirements include information pertaining to the operation and behavior as they relate to the device users. This third cap device functions in relationship to the user and other components. The third cap device measure tilt. Tilt may result in erroneous data measurements; tilt determines when measurements should and should not be taken. The third cap device report mass in a scaler for grams. Data consistency simplifies verification of data flow from the device to the cloud. The third cap device report temperature in a scaler for degrees Celsius or Fahrenheit. The third cap device detects when an ointment tube is attached or detached. The connection and disconnection of a tube/container to the third cap device provides valuable adherence information. The third cap device includes a design configuration to minimize error introduced by inclination or detect inclination that leads to an erroneous measurement. Measurement accuracy is important for defining adherence.

In one embodiment, the mechanical performance requirements define how each third cap device mechanically interacts with external devices and or accessories. The third cap device comprises multiple thread configurations to accommodate the most common tube threads. (thread sizes to include about 16, about 20, and about 28). The threads of third cap device include threads to match a commercially available non-prescription ointment.

In one embodiment, the external interface requirements define how the third cap device communicates with external devices and or accessories. The third cap device includes BLE 5.0 for a wireless interface is used for third cap device communication to the Software App. The third cap device includes a JTAG or serial port to load Software. A method of entering firmware into the device and general testing is included in the cap device. The third cap device includes a base that is non-stick in one embodiment. If the base sticks to the counter, picking it up may over stress the load. The third cap device material may be of plastic, metal, and the like. The third cap device is detectable and pairable to a phone. The third cap device connects via blue tooth or wireless technology to a portable device.

The User Interface (UI) Requirements of the third cap device include the following:

The third cap device emits yellow and green light as indicators. Green is to respond to a positive event and yellow to respond to a negative event. The third cap device notifies the user through an audible annunciator or speaker. The third cap device makes a plurality of sounds depending on device states. The third cap device includes at least one (1) LED that can emit programmable light. The third cap device displays one color at a time, in one embodiment; one light indicator is needed at a time. The audible annunciator creates two different tones, where one tone represents a positive event and one tone represents a negative event.

In one embodiment, the software and third cap device operate as follows:

If no interrupt for 24 hours, the cap device automatically takes a measurement, initiated either by the third cap device itself or the software app. Data is captured periodically and if no data is available, then an error report or message may be delivered by the third cap device or the software app. The cap device confirms medication use if other sensors are not working. Cap State can be defined as the on tube or off tube, Cap state on/off is an indicator for timing on when to take weight measurements. The proximity sensor detects if the container is on or if the container is off for the Cap state on or the Cap state off. The cap device knows if the cap device is calibrate or un-calibrated. The calibration state determines if the weight measurements are accurate. The third cap device is programmable with a time for patient to take medication a certain number of times a day. Medication taken at the prescribed time for efficacy. Reminders may be defined by present entries or by the user, reminders may be audible or visual cues under a particular set of circumstances. The third cap device may send an audible reminder or a visual reminder to connect to the software app. The third cap device reminds the patient to have the phone connected so data can be sent to the cloud or other remote server. The time period from last connect may be programmed into the third cap device. The third cap device comprises a number of events. In one embodiment, the number of events comprises 2 events/day for 5 weeks before re-setting the number of events to zero from the software app. The third cap device includes a sleep mode for components are put in sleep mode after a reading is taken. The battery power and the components go into a low power consumption state. The ADC may be in lower power mode. The third cap device puts the components in the sleep mode if a good reading is not obtained within 5 minutes of wake interrupt. The time period of 5 minutes allow the users to apply medication and to conserve battery power if good reading cannot be taken. The third cap device puts all components in the sleep mode if inclinometer is more than about 5 counts (of 63) from vertical after 5 minutes. If the third cap device is laid sideways, then the third cap device goes into battery power conservation mode. The third cap device takes a force measurement if inclinometer is vertical within about 5 counts (of 63) from the vertical orientation. The third cap device takes a weight measurement that is reasonably accurate if the inclinometer is within about 5 degrees off the vertical orientation. The third cap device sends an audible alarm if the third cap device is not placed in the vertical orientation after 5 seconds of the third cap device being secured to the container. A good measurement is taken after medication is used and the third cap device remind patient independent of app. The third cap device reports the non-vertical orientation to app after 5 seconds of cap on. The software app is notifying if the cap device is not vertical so the software app can also remind the patient to place cap upright.

User interface requirements comprise the following:

Light indicator and audible alarm is initiated 30 minutes prior to medication time if patient did not take medication. The cap device initiates a reminder for patient to take medication determined if the cap device is on or off the container, a weight change detected in the container, and within a time period window, such as 2 hours before. The cap device includes a positive light indicator and a positive audible alarm after successful weight measurement by the third cap device. The cap device provides positive feedback to patient. The cap device includes a negative light indicator and a negative audible alarm after a time period of about 30 minutes after medication time if no successful weight measurement is obtained. The cap device sends a reminder for patient to take medication through the software app. The cap device includes a negative light indicator and a negative audible alarm after a time period of about 3 seconds when cap device is in on the container and when the cap device is not placed in the vertical orientation. The cap device sends a timely reminder for patient to place the cap device/tube in the vertical orientation so a good accurate measurement can be taken. The cap device includes multiple light indicators in the event that is requested to be on, a yellow light indicator takes precedence over green light indicator. Patient should not have conflicting/overlapping indicators. The cap device includes a successful medication state and initiates a successful light indicator and a successful audible noise. The successful medication state is reinforcement to the patient and the negative medication state includes a negative noise. The software app activates the successful light indicator and the negative audible noise independent of the cap device activity or events. The software app can be used to test the cap device functionality or independently notify the patient of an event. The software app activates all LED colors individually independent of Cap activity or events. Can be used to test the cap functionality or independently notify the patient of an event. The successful audible noise is 2 tones alternating (E+C) 6 times of about 300 ms on and about 300 ms off. The negative audible noise is different than the successful audible noise. A second successful audible noise is 1 tone (F) 3 times of 300 ms on and 300 ms off. The second successful audible noise is different than the negative audible noise. The cap device and software can set up the successful audible noise and successful light indicators. The successful audible noise and successful light indicators are positive feedback that programmed for the patient.

The cap device includes an acceleration measured at about 0.015 g resolution. Inclination determines if a measurement should be taken. The accelerometer is working both in read and interrupt mode. The accelerometer parameters for waking up the cap device.

In one embodiment, acceleration is sampled at about 10 Hz. This sampling is timed with the ADC sample rate which is about 10 Hz. Accelerometer provides inclination of Z vector. Primary vector to determine if the tube/cap is upright and a good weight measurement can be taken. Accelerometer has +/−2 g=^+/−127 counts, therefore resolution is about 0.015 g. Temperature is measured at about 0.1 C resolution. Some medication is temperature sensitive and this is indicated on the medication storage temperature. Temperature sensor in accelerometer working. Current accuracy is within 1° C. of dedicated temp sensor. Temp should be taken right at wake up as a surrogate for medication storage temperature. Load Cell/ADC able to measure force in grams +/−0.05 g. Resolution is 0.005 g. Output should be in units to be used by the Software App. Load cell sample rate is 10 Hz. Lowest rate of ADC which sets this parameter. Load cell is filtered by averaging 100 samples. Reduces noise by factor of 10; 10 seconds is reasonable for cap to remain vertical; and not too much battery power is consumed. Battery voltage is read and sent to the app. App can indicate low battery voltage independent of cap indicators.

Pairing process can occur with any device. A process is pairs a patient's phone prior to first use. Measurement Data is reported from app requests. The type of units to be reported is in actual units used in the phone app/cloud platform. A complete measurement can be made—weight, time, temperature and cap state. Report is in grams, seconds (Unix Time), and degrees C. BT advertises every 5 seconds and is intermittent to save battery life, but not longer than 10 seconds such that it is difficult to connect app to cap device.

Software application comprises a 2 point calibration (0, 100 g), in one embodiment. In order to achieve the accuracy, the load cells are individually calibrated after insertion of a battery. Requires Interface document to be updated and support added by the app. The software app implements the tare weight. Implement a terminal version of the program or add to app. Calibration data is stored in the cap device, or stored in the cloud for future reference, or to understand if offset changes over time. In non-volatile memory, the calibration data is uploaded to a cloud server. Sending the calibration data to the app to verify proper assembly and calibration. The medicine type is either read by a scanning device or written into the software app. The cap device knows the kind of medicine by either a medical ID code, a field to fill in by the user, or a QR code scanned to identify the medicine type. The software version is written by the programming/calibration app and read by the use software app. The cap includes its configuration so the app knows which version it is talking with for future versions. Requires Interface document to be updated and support added by the app. At initial patient usage, when medication is entered: starts data capture, TX/RX parameters are bumped to "active mode"; the sound indicator is activated. The cap device converts from "shipping mode" to "active mode" when going to be used by the patient. After calibration device is put in standby mode with only BT working infrequently until Medicine ID is entered user. The cap device conserves battery life until ready to be used by the patient. Medicine ID is wiped during calibration. A factory medicine ID may be used.

Data is saved to External Memory. If a patient doesn't connect to a phone for several days, the cap device stores all collected data until upload via BLE is possible. Sound annunciator is turned off with the following events: app, shake cap, turn upside down, 10 second timer×10 sec break 3 times. The audible annunciator does not run all the time by a fail-safe check.

The load cell resolution meets the requirement of about 0.05 g. The accuracy of the load cell is determined through calibration and error correction. Using simple 2-point calibration (linear, with zero offset and slope), the maximum error is about 0.162 g. Accuracy can further be increased with multipoint stepwise, linear calibration, or non-linear calibration. The load cell comprises an absolute accuracy and repeatability better than 0.05 g, absolute accuracy can fluctuate over the weight applied (i.e. from about 0-about 100 g)

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the information signal and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A medication adherence apparatus comprising:
   a container element operably and detachably coupled to a cap device;
   the cap device comprising a force sensor configured to measure a weight of the container element, an orientation sensor configured to detect an orientation of the cap device, a temperature sensor configured to detect a temperature inside the container element, and a proximity sensor configured to detect a cap off state when the container element is detached from the cap device and a cap on state when the container element is attached to the cap device;
   wherein the cap device receives a medication schedule and notification parameters to notify a patient by an alarm if medication is missed, wherein the alarm is selected from the group consisting of: an audio sound, a visual notification, an electronic notification, or a cell phone notification;
   wherein upon the proximity sensor detecting that the cap device has been altered from the cap off state to the cap on state, the orientation sensor detects the orientation of the cap device to determine if the cap device is upright generally along a vertical axis and detects for movement of the cap device, and upon the orientation sensor detecting that the cap device is upright and not moving, the force sensor measures the weight of the container element;
   wherein if upon the proximity sensor detecting that the cap device has been altered from the cap off state to the cap on state the orientation sensor detects that the orientation of the cap device is not upright, the cap device notifies the patient to correct the orientation to upright and the orientation sensor checks the orientation of the cap device again; and
   wherein if the cap device is not detected to be upright after being checked by the orientation sensor multiple times, the cap device creates a first dataset with a timestamp, a state of the cap device, the orientation of the cap device, and the temperature inside the container element, without recording the weight of the container element.

2. The medication adherence apparatus according to claim 1, wherein the container element is selected from the group consisting of: an ointment tube, wide-mouthed plastic jar, or a platform developed for storage, display, and utilization of medicament container such as a tube, pill bottle, balm jar or tray.

3. The medication adherence apparatus according to claim 2, wherein the container element houses a medication selected from the group consisting of: pill, powder, liquid, or gas form.

4. The medication adherence apparatus according to claim 3, further comprising a hardware system combining sensors to record the orientation, the temperature, the timestamp, and a location of the cap device, wherein the hardware system is operably coupled to a mobile device or a computing device.

5. The medication adherence apparatus according to claim 4, wherein the hardware system is configured to send an information signal to a mobile application or a server.

6. The medication adherence apparatus according to 5, wherein the cap device comprises a PCB, a first main housing, a first battery cover, a first spacer cap, a battery, the force sensor comprising a load cell, a bottom stop cap, a light pipe, and a base cap, a Surface Mount Transducer; and a plurality of screws; the load cell detects a movement and connection of the cap device to the container element; and a detection signal is sent to a remote module to notify the patient if the cap device is secured to the container element and notifies a program or module every time the cap device is removed or secured to the container element, wherein the battery is operably disposed in the first battery cover and positioned over the PCB; the first battery cover is operably coupled with the first spacer cap; the first spacer cap is operably coupled with the light pipe and is operably disposed over the PCB; a first screw and a second screw secures the first main housing to the first spacer cap; the PCB is operably coupled with the Surface Mount Transducer and the PCB is operably disposed with the load cell; and the load cell is operably disposed on the base cap.

7. The medication adherence apparatus according to claim 1 wherein the container element is an ointment tube containing a topical medication.

8. The medication adherence apparatus according to claim 1 wherein upon the proximity sensor detecting that the cap device has been altered from the cap on state to the cap off state, the cap device obtains a second timestamp including a time and date.

9. The medication adherence apparatus according to claim 1 wherein the cap device records a start adherence time when the cap device has been altered from the cap on state to the cap off state and an end adherence time when the cap device has been altered from the cap off state to the cap on state.

10. The medication adherence apparatus according to claim 1 wherein if the cap device is detected to be upright during any one of the checks by the orientation sensor, the cap device creates a second dataset with the timestamp, the state of the cap device, the orientation of the cap device, the temperature inside the container element, and the weight of the container element.

11. The medication adherence apparatus according to claim 1 wherein the proximity sensor is a capacitive sensor.

12. A medication adherence apparatus comprising:
a container containing an ointment;
a cap device detachably coupled to the container, the cap device comprising:
  a force sensor configured to measure a weight of the container;
  an orientation sensor configured to detect an orientation of the cap device; and
  a proximity sensor configured to detect a cap state of the cap device, wherein the cap state comprises a cap off state when the container is detached from the cap device and a cap on state when the container is attached to the cap device;
wherein upon the proximity sensor detecting that the cap device has been altered from the cap off state to the cap on state, the orientation sensor detects the orientation of the cap device to determine if the cap device is upright generally along a vertical axis and detects for movement of the cap device, and upon the orientation sensor detecting that the cap device is upright and not moving, the force sensor measures the weight of the container;
wherein if upon the proximity sensor detecting that the cap device has been altered from the cap off state to the cap on state the orientation sensor detects that the orientation of the cap device is not upright, the medication adherence apparatus notifies the patient to correct the orientation to upright and the orientation sensor checks the orientation of the cap device again, and wherein if the cap device is not detected to be upright after being checked by the orientation sensor multiple times, the cap device creates a first dataset with a timestamp, the cap state of the cap device, and the orientation of the cap device, without recording the weight of the container.

13. The medication adherence apparatus according to claim 12 wherein the container is a tube and the ointment is a topical medication.

14. The medication adherence apparatus according to claim 12 further comprising:
wherein if the cap device is detected to be upright during any one of the multiple times, the cap device creates a second dataset with the timestamp, the state of the cap device, the orientation of the cap device, and the weight of the container.

15. The medication adherence apparatus according to claim 12 wherein the proximity sensor is a capacitive sensor.

16. The medication adherence apparatus according to claim 12 wherein the cap device comprises a bottom end, a top end, and a connector portion comprising:
a central lumen extending from an opening in the top end of the cap device to a floor that is elevated above the bottom end of the cap device; and
a threaded inner surface that is configured for operable coupling with a top connecting portion of the container such that no portion of the container extends beyond the floor of the central lumen of the connector portion when connected to the cap device.

17. The medication adherence apparatus according to claim 16 wherein the cap device comprises a cavity located between the floor of the central lumen of the connector portion and the bottom end of the cap device, and wherein the force sensor, the orientation sensor, the proximity sensor, and a battery that is configured to power the force sensor, the orientation sensor, and the proximity sensor are located within the cavity.

18. The medication adherence apparatus according to claim 17 wherein when the container is coupled to the cap device, the force sensor, the orientation sensor, and the proximity sensor are located between the container and the battery.

* * * * *